US007060795B2

(12) United States Patent
Quirk

(10) Patent No.: US 7,060,795 B2
(45) Date of Patent: Jun. 13, 2006

(54) WOUND CARE COMPOSITIONS

(75) Inventor: Stephen Quirk, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 575 days.

(21) Appl. No.: 10/325,446

(22) Filed: Dec. 19, 2002

(65) Prior Publication Data

US 2004/0121438 A1 Jun. 24, 2004

(51) Int. Cl.
*C07K 14/00* (2006.01)
*C12N 15/09* (2006.01)
*A61K 38/00* (2006.01)

(52) U.S. Cl. ..................... 530/350; 435/69.4; 514/12
(58) Field of Classification Search .............. 514/12; 435/69.2; 530/350
See application file for complete search history.

(56) References Cited

U.S. PATENT DOCUMENTS 5,714,465 A 2/1998 Langley et al.
5,914,392 A 6/1999 Hawkins et al.

FOREIGN PATENT DOCUMENTS

EP 1041083 A1 10/2000

OTHER PUBLICATIONS

Shimizu et al. Cloning and sequencing of the cDNA encoding a mouse tissue inhibitor of metalloproteinase-2. Gene. 1992. 114, 291-292.*
Arnold, Ulrich, "Kinetic and Thermodynamic Thermal Stabilities of Ribonuclease A and Ribonuclease B", *Biochemistry*, 36, (1997), 2166-2172.
Becker, Joseph W., "Stromelysin-1: Three-dimensional structure of the inhibited catalytic domain and of the C-truncated proenzyme", *Protein Science*, 4, (1995), 1966-1976.
Bodden, M. Kirby, et al., "Functional Domains of Human TIMP-1 (Tissue Inhibitor of Metalloproteinases)", *The Journal of Biological Chemistry*, 269 (29), (1994), 18943-18952.
Browner, Michelle F., "Matrilysin-Inhibitor Complexes: Common Themes among Metalloproteases", *Biochemistry*, 34, (1995), 6602-6610.
Butler, Georgina S., et al., "The Specificity of TIMP-2 for Matrix Metalloproteinases Can Be Modified by Single Amino Acid Mutations", *The Journal of Biological Chemistry*, 274 (29), (1999), 20391-20396.
Colandrea, Teresa D., "Epidermal Expression of Collagenase Delays Wound-Healing in Transgenic Mice", *The Journal of Investigative Dermatology*, (1998), 1029-1033.
Duivenvoorden, Wilhelmina C., "Use of Tetracycline as an Inhiitor of Matrix Metalloproteinase Activity Secreted by Human Bone-Metastasizing Cancer Cells", *Invasion Metastasis*, 17, (1997), 312-322.

Fernandez-Catalan, Carlos, "Crystal structure of the complex formed by the membrane type 1-matrix metalloproteinase with the tissue inhibitor of metalloproteinases-2, the soluble progelatinase A receptor", *The EMBO Journal*, 17 (17), (1998), 5238-5248.
Gabb, Henry A., et al., "Modelling Protein Docking using Shape Comlementarity, Electrostatics and Biochemical Information", *Journal of Molecular Biology*, 272, (1997),106-120.
Gomis-Ruth, Franz-Xaver, "Mechanism of inhibition of the human matrix metalloproteinase stromelysin-1 by TIMP-1", *Letters to Nature*, 389, (1997), 77-81.
Grams, Frank, "X-ray structures of human neutrophil collagenase complexed with peptide hydrozamate and peptide thiol inhibitors", *European Journal of Biochemistry*, 228, (1995), 830-841.
Guex, Nicolas, "Swiss-MODEL and the Swiss-Pdb Viewer: An environment for comparative protein modeling", *Electrophesis*, 18, (1997), 2714-2723.
Higgins, Desmond G., "Clustal V: improved software for multiple sequence alignment", *Computer applications in the biosciences*, 8 (2), (1992), 189-191.
Hodges, Deborah J., et al., "Preparation of recombinant tissue inhibitor of metalloproteinases-1 (TIMP-1) in high yield and identification of a hydrophobic surface feature", *Eur. J. Biochem*, 257, (1998), 562-569.
Howard, Eric W., "Preferential Inhibition of 72- and 92-kDa Gelatinases by Tissue Inhibitor of Metalloproteinases-2", *The Journal of Biological Chemistry*, 266 (20), (1991), 13070-13075.
Huang, Wen, "Folding and characterization of the amino-terminal domain of human tissue inhibitor of metalloproteinases-1 (TIMP-1) expressed at high yield in *E. coli*", *FEBS Letters*, 384, (1996), 155-161.
Hutton, Mike, et al., "Analysis of the Interaction of TIMP-2 and MMPs: Engineering the Changes", *Annals of the New York Academy of Sciences*, 878, (Jun. 1999), 524-527.
Kaiser, Donald A., et al., "Characterization of Actin and Poly-L-proline Binding Sites of Acanthamoeba Profilin with Monoclonal Antibodies and by Mutagenesis", *Journal of Molecular Biology*, 256, (1996), 89-107.
Karlsson, Robert, et al., "Experimental Design for Kinetic Analysis of Protein-Protein Interactions with surface plasmon resonance biosensors", *Journal of Immunological Methods*, 200, (1997), 121-133.
Levy, Daniel E., "Matrix Metalloproteinase Inhibitors: A Structure-Activity Study", *Journal of Medicinal Chemistry*, 41, (1998), 199-223.

(Continued)

*Primary Examiner*—Robert A. Wax
*Assistant Examiner*—Suzanne M. Mayer
(74) *Attorney, Agent, or Firm*—Schwegman, Lundberg, Woessner & Kluth, P.A.

(57) ABSTRACT

The invention provides polypeptides that can inhibit the activity of matrix metalloproteinases. Such polypeptides are useful for treating wounds, for example, chronic wounds.

24 Claims, 17 Drawing Sheets

OTHER PUBLICATIONS

Libson, Andrew M., "Crystal structure of the haemopexin-like C-terminal domain of gelatinase A", *Nature Structural Biology*, 2 (11), (1995), 938-942.

Liu, Yiliang E., et al., "Preparation and Characterization of Recombinant Tissue Inhibitor of Metalloproteinase 4 (TIMP-4)", *The Journal of Biological Chemistry*, 272 (33), (1997), 20479-20483.

Lofas, Stefan, "Dextran modified gold for surfaces for surface plasmon resonance sesnors: immunoreactivity of immobilized antibodies and antibody-surface interaction studies", *Colloids and Surfaces B: Biointerfaces*, 1, (1993), 83-89.

Meng, Qi, et al., "Residue 2 of TIMP-1 Is a Major Determinant of Affinity and Specificity for Matrix Metalloproteinases but Effects of Substitutions Do Not Correlate with Those of the Corresponding P1' Residue of Sbustrate", *The Journal of Biological Chemistry*, 274 (15), (1999), 10184-10189.

Morton, Thomas A., "Intetpreting Complex Binding Kinetics from Optical Biosensors: A Comparison of Analysis by Linearization, the Integrated Rate Equation, and Numerical Integration", *Analytical Biochemistry*, 227, (1995), 176-185.

Moses, M. A., "Temporal Study of the Activity of Matrix Metalloproteinases and Their Endogenous Inhibitors During Wound Healing", *Journal of Cellular Biochemistry*, 60, (1996), 379-386.

O'Shannessy, Daniel J., "Determination of Rate and Equilibrium Binding Constants for Macromolecular Interactions Using Surface Plasmon Resonance: Use of Nonlinear Squares Analysis Methods", *Analytical Biochemistry*, 212, (1993), 457-468.

Odake, Shinjiro, "Inhibition of matrix metalloproteinase by peptidyl hydroxamic acids", *Biochemical and Biophysical Research Communications*, 199 (3), (1994), 1442-1446.

Olson, Matthew W., "Kinetic Analysis of the Binding of Human Matrix Metalloproteinase-2 and -9 to Tissue Inhibitor of Metalloproteinase (TIMP)-1 and TIMP-2", *The Journal of Biological Chemistry*, 272 (47), (1997), 29975-29983.

Overall, Christopher M., et al., "Identification of the Tissue Inhibitor of Metalloproteinases-2 (TIMP-2) Binding Site on the Hemopexin Carboxyl Domain of Human Gelatinase A by Sie-directed Mutagenesis", *The Journal of Biological Chemistry*, 274 (7), (1999), 4421-4429.

Peitsch, Manuel C., "Automated Modelling of the Transmembrance Region of G-protein Coupled Receptor by Swiss-Model", *Receptors and Channels*, 4, (1996), 161-164.

Peitsch, M. C., " ProMod and Swiss-Model: Internet-based tools for automated comparative protein modelling", *Biochemical Society Transactions*, 24, (1996), 274-279.

Quirk, Stephen, "Primary Structure of and Studies on Acanthamoeba Actophorin", *Biochemistry*, 32(33), (1993), 8525-8533.

Reinemer, Peter, "Structural implications for the role of the N terminus in the 'superactivation' of collagenases", *FEBS Letters*, 338, (1994), 227-233.

Saarialho-Kere, U.K., "Patterns of matrix metaloproteinase and TMP expression in chronic ulcers", *Archives of Dermatological Research*, 290, (1998), S47-S54.

Sanger, F., "DNA sequencing with chain-terminating inhibitors", *Proceedings of the National Academy of Sciences USA*, 74 (12), (Dec. 1977), 5463-5467.

Sayle, Roger A., "RASMOL: biomolecular graphics for all", *Trends in Biochemical Sciences*, 20, (1995), 333-379.

Siegel, Lewis M., "Determination of Molecular Weights and Frictional Ratios of Proteins . . . ", *Biochemica Et Biophysica Acta*, 112, (1966), 346-362.

Su, Jui-Lan, "Monoclonal Antibodies against Human Collagenase and Stromelysin", *Hybridoma*, 14 (4), (1995), 383-390.

Taylor, Kenneth B., "The Mechanism of Inhabitation of Collagenase by TIMP-1", *The Journal of Biological Chemistry*, 271 (39), (1996), 23938-23945.

Tuuttila, Ari, "Three-dimensional Structure of Human Tissue Inhibitor of Metalloproteinases-2 at 2.1 A Resolution", *Journal of Molecular Biology*, 284, (1998), 1133-1140.

Vaalamo, Maarit, "Distinct populations of stromal cells express collagenase-3 (MMP-13) and collagenase-1 (MMP-1) in chronic ulcers but not in normally healing wounds", *The Journal of Investigative Dermatology*, 109 (1), (1997), 96-101.

Vaalamo, M., "Patterns of matrix metalloproteinase and TIMP-1 expressions in chronic and normally healing human cutaneous wounds", *British Journal of Dermatology*, 135, (1996), 52-59.

Vallon, Rudiger, et al., "The catalytic domain of activated collagenase I (MMP-1) is absolutely required for interaction with its specific inhibitor, tissue inhibitor of metalloproteinases-1 (TIMP-1)", *Eur. J. Biochem.*, 224, (1997), 81-88.

Weckroth, Miina, "Matrix Metalloproteinases, Gelatinase and Collagenase, in Chronic Leg Ulcers", *The Journal of Investigative Dermatology*, 106 (5), (1996), 1119-1123.

Wingfield, Paul T., et al., "Biophysical and Functional Characterization of Full-length, Recombinant Human Tissue Inhibitor of Metalloproteinases-2 (TIMP-2) Produced in *Escherichia coli*", *The Journal of Biological Chemistry*, 274 (30), (1999), 21362-21368.

Wojtowicz-Praga, Slawomir M., "Matrix Metalloproteinase Inhibitors", *Investigative New Drugs*, 15, (1997), 61-75.

\* cited by examiner

A.

B.

1  2

SEQUENCE LISTING

<160> NUMBER OF SEQ ID NOS: 21

<210> SEQ ID NO 1
<211> LENGTH: 207
<212> TYPE: PRT
<213> ORGANISM: Homo sapiens

<400> SEQUENCE: 1

```
Met Ala Pro Phe Glu Pro Leu Ala Ser Gly Ile Leu Leu Leu Leu Trp
1               5                   10                  15

Leu Ile Ala Pro Ser Arg Ala Cys Thr Cys Val Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
        115                 120                 125

Asn Ser Leu Ser Leu Ala Gln Arg Arg Gly Phe Thr Lys Thr Tyr Thr
    130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
        195                 200                 205
```

<210> SEQ ID NO 2
<211> LENGTH: 220
<212> TYPE: PRT
<213> ORGANISM: Homo sapiens

<400> SEQUENCE: 2

```
Met Gly Ala Ala Ala Arg Thr Leu Arg Leu Ala Leu Gly Leu Leu Leu
1               5                   10                  15

Leu Ala Thr Leu Leu Arg Pro Ala Asp Ala Cys Ser Cys Ser Pro Val
            20                  25                  30

His Pro Gln Gln Ala Phe Cys Asn Ala Asp Val Val Ile Arg Ala Lys
        35                  40                  45

Ala Val Ser Glu Lys Glu Val Asp Ser Gly Asn Asp Ile Tyr Gly Asn
    50                  55                  60
```

```
Pro Ile Lys Arg Ile Gln Tyr Glu Ile Lys Gln Ile Lys Met Phe Lys
 65                  70                  75                  80

Gly Pro Glu Lys Asp Ile Glu Phe Ile Tyr Thr Ala Pro Ser Ser Ala
                 85                  90                  95

Val Cys Gly Val Ser Leu Asp Val Gly Lys Lys Glu Tyr Leu Ile
            100                 105                 110

Ala Gly Lys Ala Glu Gly Asp Gly Lys Met His Ile Thr Leu Cys Asp
            115                 120                 125

Phe Ile Val Pro Trp Asp Thr Leu Ser Thr Thr Gln Lys Lys Ser Leu
130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
            180                 185                 190

Cys Ile Lys Arg Ser Asp Gly Ser Cys Ala Trp Tyr Arg Gly Ala Ala
            195                 200                 205

Pro Pro Lys Gln Glu Phe Leu Asp Ile Glu Asp Pro
210                 215                 220

<210> SEQ ID NO 3
<211> LENGTH: 211
<212> TYPE: PRT
<213> ORGANISM: Homo sapiens

<400> SEQUENCE: 3

Met Thr Pro Trp Leu Gly Leu Ile Val Leu Leu Gly Ser Trp Ser Leu
 1               5                  10                  15

Gly Asp Trp Gly Ala Glu Ala Cys Thr Cys Ser Pro Ser His Pro Gln
                 20                  25                  30

Asp Ala Phe Cys Asn Ser Asp Ile Val Ile Arg Ala Lys Val Val Gly
             35                  40                  45

Lys Lys Leu Val Lys Glu Gly Pro Phe Gly Thr Leu Val Tyr Thr Ile
 50                  55                  60

Lys Gln Met Lys Met Tyr Arg Gly Phe Thr Lys Met Pro His Val Gln
 65                  70                  75                  80

Tyr Ile His Thr Glu Ala Ser Glu Ser Leu Cys Gly Leu Lys Leu Glu
                 85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
            115                 120                 125

Leu Ser Gln Arg Lys Gly Leu Asn Tyr Arg Tyr His Leu Gly Cys Asn
130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
            195                 200                 205

Thr Asp Pro
```

-continued

210

<210> SEQ ID NO 4
<211> LENGTH: 224
<212> TYPE: PRT
<213> ORGANISM: Homo sapiens

<400> SEQUENCE: 4

| Met | Pro | Gly | Ser | Pro | Arg | Pro | Ala | Pro | Ser | Trp | Val | Leu | Leu | Leu | Arg |
| 1 | | | | 5 | | | | | 10 | | | | | 15 | |

| Leu | Leu | Ala | Leu | Leu | Arg | Pro | Pro | Gly | Leu | Gly | Glu | Ala | Cys | Ser | Cys |
| | | | 20 | | | | | 25 | | | | | 30 | | |

| Ala | Pro | Ala | His | Pro | Gln | Gln | His | Ile | Cys | His | Ser | Ala | Leu | Val | Ile |
| | | 35 | | | | | 40 | | | | | 45 | | | |

| Arg | Ala | Lys | Ile | Ser | Ser | Glu | Lys | Val | Val | Pro | Ser | Ala | Asp | Pro |
| | 50 | | | | | 55 | | | | | 60 | | | |

| Ala | Asp | Thr | Glu | Lys | Met | Leu | Arg | Tyr | Glu | Ile | Lys | Gln | Ile | Lys | Met |
| 65 | | | | | 70 | | | | | 75 | | | | | 80 |

| Phe | Lys | Gly | Phe | Glu | Lys | Val | Lys | Asp | Val | Gln | Tyr | Ile | Tyr | Thr | Pro |
| | | | | 85 | | | | | 90 | | | | | 95 | |

| Phe | Asp | Ser | Ser | Leu | Cys | Gly | Val | Lys | Leu | Glu | Ala | Asn | Ser | Gln | Lys |
| | | | 100 | | | | | 105 | | | | | 110 | | |

| Gln | Tyr | Leu | Leu | Thr | Gly | Gln | Val | Leu | Ser | Asp | Gly | Lys | Val | Phe | Ile |
| | | 115 | | | | | 120 | | | | | 125 | | | |

| His | Leu | Cys | Asn | Tyr | Ile | Glu | Pro | Trp | Glu | Asp | Leu | Ser | Leu | Val | Gln |
| | 130 | | | | | 135 | | | | | 140 | | | | |

| Arg | Glu | Ser | Leu | Asn | His | His | Tyr | His | Leu | Asn | Cys | Gly | Cys | Gln | Ile |
| 145 | | | | | 150 | | | | | 155 | | | | | 160 |

| Thr | Thr | Cys | Tyr | Thr | Val | Pro | Cys | Thr | Ile | Ser | Ala | Pro | Asn | Glu | Cys |
| | | | | 165 | | | | | 170 | | | | | 175 | |

| Leu | Trp | Thr | Asp | Trp | Leu | Leu | Glu | Arg | Lys | Leu | Tyr | Gly | Tyr | Gln | Ala |
| | | | 180 | | | | | 185 | | | | | 190 | | |

| Gln | His | Tyr | Val | Cys | Met | Lys | His | Val | Asp | Gly | Thr | Cys | Ser | Trp | Tyr |
| | | 195 | | | | | 200 | | | | | 205 | | | |

| Arg | Gly | His | Leu | Pro | Leu | Arg | Lys | Glu | Phe | Val | Asp | Ile | Val | Gln | Pro |
| 210 | | | | | 215 | | | | | 220 | | | | | |

<210> SEQ ID NO 5
<211> LENGTH: 108
<212> TYPE: PRT
<213> ORGANISM: Artificial Sequence
<220> FEATURE:
<223> OTHER INFORMATION: A polypeptide inhibitor.

<400> SEQUENCE: 5

| Met | Cys | Ser | Cys | Ser | Pro | Val | His | Pro | Gln | Gln | Ala | Phe | Ser | Asn | Ala |
| 1 | | | | 5 | | | | | 10 | | | | | 15 | |

| Asp | Val | Val | Ile | Arg | Ala | Lys | Ala | Val | Ser | Glu | Lys | Glu | Val | Asp | Ser |
| | | | 20 | | | | | 25 | | | | | 30 | | |

| Gly | Asn | Asp | Ile | Tyr | Gly | Asn | Pro | Ile | Lys | Arg | Ile | Gln | Tyr | Glu | Ile |
| | | 35 | | | | | 40 | | | | | 45 | | | |

| Lys | Gln | Ile | Lys | Met | Phe | Lys | Gly | Pro | Glu | Lys | Asp | Ile | Glu | Phe | Ile |
| | 50 | | | | | 55 | | | | | 60 | | | | |

| Tyr | Thr | Ala | Pro | Ser | Ser | Ala | Val | Cys | Gly | Val | Ser | Leu | Asp | Val | Gly |
| 65 | | | | | 70 | | | | | 75 | | | | | 80 |

| Gly | Lys | Lys | Glu | Tyr | Cys | Ile | Ala | Gly | Lys | Ala | Glu | Gly | Asp | Gly | Lys |
| | | | | 85 | | | | | 90 | | | | | 95 | |

Met His Ile Thr Leu Cys Asp Phe Ile Cys Pro Trp
            100                 105

<210> SEQ ID NO 6
<211> LENGTH: 339
<212> TYPE: DNA
<213> ORGANISM: Artificial Sequence
<220> FEATURE:
<223> OTHER INFORMATION: Nucleic acid sequence of polypeptide inhibitor.

<400> SEQUENCE: 6
atgtgcagct gcagcccggt gcatccgcag caggcgttta gcaacgcgga tgtggtgatt      60
cgcgcgaaag cggtgagcga aaagaagtc gatagcggca acgatattta tggcaacccg     120
attaaacgca ttcagtatga aattaaacag attaaaatgt ttaaaggccc ggaaaaagat     180
attgaattta tttataccgc gccgagcagc gcggtgtgcg gcgtgagcct ggatgtgggc     240
ggcaaaaaag aatattgcat tgcgggcaaa gcggaaggcg atggcaaaat gcatattacc     300
ctgtgcgatt ttatttgccc gtggtagaag cttatagac                            339

<210> SEQ ID NO 7
<211> LENGTH: 108
<212> TYPE: PRT
<213> ORGANISM: Artificial Sequence
<220> FEATURE:
<223> OTHER INFORMATION: A polypeptide inhibitor.
<220> FEATURE:
<221> NAME/KEY: SITE
<222> LOCATION: 7, 12, 16, 18-20, 22, 24-25, 30, 36, 41, 44, 48, 51, 61,
      64, 67, 71-72, 75, 77, 79, 87-88, 91, 99, 101, 105
<223> OTHER INFORMATION: Xaa = any aliphatic amino acid, alanine,
      valine, isoleucine or leucine
<220> FEATURE:
<221> NAME/KEY: SITE
<222> LOCATION: 17, 27, 29, 31, 35, 47, 58, 60, 62, 78, 84, 92, 94, 103
<223> OTHER INFORMATION: Xaa = any acidic amino acid, aspartic acid or
      glutamic acid
<220> FEATURE:
<221> NAME/KEY: SITE
<222> LOCATION: 2, 4, 73, 86, 102, 106
<223> OTHER INFORMATION: Xaa = any cysteine-like amino acid or cysteine
<220> FEATURE:
<221> NAME/KEY: SITE
<222> LOCATION: 21, 23, 28, 42-43, 49, 52, 55, 59, 82-83, 90, 96
<223> OTHER INFORMATION: Xaa = any basic amino acid, lysine or arginine
<220> FEATURE:
<221> NAME/KEY: SITE
<222> LOCATION: 13, 54, 63, 104
<223> OTHER INFORMATION: Xaa = any aromatic amino acid or phenylalanine
<220> FEATURE:
<221> NAME/KEY: SITE
<222> LOCATION: (1)...(1)
<223> OTHER INFORMATION: Xaa = any apolar amino acid, methionine, or no
      amino acid
<220> FEATURE:
<221> NAME/KEY: SITE
<222> LOCATION: (53)...(53)
<223> OTHER INFORMATION: Xaa = any apolar amino acid or methionine
<220> FEATURE:
<221> NAME/KEY: SITE
<222> LOCATION: (97)...(97)
<223> OTHER INFORMATION: Xaa = any apolar amino acid or methionine
<220> FEATURE:
<221> NAME/KEY: SITE
<222> LOCATION: (6)...(6)
<223> OTHER INFORMATION: Xaa = any apolar amino acid or proline
<220> FEATURE:
<221> NAME/KEY: SITE
<222> LOCATION: (9)...(9)
<223> OTHER INFORMATION: Xaa = any apolar amino acid or proline
<220> FEATURE:
<221> NAME/KEY: SITE -continued

```
<222> LOCATION: (33)...(33)
<223> OTHER INFORMATION: Xaa = any apolar amino acid or glycine
<220> FEATURE:
<221> NAME/KEY: SITE
<222> LOCATION: (38)...(38)
<223> OTHER INFORMATION: Xaa = any apolar amino acid or glycine
<220> FEATURE:
<221> NAME/KEY: SITE
<222> LOCATION: (40)...(40)
<223> OTHER INFORMATION: Xaa = any apolar amino acid or proline
<220> FEATURE:
<221> NAME/KEY: SITE
<222> LOCATION: (56)...(56)
<223> OTHER INFORMATION: Xaa = any apolar amino acid or glycine
<220> FEATURE:
<221> NAME/KEY: SITE
<222> LOCATION: (57)...(57)
<223> OTHER INFORMATION: Xaa = any apolar amino acid or proline
<220> FEATURE:
<221> NAME/KEY: SITE
<222> LOCATION: (68)...(68)
<223> OTHER INFORMATION: Xaa = any apolar amino acid or proline
<220> FEATURE:
<221> NAME/KEY: SITE
<222> LOCATION: (74)...(74)
<223> OTHER INFORMATION: Xaa = any apolar amino acid or glycine
<220> FEATURE:
<221> NAME/KEY: SITE
<222> LOCATION: (80)...(80)
<223> OTHER INFORMATION: Xaa = any apolar amino acid or glycine
<220> FEATURE:
<221> NAME/KEY: SITE
<222> LOCATION: (81)...(81)
<223> OTHER INFORMATION: Xaa = any apolar amino acid or glycine
<220> FEATURE:
<221> NAME/KEY: SITE
<222> LOCATION: (89)...(89)
<223> OTHER INFORMATION: Xaa = any apolar amino acid or glycine
<220> FEATURE:
<221> NAME/KEY: SITE
<222> LOCATION: (93)...(93)
<223> OTHER INFORMATION: Xaa = any apolar amino acid or glycine
<220> FEATURE:
<221> NAME/KEY: SITE
<222> LOCATION: (95)...(95)
<223> OTHER INFORMATION: Xaa = any apolar amino acid or glycine
<220> FEATURE:
<221> NAME/KEY: SITE
<222> LOCATION: (107)...(107)
<223> OTHER INFORMATION: Xaa = any apolar amino acid or proline
<220> FEATURE:
<221> NAME/KEY: SITE
<222> LOCATION: (3)...(3)
<223> OTHER INFORMATION: Xaa = any polar amino acid, serine or threonine
<220> FEATURE:
<221> NAME/KEY: SITE
<222> LOCATION: (5)...(5)
<223> OTHER INFORMATION: Xaa = any polar amino acid, serine or threonine
<220> FEATURE:
<221> NAME/KEY: SITE
<222> LOCATION: (10)...(10)
<223> OTHER INFORMATION: Xaa = any polar amino acid, asparagine, or
      glutamine
<220> FEATURE:
<221> NAME/KEY: SITE
<222> LOCATION: (11)...(11)
<223> OTHER INFORMATION: Xaa = any polar amino acid, asparagine, or
      glutamine
<220> FEATURE:
<221> NAME/KEY: SITE
<222> LOCATION: (14)...(14)
<223> OTHER INFORMATION: Xaa = any polar amino acid, serine or threonine
<220> FEATURE:
<221> NAME/KEY: SITE
<222> LOCATION: (15)...(15)
<223> OTHER INFORMATION: Xaa = any polar amino acid, asparagine, or
      glutamine
<220> FEATURE:
<221> NAME/KEY: SITE
```

```
<222> LOCATION: (26)...(26)
<223> OTHER INFORMATION: Xaa = any polar amino acid, serine or threonine
<220> FEATURE:
<221> NAME/KEY: SITE
<222> LOCATION: (32)...(32)
<223> OTHER INFORMATION: Xaa = any polar amino acid, serine or threonine
<220> FEATURE:
<221> NAME/KEY: SITE
<222> LOCATION: (34)...(34)
<223> OTHER INFORMATION: Xaa = any polar amino acid, asparagine, or
      glutamine
<220> FEATURE:
<221> NAME/KEY: SITE
<222> LOCATION: (37)...(37)
<223> OTHER INFORMATION: Xaa = any polar amino acid or tyrosine
<220> FEATURE:
<221> NAME/KEY: SITE
<222> LOCATION: (39)...(39)
<223> OTHER INFORMATION: Xaa = any polar amino acid, asparagine, or
      glutamine
<220> FEATURE:
<221> NAME/KEY: SITE
<222> LOCATION: (45)...(45)
<223> OTHER INFORMATION: Xaa = any polar amino acid, asparagine, or
      glutamine
<220> FEATURE:
<221> NAME/KEY: SITE
<222> LOCATION: (46)...(46)
<223> OTHER INFORMATION: Xaa = any polar amino acid or tyrosine
<220> FEATURE:
<221> NAME/KEY: SITE
<222> LOCATION: (50)...(50)
<223> OTHER INFORMATION: Xaa = any polar amino acid, asparagine, or
      glutamine
<220> FEATURE:
<221> NAME/KEY: SITE
<222> LOCATION: (65)...(65)
<223> OTHER INFORMATION: Xaa = any polar amino acid or tyrosine
<220> FEATURE:
<221> NAME/KEY: SITE
<222> LOCATION: (66)...(66)
<223> OTHER INFORMATION: Xaa = any polar amino acid, serine or threonine
<220> FEATURE:
<221> NAME/KEY: SITE
<222> LOCATION: (69)...(69)
<223> OTHER INFORMATION: Xaa = any polar amino acid, serine or threonine
<220> FEATURE:
<221> NAME/KEY: SITE
<222> LOCATION: (70)...(70)
<223> OTHER INFORMATION: Xaa = any polar amino acid, serine or threonine
<220> FEATURE:
<221> NAME/KEY: SITE
<222> LOCATION: (76)...(76)
<223> OTHER INFORMATION: Xaa = any polar amino acid, serine or threonine
<220> FEATURE:
<221> NAME/KEY: SITE
<222> LOCATION: (85)...(85)
<223> OTHER INFORMATION: Xaa = any polar amino acid or tyrosine
<220> FEATURE:
<221> NAME/KEY: SITE
<222> LOCATION: (100)...(100)
<223> OTHER INFORMATION: Xaa = any polar amino acid, serine or threonine
<220> FEATURE:
<221> NAME/KEY: SITE
<222> LOCATION: (8)...(8)
<223> OTHER INFORMATION: Xaa = any basic amino acid or histidine
<220> FEATURE:
<221> NAME/KEY: SITE
<222> LOCATION: (98)...(98)
<223> OTHER INFORMATION: Xaa = any basic amino acid or histidine
<220> FEATURE:
<221> NAME/KEY: SITE
<222> LOCATION: (108)...(108)
<223> OTHER INFORMATION: Xaa = tryptophan

<400> SEQUENCE: 7

Xaa Xaa Xaa Xaa Xaa Xaa Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa Xaa Xaa Xaa Xaa Xaa Xaa
              20                  25                  30

Xaa Xaa Xaa Xaa Xaa Xaa Xaa Xaa Xaa Xaa Xaa Xaa Xaa Xaa Xaa
          35                  40                  45

Xaa Xaa Xaa Xaa Xaa Xaa Xaa Xaa Xaa Xaa Xaa Xaa Xaa Xaa Xaa
      50                  55                  60

Xaa Xaa Xaa Xaa Xaa Xaa Xaa Xaa Xaa Xaa Xaa Xaa Xaa Xaa Xaa
  65                  70                  75                  80

Xaa Xaa Xaa Xaa Xaa Xaa Xaa Xaa Xaa Xaa Xaa Xaa Xaa Xaa Xaa
                  85                  90                  95

Xaa Xaa Xaa Xaa Xaa Xaa Xaa Xaa Xaa Xaa Xaa Xaa
              100                 105
```

```
<210> SEQ ID NO 8
<211> LENGTH: 70
<212> TYPE: DNA
<213> ORGANISM: Artificial Sequence
<220> FEATURE:
<223> OTHER INFORMATION: A primer.

<400> SEQUENCE: 8
atgtgcagct gcagcccggt gcatccgcag caggcgttta gcaacgcgga tgtggtgatt      60
cgcgcgaaag                                                              70

<210> SEQ ID NO 9
<211> LENGTH: 70
<212> TYPE: DNA
<213> ORGANISM: Artificial Sequence
<220> FEATURE:
<223> OTHER INFORMATION: A primer.

<400> SEQUENCE: 9
cggtgagcga aaagaagtc gatagcggca acgatattta tggcaacccg attaaacgca       60
ttcagtatga                                                              70

<210> SEQ ID NO 10
<211> LENGTH: 70
<212> TYPE: DNA
<213> ORGANISM: Artificial Sequence
<220> FEATURE:
<223> OTHER INFORMATION: A primer.

<400> SEQUENCE: 10
aattaaacag attaaaatgt ttaaaggccc ggaaaaagat attgaattta tttataccgc      60
gccgagcagc                                                              70

<210> SEQ ID NO 11
<211> LENGTH: 70
<212> TYPE: DNA
<213> ORGANISM: Artificial Sequence
<220> FEATURE:
<223> OTHER INFORMATION: A primer.

<400> SEQUENCE: 11
gcggtgtgcg gcgtgagcct ggatgtgggc ggcaaaaaag aatattgcat tgcgggcaaa      60
gcggaaggcg                                                              70

<210> SEQ ID NO 12
<211> LENGTH: 59
<212> TYPE: DNA
```

```
<213> ORGANISM: Artificial Sequence
<220> FEATURE:
<223> OTHER INFORMATION: A primer.

<400> SEQUENCE: 12
atggcaaaat gcatattacc ctgtgcgatt ttatttgccc gtggtagaag cttatagac         59

<210> SEQ ID NO 13
<211> LENGTH: 80
<212> TYPE: DNA
<213> ORGANISM: Artificial Sequence
<220> FEATURE:
<223> OTHER INFORMATION: A primer.

<400> SEQUENCE: 13
tcgctcaccg ctttcgcgcg aatcaccaca tccgcgttgc taaacgcctg ctgcggatgc         60
accgggctgc agctgcacat                                                     80

<210> SEQ ID NO 14
<211> LENGTH: 70
<212> TYPE: DNA
<213> ORGANISM: Artificial Sequence
<220> FEATURE:
<223> OTHER INFORMATION: A primer.

<400> SEQUENCE: 14
ctgtttaatt tcatactgaa tgcgtttaat cgggttgcca taaatatcgt tgccgctatc         60
gacttctttt                                                                70

<210> SEQ ID NO 15
<211> LENGTH: 70
<212> TYPE: DNA
<213> ORGANISM: Artificial Sequence
<220> FEATURE:
<223> OTHER INFORMATION: A primer.

<400> SEQUENCE: 15
cgcacaccgc gctgctcggc gcggtataaa taaattcaat atcttttcc gggcctttaa          60 acattttaat                                                                70

<210> SEQ ID NO 16
<211> LENGTH: 70
<212> TYPE: DNA
<213> ORGANISM: Artificial Sequence
<220> FEATURE:
<223> OTHER INFORMATION: A primer.

<400> SEQUENCE: 16
attttgccat cgccttccgc tttgcccgca atgcaatatt cttttttgcc gcccacatcc         60
aggctcacgc                                                                70

<210> SEQ ID NO 17
<211> LENGTH: 49
<212> TYPE: DNA
<213> ORGANISM: Artificial Sequence
<220> FEATURE:
<223> OTHER INFORMATION: A primer.

<400> SEQUENCE: 17
gtctataagc ttctaccacg ggcaaataaa atcgcacagg gtaatatgc                     49

<210> SEQ ID NO 18
<211> LENGTH: 20
```

```
<212> TYPE: DNA
<213> ORGANISM: Artificial Sequence
<220> FEATURE:
<223> OTHER INFORMATION: A primer.

<400> SEQUENCE: 18
atgtgcagct gcagcccggt                                                    20

<210> SEQ ID NO 19
<211> LENGTH: 20
<212> TYPE: DNA
<213> ORGANISM: Artificial Sequence
<220> FEATURE:
<223> OTHER INFORMATION: A primer.

<400> SEQUENCE: 19
gtctataagc ttctaccacg                                                    20

<210> SEQ ID NO 20
<211> LENGTH: 107
<212> TYPE: PRT
<213> ORGANISM: Artificial Sequence
<220> FEATURE:
<223> OTHER INFORMATION: A polypeptide inhibitor.

<400> SEQUENCE: 20

Cys Ser Cys Ser Pro Val His Pro Gln Gln Ala Phe Ser Asn Ala Asp
 1               5                  10                  15

Val Val Ile Arg Ala Lys Ala Val Ser Glu Lys Glu Val Asp Ser Gly
             20                  25                  30

Asn Asp Ile Tyr Gly Asn Pro Ile Lys Arg Ile Gln Tyr Glu Ile Lys
         35                  40                  45

Gln Ile Lys Met Phe Lys Gly Pro Glu Lys Asp Ile Glu Phe Ile Tyr
     50                  55                  60

Thr Ala Pro Ser Ser Ala Val Cys Gly Val Ser Leu Asp Val Gly Gly
 65                  70                  75                  80

Lys Lys Glu Tyr Cys Ile Ala Gly Lys Ala Glu Gly Asp Gly Lys Met
                 85                  90                  95

His Ile Thr Leu Cys Asp Phe Ile Cys Pro Trp
            100                 105

<210> SEQ ID NO 21
<211> LENGTH: 108
<212> TYPE: PRT
<213> ORGANISM: Artificial Sequence
<220> FEATURE:
<223> OTHER INFORMATION: A polypeptide inhibitor.
<220> FEATURE:
<221> NAME/KEY: SITE
<222> LOCATION: 7, 12, 16, 18-20, 22, 24-25, 30, 36, 41, 44, 48, 51, 61,
      64, 67, 71-72, 75, 77, 79, 87-88, 91, 99, 101, 105
<223> OTHER INFORMATION: Xaa = alanine, valine, isoleucine, or leucine
<220> FEATURE:
<221> NAME/KEY: SITE
<222> LOCATION: 17, 27, 29, 31, 35, 47, 58, 60, 62, 78, 84, 92, 94, 103
<223> OTHER INFORMATION: Xaa = aspartic acid or glutamic acid
<220> FEATURE:
<221> NAME/KEY: SITE
<222> LOCATION: 3, 5, 14, 26, 32, 66, 69, 70, 76, 100
<223> OTHER INFORMATION: Xaa = serine or threonine
<220> FEATURE:
<221> NAME/KEY: SITE
<222> LOCATION: 21, 23, 28, 42-43, 49, 52, 55, 59, 82-83, 90, 96
<223> OTHER INFORMATION: Xaa = lysine or arginine
<220> FEATURE:
<221> NAME/KEY: SITE
<222> LOCATION: 33, 38, 56, 74, 80, 81, 89, 93, 95
```

```
<223> OTHER INFORMATION: Xaa = glycine
<220> FEATURE:
<221> NAME/KEY: SITE
<222> LOCATION: (1)...(1)
<223> OTHER INFORMATION: Xaa = methionine
<220> FEATURE:
<221> NAME/KEY: SITE
<222> LOCATION: (53)...(53)
<223> OTHER INFORMATION: Xaa = methionine
<220> FEATURE:
<221> NAME/KEY: SITE
<222> LOCATION: (97)...(97)
<223> OTHER INFORMATION: Xaa = methionine
<220> FEATURE:
<221> NAME/KEY: SITE
<222> LOCATION: (2)...(2)
<223> OTHER INFORMATION: Xaa = cysteine
<220> FEATURE:
<221> NAME/KEY: SITE
<222> LOCATION: (4)...(4)
<223> OTHER INFORMATION: Xaa = cysteine
<220> FEATURE:
<221> NAME/KEY: SITE
<222> LOCATION: (73)...(73)
<223> OTHER INFORMATION: Xaa = cysteine
<220> FEATURE:
<221> NAME/KEY: SITE
<222> LOCATION: (86)...(86)
<223> OTHER INFORMATION: Xaa = cysteine
<220> FEATURE:
<221> NAME/KEY: SITE
<222> LOCATION: (102)...(102)
<223> OTHER INFORMATION: Xaa = cysteine
<220> FEATURE:
<221> NAME/KEY: SITE
<222> LOCATION: (106)...(106)
<223> OTHER INFORMATION: Xaa = cysteine
<220> FEATURE:
<221> NAME/KEY: SITE
<222> LOCATION: (8)...(8)
<223> OTHER INFORMATION: Xaa = histidine
<220> FEATURE:
<221> NAME/KEY: SITE
<222> LOCATION: (98)...(98)
<223> OTHER INFORMATION: Xaa = histidine
<220> FEATURE:
<221> NAME/KEY: SITE
<222> LOCATION: (6)...(6)
<223> OTHER INFORMATION: Xaa = proline
<220> FEATURE:
<221> NAME/KEY: SITE
<222> LOCATION: (9)...(9)
<223> OTHER INFORMATION: Xaa = proline
<220> FEATURE:
<221> NAME/KEY: SITE
<222> LOCATION: (40)...(40)
<223> OTHER INFORMATION: Xaa = proline
<220> FEATURE:
<221> NAME/KEY: SITE
<222> LOCATION: (57)...(57)
<223> OTHER INFORMATION: Xaa = proline
<220> FEATURE:
<221> NAME/KEY: SITE
<222> LOCATION: (68)...(68)
<223> OTHER INFORMATION: Xaa = proline
<220> FEATURE:
<221> NAME/KEY: SITE
<222> LOCATION: (107)...(107)
<223> OTHER INFORMATION: Xaa = proline
<220> FEATURE:
<221> NAME/KEY: SITE
<222> LOCATION: (10)...(10)
<223> OTHER INFORMATION: Xaa = asparagine or glutamine
<220> FEATURE:
<221> NAME/KEY: SITE
<222> LOCATION: (11)...(11)
<223> OTHER INFORMATION: Xaa = asparagine or glutamine
<220> FEATURE:
<221> NAME/KEY: SITE
```

```
<222> LOCATION: (15)...(15)
<223> OTHER INFORMATION: Xaa = asparagine or glutamine
<220> FEATURE:
<221> NAME/KEY: SITE
<222> LOCATION: (34)...(34)
<223> OTHER INFORMATION: Xaa = asparagine or glutamine
<220> FEATURE:
<221> NAME/KEY: SITE
<222> LOCATION: (39)...(39)
<223> OTHER INFORMATION: Xaa = asparagine or glutamine
<220> FEATURE:
<221> NAME/KEY: SITE
<222> LOCATION: (45)...(45)
<223> OTHER INFORMATION: Xaa = asparagine or glutamine
<220> FEATURE:
<221> NAME/KEY: SITE
<222> LOCATION: (50)...(50)
<223> OTHER INFORMATION: Xaa = asparagine or glutamine
<220> FEATURE:
<221> NAME/KEY: SITE
<222> LOCATION: (13)...(13)
<223> OTHER INFORMATION: Xaa = phenylalanine
<220> FEATURE:
<221> NAME/KEY: SITE
<222> LOCATION: (54)...(54)
<223> OTHER INFORMATION: Xaa = phenylalanine
<220> FEATURE:
<221> NAME/KEY: SITE
<222> LOCATION: (63)...(63)
<223> OTHER INFORMATION: Xaa = phenylalanine
<220> FEATURE:
<221> NAME/KEY: SITE
<222> LOCATION: (104)...(104)
<223> OTHER INFORMATION: Xaa = phenylalanine
<220> FEATURE:
<221> NAME/KEY: SITE
<222> LOCATION: (37)...(37)
<223> OTHER INFORMATION: Xaa = tyrosine
<220> FEATURE:
<221> NAME/KEY: SITE
<222> LOCATION: (46)...(46)
<223> OTHER INFORMATION: Xaa = tyrosine
<220> FEATURE:
<221> NAME/KEY: SITE
<222> LOCATION: (65)...(65)
<223> OTHER INFORMATION: Xaa = tyrosine
<220> FEATURE:
<221> NAME/KEY: SITE
<222> LOCATION: (85)...(85)
<223> OTHER INFORMATION: Xaa = tyrosine
<220> FEATURE:
<221> NAME/KEY: SITE
<222> LOCATION: (108)...(108)
<223> OTHER INFORMATION: Xaa = tyrosine

<400> SEQUENCE: 21

Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Xaa
            100                 105
```

WOUND CARE COMPOSITIONS

FIELD OF THE INVENTION

The present invention relates generally to the field of wound healing and to the repair and maintenance of healthy skin.

BACKGROUND OF THE INVENTION

One major reason that chronic wounds do not heal is that a class of proteinases destroys the newly formed wound bed (Vaalamo et al., 1997; Weckroth et al., 1996; DiColandrea et al., 1998; Moses et al., 1996). These matrix metalloproteinases (MMPs) are normally prevented from destroying the wound bed by the action of four Tissue Inhibitors of MetalloProteinase (TIMPs1–4) that form very specific inhibitory complexes with the MMPs (e.g., Olson et al., 1997; Taylor et al., 1996; Howard et al., 1991). That is, each TIMP only inhibits a specific subset of MMPs. In chronic wounds the ratio of MMP to TIMP is high, such that most of the MMPs are uninhibited (Vaalamo et al., 1996; Saarialho-Kere, 1998). In fact, with elevated protease levels, the TIMP molecules themselves can be hydrolyzed. There is no naturally occurring TIMP molecule that singly inhibits all types of MMPs.

Hence, further approaches are needed to optimize inhibition of matrix metalloproteinases and to improve wound healing.

SUMMARY OF THE INVENTION

The invention provides polypeptides that can inhibit matrix metalloproteinases. Examples of the polypeptides provided by the invention include isolated polypeptides comprising SEQ ID NO:5, SEQ ID NO:7, SEQ ID NO:20 or SEQ ID NO:21. Also provided are isolated nucleic acids that encode a polypeptide of the invention, for example, nucleic acids that encode a polypeptide comprising SEQ ID NO:5, SEQ ID NO:7, SEQ ID NO:20 or SEQ ID NO:21. Examples of such isolated nucleic acids include a nucleic acid that comprises SEQ ID NO:6 and isolated nucleic acids that can hybridize under stringent hybridization conditions to a nucleic acid comprising SEQ ID NO:6.

The polypeptides of the invention are useful for treating wounds, including chronic wounds. Hence, the invention provides a composition that comprises a therapeutically effective amount of polypeptide inhibitor comprising SEQ ID NO:5, SEQ ID NO:7, SEQ ID NO:20 or SEQ ID NO:21 and a pharmaceutically acceptable carrier. The composition can, for example, be provided in the form of a lotion, gel or cream. Alternatively, the polypeptides can be provided in a wound dressing. Such a wound dressing can include a polypeptide comprising SEQ ID NO:5, SEQ ID NO:7, SEQ ID NO:20 or SEQ ID NO:21 and a pharmaceutically acceptable carrier.

The invention further provides a method for treating a wound that comprises administering a therapeutically effective amount of a polypeptide comprising SEQ ID NO:5, SEQ ID NO:7, SEQ ID NO:20 or SEQ ID NO:21 to the wound.

The polypeptide inhibitors of the invention have many useful properties. For example, these polypeptide inhibitors can promote wound healing, prevent scarring, improve skin tone, or stimulate the development of a smooth, healthy skin. Moreover, they are stable in mammalian serum or plasma.

The polypeptide inhibitors in the compositions, dressings and methods of the invention can inhibit proteinase activity of any one of matrix metalloproteinase-1, matrix metalloproteinase-2, matrix metalloproteinase-3, matrix metalloproteinase-4, matrix metalloproteinase-5, matrix metalloproteinase-6, matrix metalloproteinase-7, matrix metalloproteinase-8, and matrix metalloproteinase-9, matrix metalloproteinase-10, matrix metalloproteinase-11, matrix metalloproteinase-12, or matrix metalloproteinase-13. In some embodiments, the polypeptide inhibitor can inhibit more than one of these matrix metalloproteinases.

DESCRIPTION OF THE FIGURES

FIG. 2A provides a solid CPK space-filled model showing the overall three dimensionality of the protein. Note the TIMP-2 like extension (upper left of the molecule) that rises from the matrix metalloproteinase-binding surface. FIG. 2B provides the same view as in 2A, only the display illustrates the secondary structural elements of the protein. Beta strand structures that form the central beta barrel motif are shown in light gray, loops and turns are in white, and the single alpha helix is shown in dark gray. The protein is shown as a trace through the alpha carbon positions. Both illustrations were made using Rasmol.

DETAILED DESCRIPTION OF THE INVENTION

Figure 1:
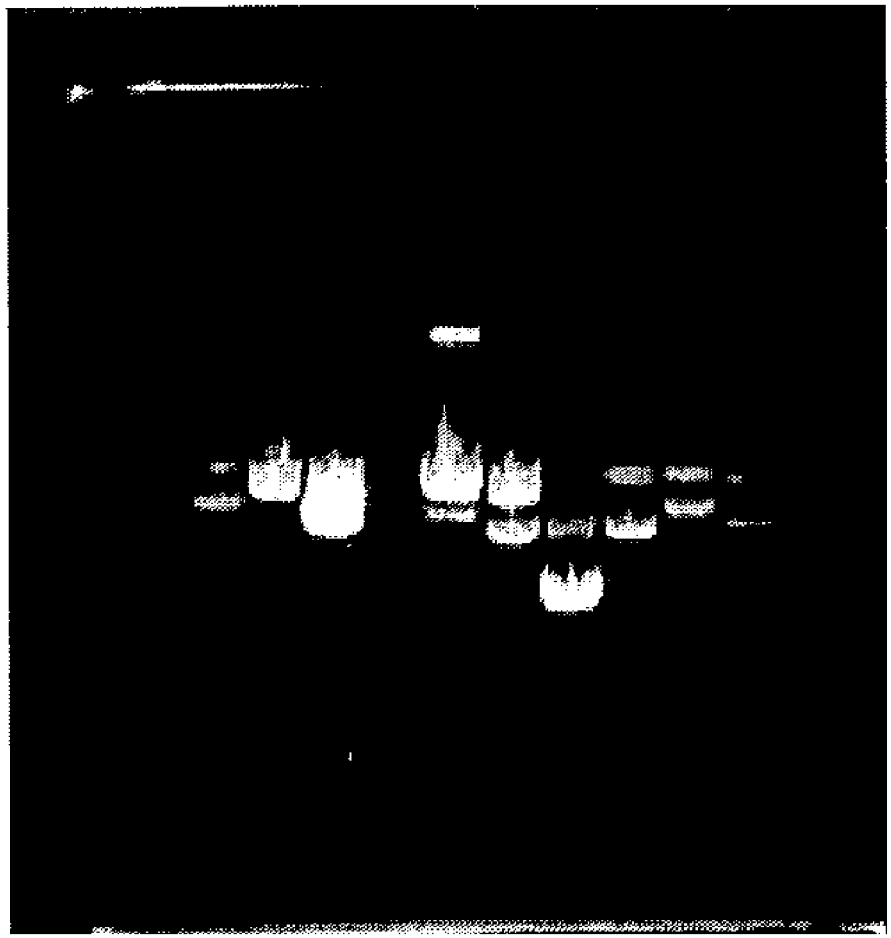
FIG. 1 provides a photocopy of a 1.5% agarose gel showing DNA from recombinant clones. Ligated gene-expression vector constructs were transformed into JM109, grown on LB plates supplemented with ampicillin. Individual colonies were picked into liquid media and plasmid was purified from these cultures by mini-prep. Lanes 3, 6, and 8 contained DNA with a size corresponding to a plasmid having a SEQ ID NO:6 insert. These plasmids were further characterized by restriction digest (not shown). The plasmid from lane 3 was picked for protein expression analysis.

The present invention provides inhibitors of matrix metalloproteinases that are useful for promoting wound healing. In general, the present inhibitors and compositions promote wound healing, prevent scarring, improve skin tone and stimulate the development of a smooth, healthy skin.

According to the invention, a polypeptide with a sufficient degree of amino acid sequence identity to regions of the four Tissue Inhibitors of MetalloProteinase (TIMPs1–4) can form an inhibitory complex with a variety of matrix metalloproteinases. Administration of such a polypeptide inhibits matrix metalloproteinases and diminishes the rate of extracellular matrix destruction in wounds. Hence, such a polypeptide inhibitor can provide a faster rate of wound healing.

Most inhibition strategies involve preventing enzymatic activity of matrix metalloproteinases with organic small molecules. These compounds are often toxic to the body and are not naturally occurring molecules. Use of natural polypeptides to inhibit matrix metalloproteinases provides a high degree of proteinase control without toxic side effects. Unlike small molecule inhibition strategies, the polypeptides of the invention can be used to inhibit activation of individual or all matrix metalloproteinase classes simultaneously. The polypeptides can be freely introduced onto the skin, into the wound environment, or they can be tethered to, or delivered by, a skin covering or wound dressing.

The invention provides a high degree of control over the level of proteinase activity for healing chronic wounds. For example, as some amount of proteinase level is required during chronic wound healing (Agren et al., 1999), one of skill in the art may choose to only partially inhibit proteinase activity. By modulating the type and amount of inhibitor polypeptide applied, the degree of matrix metalloproteinase inhibition can be controlled.

Polypeptide Inhibitors

According to the present invention, polypeptides having sequences related to TIMPs are useful for wound healing and for promoting development of healthy skin. As provided herein, the term polypeptide is used synonymously with the term protein. The polypeptides provided by the invention inhibit the activity of many types of matrix metalloproteinases. However, the polypeptide inhibitors are smaller and more stable than naturally occurring TIMP polypeptides. Moreover, the sequence of the present polypeptide inhibitors can be modulated to optimize their binding properties, for example, the polypeptide sequence can be modulated to that it inhibits a broad spectrum of metalloproteinases or the sequence can be changed so that only one or a few metalloproteinases are inhibited.

For example, a human TIMP-1 can have the following amino acid sequence (SEQ ID NO:1).

```
  1 MAPFEPLASG ILLLLWLIAP SRACTCVPPH PQTAFCNSDL
 41 VIRAKFVGTP EVNQTTLYQR YEIKMTKMYK GFQALGDAAD
 81 IRFVYTPAME SVCGYFHRSH NRSEEFLIAG KLQDGLLHIT
121 TCSFVAPWNS LSLAQRRGFT KTYTVGCEEC TVFPCLSIPC
161 KLQSGTHCLW TDQLLQGSEK GFQSRHLACL PREPGLCTWQ
201 SLRSQIA
```

See Docherty et al., Sequence of human tissue inhibitor of metalloproteinases and its identity to erythroid-potentiating activity, Nature 318 (6041), 66–69 (1985).

A human TIMP-2 can have the following amino acid sequence (SEQ ID NO:2).

```
  1 MGAAARTLRL ALGLLLLATL LRPADACSCS PVHPQQAFCN
 41 ADVVIRAKAV SEKEVDSGND IYGNPIKRIQ YEIKQIKMFK
 81 GPEKDIEFIY TAPSSAVCGV SLDVGGKKEY LIAGKAEGDG
121 KMHITLCDFI VPWDTLSTTQ KKSLNHRYQM GCECKITRCP
```

-continued
```
161 MIPCYISSPD ECLWMDWVTE KNINGHQAKF FACIKRSDGS
201 CAWYRGAAPP KQEFLDIEDP
```

See Stetler-Stevenson et al., Tissue inhibitor of metalloproteinase (TIMP-2). A new member of the metalloproteinase inhibitor family, Biol. Chem. 264 (29), 17374–17378 (1989).

A human TIMP-3 can have the following amino acid sequence (SEQ ID NO:3).

```
  1 MTPWLGLIVL LGSWSLGDWG AEACTCSPSH PQDAFCNSDI
 41 VIRAKVVGKK LVKEGPFGTL VYTIKQMKMY RGFTKMPHVQ
 81 YIHTEASESL CGLKLEVNKY QYLLTGRVYD GKMYTGLCNF
121 VERWDQLTLS QRKGLNYRYH LGCNCKIKSC YYLPCFVTSK
161 NECLWTDMLS NFGYPGYQSK HYACIRQKGG YCSWYRGWAP
201 PDKSIINATD P
```

See Wick et al., A novel member of human tissue inhibitor of metalloproteinases (TIMP) gene family is regulated during G1 progression, mitogenic stimulation, differentiation, and senescence, J. Biol. Chem. 269 (29), 18953–18960 (1994).

A human TIMP-4 can have the following amino acid sequence (SEQ ID NO:4).

```
  1 MPGSPRPAPS WVLLLRLLAL LRPPGLGEAC SCAPAHPQQH
 41 ICHSALVIRA KISSEKVVPA SADPADTEKM LRYEIKQIKM
 81 FKGFEKVKDV QYIYTPFDSS LCGVKLEANS QKQYLLTGQV
121 LSDGKVFIHL CNYIEPWEDL SLVQRESLNH HYHLNCGCQI
161 TTCYTVPCTI SAPNECLWTD WLLERKLYGY QAQHYVCMKH
201 VDGTCSWYRG HLPLRKEFVD IVQP
```

See Greene et al., Molecular cloning and characterization of human tissue inhibitor of metalloproteinase 4, J. Biol. Chem. 271 (48), 30375–30380 (1996).

Polypeptide inhibitors of the invention have sequences related to such TIMPs. However, the present polypeptides are shorter and more stable than these TIMPs. In particular, the present polypeptide inhibitors have about 100 fewer amino acids then the naturally available TIMPs. Hence, they are simpler, cheaper and easier to make. More significantly, the present inhibitors have a highly stabilized beta barrel topology that has been enhanced by incorporation of additional cysteine residues. This topology provides an inhibitor that is resistant to denaturation and to protease action.

The present polypeptide inhibitors can inhibit the activity of many types of matrix metalloproteinases. The present polypeptides can also prevent the activation of proenzyme matrix metalloproteinases, as well as inhibit the enzymatic activity of mature matrix metalloproteinases. For example, polypeptides containing sequences that are more conserved in a variety of TIMPs can be used to provide inhibitors that are generally effective against a variety of matrix metalloproteinases. However, polypeptides containing sequences are less conserved amongst the various TIMPs, for example, sequences unique to a specific TIMP, can be used to provide inhibitors that are specific for individual matrix metalloproteinases.

Hence, polypeptides with sequences related to any TIMP are contemplated by the invention as inhibitors of matrix metalloproteinases, as well as variant polypeptides that have one or more amino acids substituted for the amino acids that are naturally present in the TIMP. Mixtures of polypeptides with different sequences are also contemplated. In general, the polypeptide sequences, polypeptide variants and mixtures of polypeptides are formulated and used in a manner that optimizes wound healing, the regeneration of skin, and the prevention of scarring or generation of healthy skin. Hence, the composition and formulations of the present polypeptides can be varied so that lesser or greater levels of inhibition are achieved so long as healing is promoted.

The size of a polypeptide inhibitor can vary. In general, a polypeptide of only about five amino acids can be too small to provide optimal inhibition. However, polypeptides of more than about eight to nine amino acids are sufficiently long to provide inhibition. Therefore, while the overall length is not critical, polypeptides longer than eight amino acids are often employed in the invention. Other polypeptides employed in the invention are longer than nine amino acids. Still other polypeptides employed in the invention are longer than ten amino acids. Moreover, polypeptides that are longer than about fifteen amino acids are also used in the invention.

There is no particular upper limit on polypeptide size. However, longer polypeptides can be more stable than shorter peptides. The polypeptide inhibitors of the invention are generally shorter than about four hundred amino acids. Many polypeptide inhibitors used in the invention are shorter than about three hundred amino acids. Other polypeptide inhibitors used in the invention are shorter than about two hundred amino acids. Polypeptides shorter than about one hundred fifty amino acids can also be used. Similarly, polypeptides shorter than about one hundred twenty five amino acids are also used in the invention.

One polypeptide provided by the invention has SEQ ID NO:5, as follows.

```
 1  MCSCSPVHPQ QAFSNADVVI RAKAVSEKEV DSGNDIYGNP

41  IKRIQYEIKQ IKMFKGPEKD IEFIYTAPSS AVCGVSLDVG

81  GKKEYCIAGK AEGDGKMHIT LCDFICPW
```

Upon expression in *E. coli*, the SEQ ID NO:5 polypeptide can be cleaved at its N-terminus so the N-terminal methionine is missing. Such a polypeptide can have SEQ ID NO:20, as follows.

```
 1   CSCSPVHPQ QAFSNADVVI RAKAVSEKEV DSGNDIYGNP

41  IKRIQYEIKQ IKMFKGPEKD IEFIYTAPSS AVCGVSLDVG

81  GKKEYCIAGK AEGDGKMHIT LCDFICPW
```

The SEQ ID NO:5 and SEQ ID NO:20 polypeptide inhibitors show excellent inhibitory properties towards matrix metalloproteinase-9, as well as with other matrix metalloproteinases. The SEQ ID NO:5 and SEQ ID NO:20 polypeptide inhibitors embody several fundamental and desirable properties. First, these proteins are easily purified in a form that is fully folded and soluble. By changing the expression vector, it is possible to produce these proteins in nonbacterial systems, such a bacculovirus, or mammalian cell lines. Second, these proteins are extremely stable and long-lived. This property is related to the beta barrel topology that is maintained and enhanced by addition of cysteine residues that can form stabilizing disulfide bonds. Such stability is an important consideration for a molecule that is to be introduced into a wound environment. Third, the SEQ ID NO:5 and SEQ ID NO:20 polypeptide inhibitors are good, broad range matrix metalloproteinase inhibitors. They form long-lived and stoichiometric complexes with matrix metalloproteinases. Fourth, these SEQ ID NO:5 and SEQ ID NO:20 polypeptide inhibitors are immunogenic so that antibodies can readily be raised against them. These antibodies are useful for tracking the protein(s) during in situ experiments. Fifth, the SEQ ID NO:5 and SEQ ID NO:20 polypeptide inhibitors contain a number of aromatic amino acids (one tryptophan and four tyrosines). Such aromatic amino acids make the SEQ ID NO:5/SEQ ID NO:20 polypeptide amenable to a host of intrinsic fluorescence experiments, alleviating the need to modify the protein with extrinsic fluorophores.

Molecular modeling methods were employed in order to design the SEQ ID NO:5 polypeptide inhibitor. The protein was constructed by aligning the amino acid sequences of the four TIMP molecules in order to define regions of high amino acid identity. The SEQ ID NO:5 sequence therefore constitutes a consensus amino acid sequence derived from sequence alignment studies. An analysis of the contact region in the published three-dimensional model of a TIMP-matrix metalloproteinase structure allowed for the removal of a protein domain of approximately 100 amino acids that was not involved in the binding interaction. A disulfide bond was introduced into the synthetic protein inhibitor in order to stabilize the new carboxy terminus.

The SEQ ID NO:5 and SEQ ID NO:20 polypeptides were produced in good yield in *E. coli* and were purified to homogeneity (Hodges et al., 1998; Liu et al., 1997). A maltose binding protein fusion purification scheme was employed so that homogeneous SEQ ID NO:5 and SEQ ID NO:20 polypeptides could be prepared from crude extract in a matter of days. However, isolation of the SEQ ID NO:5 and SEQ ID NO:20 polypeptides is not dependent on use of the maltose binding protein fusion scheme. Should it be desired, nucleic acids encoding the SEQ ID NO:5 or SEQ ID NO:20 polypeptide or any other polypeptide of the invention can be cloned into any expression vector that is available.

A nucleic acid encoding the SEQ ID NO:5 and SEQ ID NO:20 polypeptides was built in approximately three weeks from a series of short oligonucleotides using a combination of hybridization and enzymatic synthesis. The full-length gene sequence was directionally cloned into a protein expression vector and the sequence was verified by DNA sequencing. Design at the nucleotide level aided in cloning experiments by incorporating restriction endonuclease sites into the sequence, and it also helped to maximize protein expression by employing an *E. coli* codon bias.

A nucleic acid that encodes the SEQ ID NO:5 and SEQ ID NO:20 polypeptides is, for example, SEQ ID NO:6, provided below.

```
 1  ATGTGCAGCT GCAGCCCGGT GCATCCGCAG CAGGCGTTTA

41  GCAACGCGGA TGTGGTGATT CGCGCGAAAG CGGTGAGCGA

81  AAAAGAAGTC GATAGCGGCA ACGATATTTA TGGCAACCCG
```

```
-continued
121 ATTAAACGCA TTCAGTATGA AATTAAACAG ATTAAAATGT

161 TTAAAGGCCC GGAAAAAGAT ATTGAATTTA TTTATACCGC

201 GCCGAGCAGC GCGGTGTGCG GCGTGAGCCT GGATGTGGGC

241 GGCAAAAAAG AATATTGCAT TGCGGGCAAA GCGGAAGGCG

281 ATGGCAAAAT GCATATTACC CTGTGCGATT TTATTTGCCC

321 GTGGTAGAAG CTTATAGAC
```

The invention also provides nucleic acids that are similar to SEQ ID NO:6. In particular, the invention provides nucleic acids that can hybridize under stringent conditions to a nucleic acid comprising SEQ ID NO:6. "Stringent hybridization conditions" and "stringent hybridization wash conditions" in the context of nucleic acid hybridization are somewhat sequence dependent, and may differ depending upon the environmental conditions of the nucleic acid. For example, longer sequences tend to hybridize specifically at higher temperatures. An extensive guide to the hybridization of nucleic acids is found in Tijssen, Laboratory Techniques in Biochemistry and Molecular biology-Hybridization with Nucleic Acid Probes, page 1, chapter 2 "Overview of principles of hybridization and the strategy of nucleic acid probe assays" Elsevier, New York (1993). See also, J. Sambrook et al., Molecular Cloning: A Laboratory Manual, Cold Spring Harbor Press, N.Y., pp 9.31–9.58 (1989); J. Sambrook et al., Molecular Cloning: A Laboratory Manual, Cold Spring Harbor Press, N.Y. (3rd ed. 2001).

Generally, highly stringent hybridization and wash conditions are selected to be about 5° C. lower than the thermal melting point ($T_m$) for the specific double-stranded sequence at a defined ionic strength and pH. For example, under "highly stringent conditions" or "highly stringent hybridization conditions" a nucleic acid will hybridize to its complement to a detectably greater degree than to other sequences (e.g., at least 2-fold over background). By controlling the stringency of the hybridization and/or washing conditions nucleic acids that are 100% complementary can be identified.

Alternatively, stringency conditions can be adjusted to allow some mismatching in sequences so that lower degrees of similarity are detected (heterologous probing). Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short nucleic acids (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl and 0.3 M trisodium citrate) at 50 to 55° C. Exemplary moderate stringency conditions include hybridization in 40 to 45% formamide, 1.0 M NaCl, 1% SDS at 37° C., and a wash in 0.5×to 1×SSC at 55 to 60° C. Exemplary high stringency conditions include hybridization in 50% formamide, 1 M NaCl, 1% SDS at 37° C., and a wash in 0.1×SSC at 60° C. to 65° C.

The degree of complementarity or sequence identity of hybrids obtained during hybridization is typically a function of post hybridization washes, the critical factors being the ionic strength and temperature of the final wash solution. The type and length of hybridizing nucleic acids also affects whether hybridization will occur and whether any hybrids formed will be stable under a given set of hybridization and wash conditions. For DNA-DNA hybrids, the $T_m$ can be approximated from the equation of Meinkoth and Wahl Anal. Biochem. 138:267–284 (1984):

$$T_m 81.5° C.+16.6(\log M)+0.41(\% GC)-0.61(\% \text{form})-500/L$$

where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe.

Very stringent conditions are selected to be equal to the $T_m$.

An example of stringent hybridization conditions for hybridization of complementary nucleic acids that have more than 100 complementary residues on a filter in a Southern or Northern blot is 50% formamide with 1 mg of heparin at 42° C., with the hybridization being carried out overnight. An example of highly stringent conditions is 0.1 5 M NaCl at 72° C. for about 15 minutes. An example of stringent wash conditions is a 0.2×SSC wash at 65° C. for 15 minutes (see also, Sambrook, infra). Often, a high stringency wash is preceded by a low stringency wash to remove background probe signal. An example of medium stringency for a duplex of, e.g., more than 100 nucleotides, is 1×SSC at 45° C. for 15 minutes. An example of low stringency wash conditions for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C.

Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Variant and Derivative Polypeptide Inhibitors

Polypeptides having any of SEQ ID NO:1–5 or 20 are contemplated as polypeptide inhibitors of the invention. However, polypeptide variants and derivatives of the polypeptides having any of SEQ ID NO:1–5 or 20 are also useful as polypeptide inhibitors. Such polypeptide variants and derivatives can have one or more amino acid substitutions, deletions, insertions or other modifications so long as the polypeptide variant or derivative can inhibit a matrix metalloproteinase.

Amino acid residues of the isolated polypeptides can be genetically encoded L-amino acids, naturally occurring non-genetically encoded L-amino acids, synthetic L-amino acids or D-enantiomers of any of the above. The amino acid notations used herein for the twenty genetically encoded L-amino acids and common non-encoded amino acids are conventional and are as shown in Table 1.

TABLE 1

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | Bala |
| 2,3-Diaminopropionic acid | | Dpr |
| α-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| β-2-thienylalanine | | Thi |
| Methionine sulfoxide | | MSO |
| Homoarginine | | Harg |
| N-acetyl lysine | | AcLys |
| 2,4-Diamino butyric acid | | Dbu |
| ρ-Aminophenylalanine | | Phe(pNH$_2$) |
| N-methylvaline | | MeVal |
| Homocysteine | | Hcys |
| Homoserine | | Hser |
| ε-Amino hexanoic acid | | Aha |
| δ-Amino valeric acid | | Ava |
| 2,3-Diaminobutyric acid | | Dab |

Polypeptides that are encompassed within the scope of the invention can have one or more amino acids substituted with an amino acid of similar chemical and/or physical properties, so long as these variant or derivative polypeptides retain the ability to inhibit the activity of a matrix metalloproteinase, stimulate cellular growth of fibroblasts or keratinocytes, or stimulate the cellular migration of fibroblasts.

Amino acids that are substitutable for each other generally reside within similar classes or subclasses. As known to one of skill in the art, amino acids can be placed into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include glycine, proline and methionine. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include cysteine. Examples of non-genetically encoded cysteine-like amino acids include homocysteine and penicillamine.

As will be appreciated by those having skill in the art, the above classifications are not absolute. Several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a polypeptide.

Certain commonly encountered amino acids that are not genetically encoded and that can be present, or substituted for an amino acid, in the polypeptides and polypeptide analogues of the invention include, but are not limited to, β-alanine (b-Ala) and other omega-amino acids such as 3-aminopropionic acid (Dap), 2,3-diaminopropionic acid (Dpr), 4-aminobutyric acid and so forth; ε-aminoisobutyric acid (Aib); α-aminohexanoic acid (Aha); 67-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). These amino acids also fall into the categories defined above.

The classifications of the above-described genetically encoded and non-encoded amino acids are summarized in Table 2, below. It is to be understood that Table 2 is for illustrative purposes only and does not purport to be an exhaustive list of amino acid residues that may comprise the polypeptides and polypeptide analogues described herein. Other amino acid residues that are useful for making the polypeptides and polypeptide analogues described herein can be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 2

| Classification | Genetically Encoded | Genetically Non-Encoded |
|---|---|---|
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-NH$_2$), DBU, A$_2$ BU |
| Polar | Q, N, S, T, Y | Cit, AcLys, MSO, hSer |
| Cysteine-Like | C | Pen, hCys, β-methyl Cys |

Polypeptides of the invention can have any amino acid substituted by any similarly classified amino acid to create a variant or derivative polypeptide, so long as the polypeptide variant or derivative retains an ability to inhibit the activity of a matrix metalloproteinase.

Hence, to optimize the structural and binding properties of the present polypeptide inhibitors, a full-length amino acid sequence that is an approximate average of the four known TIMP sequences can be generated. This can be done, for example, by performing a robust pair-wise alignment of TIMP amino acid sequences using the program CLUSTAL (Higgins et al., 1992). A consensus sequence was constructed using this type of alignment. For non-conserved amino acids in the contact region, substitutions can be made that preserve the hydrophobic character of the vicinity, but that negate specific side chain-side chain interactions.

The amino acids involved in binding can be identified and distinguished from those involved in maintaining the stable beta barrel topology. Conservative amino acid substitutions can be made amongst the amino acids that are involved in maintaining the stable beta barrel topology. Less conservative, or even non-conservative, amino acid changes can be made amongst the amino acids involved in binding to metalloproteinases.

Additional amino acids can be removed or added to the C-terminal domain of the polypeptide inhibitor. Through the analysis of the two TIMP/MMP complex structures, it was apparent that only the N-terminal TIMP region made significant contact with the catalytic domain of the MMP. This was confirmed later by docking the final protein model with MMP-9.

Such manipulations reduced the overall length of the SEQ ID NO:5 protein from the usual TIMP size of about 225 amino acids to about 108 amino acids. In order to stabilize the new C-terminus of the protein, two additional amino acid replacements were made in the SEQ ID NO:5 and 20 polypeptides: Leu85 and Val101 were changed to cysteine. Structural studies show that these two residues normally were within 3 Å of each other, and could form a disulfide bond if altered to cysteine. In this way the last loop region of the inhibitor polypeptide is locked in place. In addition a cysteine residue in position 13 was changed to serine. Thus all cysteine residues (6) in the SEQ ID NO:5 and 20 polypeptides participate in disulfide bond formation.

Similar manipulations can be performed to modulate the stability or binding properties the SEQ ID NO:5 and 20 polypeptides. For example, to further enhance the stability of the present polypeptide inhibitors, a homology model of an optimized polypeptide inhibitor can be built. The amino acid sequence of the SEQ ID NO:5 or 20 inhibitor can be threaded onto the alpha carbon trace of any one of the available TIMPs using the programs ProMod and Swiss-Model (Peitsch, 1996; Peitsch et al., 1996). This model can then be subjected to energy minimization using a GROMOS 96 forcefield, with several rounds of molecular mechanics geometry optimization using the SYBYL forcefield (Clark et al., 1989). The final minimized/optimized model can then analyzed for bad side chain interactions and torsional geometry. While such studies have been performed to generate an optimized three-dimensional model comprising the SEQ ID NO:5 sequence, these studies were performed by comparison to TIMP-2 (see Examples). Further analyses by comparison to other TIMPs can yield polypeptide inhibitors with variant and derivative sequences that have altered stability and binding properties.

The final amino acid sequence can then be back translated and nucleotide codons can be specifically selected to reflect the optimum codon usage of the organism in which the polypeptide inhibitor is to be expressed, for example, in *E. coli*, human, or insect cell expression systems. These manipulations will maximize protein expression.

The SEQ ID NO:5 polypeptide is 108 amino acids in length and the SEQ ID NO:20 polypeptide is 107 amino acids in length. One of skill in the art may choose to make a series of carboxy terminal deletions can be made to make a shorter polypeptide. While employing this approach, one of skill in the art may choose to retain a cysteine residue near the C-terminus. For example, Cys101 within the SEQ ID NO:5 polypeptide is participating in an important disulfide bond interaction. Hence, C-terminal deletions of only seven amino acids may be performed on the SEQ ID NO:5 or 20 polypeptide to generate a somewhat smaller but functional inhibitor polypeptide. Alternatively, a cysteine can be added near the C-terminus of a truncated polypeptide inhibitor if more than seven amino acids are deleted.

The flexible loop region of the SEQ ID NO:5 or SEQ ID NO:20 polypeptide may also be modified in certain embodiments, for example, by deleting portions of the region between Val25 and Glu47. Such deletion mutations would preserve the main binding interface, but may remove some of the binding specificity toward TIMP-2 like molecules.

In one embodiment, the polypeptide inhibitors of the invention include any one of the polypeptides that have SEQ ID NO:7.

wherein:

$Xaa_1$, $Xaa_6$, $Xaa_9$, $Xaa_{33}$, $Xaa_{38}$, $Xaa_{40}$, $Xaa_{53}$, $Xaa_{56}$, $Xaa_{57}$, $Xaa_{68}$, $Xaa_{74}$, $Xaa_{80}$, $Xaa_{81}$, $Xaa_{89}$, $Xaa_{93}$, $Xaa_{95}$, $Xaa_{97}$, and $Xaa_{107}$ are separately each apolar amino acids;

$Xaa_2$, $Xaa_4$, $Xaa_{73}$, $Xaa_{86}$, $Xaa_{102}$, and $Xaa_{106}$ are separately each a cysteine-like amino acid;

$Xaa_3$, $Xaa_5$, $Xaa_{10}$, $Xaa_{11}$, $Xaa_{14}$, $Xaa_{15}$, $Xaa_{26}$, $Xaa_{32}$, $Xaa_{34}$, $Xaa_{37}$, $Xaa_{39}$, $Xaa_{45}$, $Xaa_{46}$, $Xaa_{50}$, $Xaa_{65}$, $Xaa_{66}$, $Xaa_{69}$, $Xaa_{70}$, $Xaa_{76}$, $Xaa_{85}$, and $Xaa_{100}$ are separately each a polar amino acid;

$Xaa_7$, $Xaa_{12}$, $Xaa_{16}$, $Xaa_{18}$, $Xaa_{19}$, $Xaa_{20}$, $Xaa_{22}$, $Xaa_{24}$, $Xaa_{25}$, $Xaa_{30}$, $Xaa_{36}$, $Xaa_{41}$, $Xaa_{44}$, $Xaa_{48}$, $Xaa_{51}$, $Xaa_{61}$, $Xaa_{64}$, $Xaa_{67}$, $Xaa_{71}$, $Xaa_{72}$, $Xaa_{75}$, $Xaa_{77}$, $Xaa_{79}$, $Xaa_{87}$, $Xaa_{88}$, $Xaa_{91}$, $Xaa_{99}$, $Xaa_{101}$, and $Xaa_{105}$ are separately each an aliphatic amino acid;

$Xaa_8$, $Xaa_{21}$, $Xaa_{23}$, $Xaa_{28}$, $Xaa_{42}$, $Xaa_{43}$, $Xaa_{49}$, $Xaa_{52}$, $Xaa_{55}$, $Xaa_{59}$, $Xaa_{82}$, $Xaa_{83}$, $Xaa_{90}$, $Xaa_{96}$, and $Xaa_{98}$ are separately each a basic amino acid;

$Xaa_{13}$, $Xaa_{54}$, $Xaa_{63}$, and $Xaa_{104}$ are separately each an aromatic amino acid;

$Xaa_{17}$, $Xaa_{27}$, $Xaa_{29}$, $Xaa_{31}$, $Xaa_{35}$, $Xaa_{47}$, $Xaa_{58}$, $Xaa_{60}$, $Xaa_{62}$, $Xaa_{78}$, $Xaa_{84}$, $Xaa_{92}$, $Xaa_{94}$, and $Xaa_{103}$ are separately each an acidic amino acid; and $Xaa_{108}$ is tryptophan; and wherein the polypeptide has a beta barrel conformation and is capable of inhibiting the activity of a matrix metalloproteinase.

In some embodiments, desirable polypeptides that fall within SEQ ID NO:7 have cysteine instead of cysteine-like amino acids at positions $Xaa_2$, $Xaa_4$, $Xaa_{73}$, $Xaa_{86}$, $Xaa_{102}$, and $Xaa_{106}$.

In other embodiments, desirable polypeptides that fall within SEQ ID NO:7 have methionine at position $Xaa_1$. Alternatively, the $Xaa_1$ amino acid is missing due to processing that occurs naturally within the cell that is used to express the polypeptide inhibitor. Desirable polypeptides that fall within SEQ ID NO:7 can also have methionine at any one of positions $Xaa_{53}$ or $Xaa_{97}$.

In other embodiments, desirable polypeptides that fall within SEQ ID NO:7 have serine or threonine at any of positions $Xaa_3$, $Xaa_5$, $Xaa_{14}$, $Xaa_{26}$, $Xaa_{32}$, $Xaa_{66}$, $Xaa_{69}$, $Xaa_{70}$, $Xaa_{76}$ or $Xaa_{100}$.

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-

$Xaa_{13}$-$Xaa_{14}$-$Xaa_{15}$-$Xaa_{16}$-$Xaa_{17}$-$Xaa_{18}$-$Xaa_{19}$-$Xaa_{20}$-$Xaa_{21}$-$Xaa_{22}$-$Xaa_{23}$-

$Xaa_{24}$-$Xaa_{25}$-$Xaa_{26}$-$Xaa_{27}$-$Xaa_{28}$-$Xaa_{29}$-$Xaa_{30}$-$Xaa_{31}$-$Xaa_{32}$-$Xaa_{33}$-$Xaa_{34}$-

$Xaa_{35}$-$Xaa_{36}$-$Xaa_{37}$-$Xaa_{38}$-$Xaa_{39}$-$Xaa_{40}$-$Xaa_{41}$-$Xaa_{42}$-$Xaa_{43}$-$Xaa_{44}$-$Xaa_{45}$-

$Xaa_{46}$-$Xaa_{47}$-$Xaa_{48}$-$Xaa_{49}$-$Xaa_{50}$-$Xaa_{51}$-$Xaa_{52}$-$Xaa_{53}$-$Xaa_{54}$-$Xaa_{55}$-$Xaa_{56}$-

$Xaa_{57}$-$Xaa_{58}$-$Xaa_{59}$-$Xaa_{60}$-$Xaa_{61}$-$Xaa_{62}$-$Xaa_{63}$-$Xaa_{64}$-$Xaa_{65}$-$Xaa_{66}$-$Xaa_{67}$-

$Xaa_{68}$-$Xaa_{69}$-$Xaa_{70}$-$Xaa_{71}$-$Xaa_{72}$-$Xaa_{73}$-$Xaa_{74}$-$Xaa_{75}$-$Xaa_{76}$-$Xaa_{77}$-$Xaa_{78}$-

$Xaa_{79}$-$Xaa_{80}$-$Xaa_{81}$-$Xaa_{82}$-$Xaa_{83}$-$Xaa_{84}$-$Xaa_{85}$-$Xaa_{86}$-$Xaa_{87}$-$Xaa_{88}$-$Xaa_{89}$-

$Xaa_{90}$-$Xaa_{91}$-$Xaa_{92}$-$Xaa_{93}$-$Xaa_{94}$-$Xaa_{95}$-$Xaa_{96}$-$Xaa_{97}$-$Xaa_{98}$-$Xaa_{99}$-$Xaa_{100}$-

$Xaa_{101}$-$Xaa_{102}$-$Xaa_{103}$-$Xaa_{104}$-$Xaa_{105}$-$Xaa_{106}$-$Xaa_{107}$-$Xaa_{108}$

In other embodiments, desirable polypeptides that fall within SEQ ID NO:7 have alanine, valine, isoleucine or leucine at any of positions $Xaa_7$, $Xaa_{12}$, $Xaa_{16}$, $Xaa_{18}$, $Xaa_{19}$, $Xaa_{20}$, $Xaa_{22}$, $Xaa_{24}$, $Xaa_{25}$, $Xaa_{30}$, $Xaa_{36}$, $Xaa_{41}$, $Xaa_{44}$, $Xaa_{48}$, $Xaa_{51}$, $Xaa_{61}$, $Xaa_{64}$, $Xaa_{67}$, $Xaa_{71}$, $Xaa_{72}$, $Xaa_{75}$, $Xaa_{77}$, $Xaa_{79}$, $Xaa_{87}$, $Xaa_{88}$, $Xaa_{91}$, $Xaa_{99}$, $Xaa_{101}$, or $Xaa_{105}$.

In other embodiments, desirable polypeptides that fall within SEQ ID NO:7 have histidine at any of positions $Xaa_8$ or $Xaa_{98}$.

In other embodiments, desirable polypeptides that fall within SEQ ID NO:7 have proline at any of positions $Xaa_6$, $Xaa_9$, $Xaa_{40}$, $Xaa_{57}$, $Xaa_{68}$, or $Xaa_{107}$.

In other embodiments, desirable polypeptides that fall within SEQ ID NO:7 have asparagine or glutamine at any of positions $Xaa_{10}$, $Xaa_{11}$, $Xaa_{15}$, $Xaa_{34}$, $Xaa_{39}$, $Xaa_{45}$, or $Xaa_{50}$.

In other embodiments, desirable polypeptides that fall within SEQ ID NO:7 have phenylalanine at any of positions $Xaa_{13}$, $Xaa_{54}$, $Xaa_{63}$, or $Xaa_{104}$.

In other embodiments, desirable polypeptides that fall within SEQ ID NO:7 have aspartic acid or glutamic acid at any of positions $Xaa_{17}$, $Xaa_{27}$, $Xaa_{29}$, $Xaa_{31}$, $Xaa_{35}$, $Xaa_{47}$, $Xaa_{58}$, $Xaa_{60}$, $Xaa_{62}$, $Xaa_{78}$, $Xaa_{84}$, $Xaa_{92}$, $Xaa_{94}$ or $Xaa_{103}$.

In other embodiments, desirable polypeptides that fall within SEQ ID NO:7 have lysine or arginine at any of positions $Xaa_{21}$, $Xaa_{23}$, $Xaa_{28}$, $Xaa_{42}$, $Xaa_{43}$, $Xaa_{49}$, $Xaa_{52}$, $Xaa_{55}$, $Xaa_{59}$, $Xaa_{82}$, $Xaa_{83}$, $Xaa_{90}$, or $Xaa_{96}$ In other embodiments, desirable polypeptides that fall within SEQ ID NO:7 have tyrosine at any of positions $Xaa_{37}$, $Xaa_{46}$, $Xaa_{65}$, or $Xaa_{85}$.

In other embodiments, desirable polypeptides that fall within SEQ ID NO:7 have glycine at any of positions $Xaa_{33}$, $Xaa_{38}$, $Xaa_{56}$, $Xaa_{74}$, $Xaa_{80}$, $Xaa_{81}$, $Xaa_{89}$, $Xaa_{93}$, or $Xaa_{95}$.

Therefore, in one embodiment, the polypeptides of the invention can have SEQ ID NO:21

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-

$Xaa_{13}$-$Xaa_{14}$-$Xaa_{15}$-$Xaa_{16}$-$Xaa_{17}$-$Xaa_{18}$-$Xaa_{19}$-$Xaa_{20}$-$Xaa_{21}$-$Xaa_{22}$-$Xaa_{23}$-

$Xaa_{24}$-$Xaa_{25}$-$Xaa_{26}$-$Xaa_{27}$-$Xaa_{28}$-$Xaa_{29}$-$Xaa_{30}$-$Xaa_{31}$-$Xaa_{32}$-$Xaa_{33}$-$Xaa_{34}$-

$Xaa_{35}$-$Xaa_{36}$-$Xaa_{37}$-$Xaa_{38}$-$Xaa_{39}$-$Xaa_{40}$-$Xaa_{41}$-$Xaa_{42}$-$Xaa_{43}$-$Xaa_{44}$-$Xaa_{45}$-

$Xaa_{46}$-$Xaa_{47}$-$Xaa_{48}$-$Xaa_{49}$-$Xaa_{50}$-$Xaa_{51}$-$Xaa_{52}$-$Xaa_{53}$-$Xaa_{54}$-$Xaa_{55}$-$Xaa_{56}$-

$Xaa_{57}$-$Xaa_{58}$-$Xaa_{59}$-$Xaa_{60}$-$Xaa_{61}$-$Xaa_{62}$-$Xaa_{63}$-$Xaa_{64}$-$Xaa_{65}$-$Xaa_{66}$-$Xaa_{67}$-

$Xaa_{68}$-$Xaa_{69}$-$Xaa_{70}$-$Xaa_{71}$-$Xaa_{72}$-$Xaa_{73}$-$Xaa_{74}$-$Xaa_{75}$-$Xaa_{76}$-$Xaa_{77}$-$Xaa_{78}$-

$Xaa_{79}$-$Xaa_{80}$-$Xaa_{81}$-$Xaa_{82}$-$Xaa_{83}$-$Xaa_{84}$-$Xaa_{85}$-$Xaa_{86}$-$Xaa_{87}$-$Xaa_{88}$-$Xaa_{89}$-

$Xaa_{90}$-$Xaa_{91}$-$Xaa_{92}$-$Xaa_{93}$-$Xaa_{94}$-$Xaa_{95}$-$Xaa_{96}$-$Xaa_{97}$-$Xaa_{98}$-$Xaa_{99}$-$Xaa_{100}$-

$Xaa_{101}$-$Xaa_{102}$-$Xaa_{103}$-$Xaa_{104}$-$Xaa_{105}$-$Xaa_{106}$-$Xaa_{107}$-$Xaa_{108}$ wherein:

$Xaa_1$, $Xaa_{53}$ and $Xaa_{97}$ are separately each methionine;

$Xaa_2$, $Xaa_4$, $Xaa_{73}$, $Xaa_{86}$, $Xaa_{102}$, and $Xaa_{106}$ are separately each cysteine;

$Xaa_3$, $Xaa_5$, $Xaa_{14}$, $Xaa_{26}$, $Xaa_{32}$, $Xaa_{66}$, $Xaa_{69}$, $Xaa_{70}$, $Xaa_{76}$ and $Xaa_{100}$ are separately each serine or threonine;

$Xaa_7$, $Xaa_{12}$, $Xaa_{16}$, $Xaa_{18}$, $Xaa_{19}$, $Xaa_{20}$, $Xaa_{22}$, $Xaa_{24}$, $Xaa_{25}$, $Xaa_{30}$, $Xaa_{36}$, $Xaa_{41}$, $Xaa_{44}$, $Xaa_{48}$, $Xaa_{51}$, $Xaa_{61}$, $Xaa_{64}$, $Xaa_{67}$, $Xaa_{71}$, $Xaa_{72}$, $Xaa_{75}$, $Xaa_{77}$, $Xaa_{79}$, $Xaa_{87}$, $Xaa_{88}$, $Xaa_{91}$, $Xaa_{99}$, $Xaa_{101}$, and $Xaa_{105}$ are separately each alanine, valine, isoleucine or leucine;

$Xaa_8$ and $Xaa_{98}$ and are separately each histidine;

$Xaa_6$, $Xaa_9$, $Xaa_{40}$, $Xaa_{57}$, $Xaa_{68}$, and $Xaa_{107}$ and are separately each proline;

$Xaa_{10}$, $Xaa_{11}$, $Xaa_{15}$, $Xaa_{34}$, $Xaa_{39}$, $Xaa_{45}$, and $Xaa_{50}$ are separately each asparagine or glutamine;

$Xaa_{13}$, $Xaa_{54}$, $Xaa_{63}$, and $Xaa_{104}$ are separately each phenylalanine;

$Xaa_{17}$, $Xaa_{27}$, $Xaa_{29}$, $Xaa_{31}$, $Xaa_{35}$, $Xaa_{47}$, $Xaa_{58}$, $Xaa_{60}$, $Xaa_{62}$, $Xaa_{78}$, $Xaa_{84}$, $Xaa_{92}$, $Xaa_{94}$ and $Xaa_{103}$ are separately each aspartic acid or glutamic acid;

$Xaa_{21}$, $Xaa_{23}$, $Xaa_{28}$, $Xaa_{42}$, $Xaa_{43}$, $Xaa_{49}$, $Xaa_{52}$, $Xaa_{55}$, $Xaa_{59}$, $Xaa_{82}$, $Xaa_{83}$, $Xaa_{90}$, and $Xaa_{96}$ are separately each lysine or arginine;

$Xaa_{37}$, $Xaa_{46}$, $Xaa_{65}$, and $Xaa_{85}$ are separately each tyrosine;

$Xaa_{33}$, $Xaa_{38}$, $Xaa_{56}$, $Xaa_{74}$, $Xaa_{80}$, $Xaa_{81}$, $Xaa_{89}$, $Xaa_{93}$, and $Xaa_{95}$ are separately each glycine;

$Xaa_{108}$ is tryptophan; and wherein the polypeptide has a beta barrel conformation and is capable of inhibiting the activity of a matrix metalloproteinase.

Desirable polypeptide inhibitors of the invention have a beta barrel conformation. As used herein a beta barrel conformation means that the core of the polypeptide comprises beta strand secondary structures that fold into a barrel-like tertiary structure. The beta barrel is stabilized by intra-strand hydrogen bonding and internal hydrophobic packing interactions. A beta barrel is a recognized tertiary structure known to those skilled in the art of protein structure and function.

In the present invention, the fundamental beta barrel conformation is further stabilized by engineered disulfide bonds that help maintain the overall topology of the folded polypeptide. For example, a polypeptide having SEQ ID NO:5 or SEQ ID NO:20 can fold into a six stranded beta barrel conformation with three disulfide bonds crosslinking the separate beta peptide strands. Amino acids involved in binding matrix metalloproteinases are displayed on the surface of the barrel-like structure.

The conformation of polypeptides can be determined by any procedure available to one of skill in the art. For example, the conformation can be determined by x-ray crystallography or by computer modeling. For example, computer modeling can be performed using programs such as the Swiss PDB Viewer (Guex and Peitsch, 1997) and Rasmol (Sayle and Milner-White, 1995) programs. Modeling work can be performed on any available computer with sufficient speed and RAM. For example, much of the computer modeling work provided herein was performed on a Compaq PC running Windows 95, as well as a Silicon Graphics, Inc. Octane UNIX workstation. Additionally, the Cerius2 molecular package from Molecular Simulations, Inc. was utilized on the Octane UNIX workstation.

For comparison, three dimensional structure files of selected matrix metalloproteinases (MMPs) can be downloaded from the Protein Databank as follows (filename, reference): MMP-1 (1FBL, Li et al., 1995), MMP-2 (1GEN, Libson et al., 1995), MMP-8 (1JAO, 1JAN, Grams, et al., 1995; Reinemer et al., 1994), MMP-9 (1MMQ, Browner et al., 1995), TIMP-2/MT-1 MMP complex (1BUV, Fernandez-Catalan et al., 1998), TIMP-2 (1BR9, Tuuttila et al., 1998), and TIMP-1/MMP complex (1UEA, Gomis-Ruth et al., 1997; Huang et al., 1996; Becker et al., 1995). These files can be used to analyze and compare three-dimensional structure of the polypeptide inhibitors with naturally occurring TIMP proteins, and can facilitate identification of the amino acids responsible for specific binding interactions with different matrix metalloproteinases.

The ability of a polypeptide to inhibit matrix metalloproteinase activity can be assessed by any procedure available to one of skill in the art. Many different assay procedures are available for assessing whether or not an agent can act as an inhibitor of proteinase activity. For example, a protein substrate can be used that generates a detectable signal when cleaved by the proteinase. In some embodiments, the activity of a matrix metalloproteinase in the presence and absence of a test inhibitor is assayed by observing enzymatic hydrolysis of fluoresceinated protein substrate, for example, as a function of time. One example of such a fluoresceinated protein substrate is fluoresceinated collagen available from Molecular Probes, Inc. Such a fluoresceinated protein substrate can be incubated with a selected matrix metalloproteinase, or a mixture of selected matrix metalloproteinases. Cleavage of the fluoresceinated protein substrate is detected by observing an increase in absorbance over time. Varying amounts of substrate and/or test polypeptide inhibitor(s) can be used in the assay mixture to ascertain what concentration effects exist, and what amounts of inhibitor are optimal for inhibiting matrix metalloproteinases.

The sequence of the present polypeptides can therefore be altered to modulate the affinity of the polypeptide inhibitor for different matrix metalloproteinases. Because some proteinase activity is required (even in chronic wounds) in order to modulate extracellular matrix reorganization (Agren 1999), in certain embodiments it may be desirous to construct an inhibitor that does not inhibit matrix metalloproteinases with an extremely low $K_i$. For example, the $K_i$ values of the present polypeptides can vary from about 1 μM to about 1 mM. Such a polypeptide would have the ability to allow some transient matrix metalloproteinase activity (due to a relatively high $K_i$).

The inhibitory constant (Ki) of a polypeptide inhibitor ([I]) can be determined using procedures provided by Segel (1993) via the use of Dixon plots (1/v vs. [I]), such that:

$$\text{slope} = Km/(V\max Ki[S]) \quad (1)$$

where Km is the Michaelis constant, Vmax is the reaction maximum velocity, and [S] is the substrate concentration. The degree and the timing of inhibitor activity in the chronic wound can also be controlled by modulating the inhibitor dose and application timing.

The toxicity of the polypeptide inhibitors of the invention is expected to be low. However, if concerns arise, the cellular toxicity can be assayed by adding various amounts of a polypeptide to fibroblasts or keratinocytes in culture. The growth and cellular integrity of these cells can be monitored to assess whether a selected polypeptide inhibitor has any negative effects.

The healing rate of a selected polypeptide inhibitor can be assessed by introducing the selected polypeptide into a wound and measuring whether the healing rate is altered by the presence of the polypeptide. For example, the rate of wound healing in the presence and absence of a polypeptide can be determined. While any wound may be used, a wound model with predictable properties is preferred. For example, two animal chronic wound models exist that may be used. The first is an ischemic rabbit ear model, while the second is an induced diabetic rat model.

Polypeptide Modifications

The invention also contemplates modifying the polypeptide inhibitors to stabilize them, to facilitate their uptake and absorption and to improve any other characteristic or property of the polypeptides that is known to one of skill in art. For example, the polypeptide inhibitors can be cyclized, charges on the polypeptide inhibitors can be neutralized, and the polypeptides can be linked to other chemical moieties.

The variety of reactions between two side chains with functional groups suitable for forming such linkages within the polypeptide or to other moieties, as well as reaction conditions suitable for forming such linkages, will be apparent to those of skill in the art. Desired reaction conditions are sufficiently mild so as not to degrade or otherwise damage the polypeptide. Suitable groups for protecting the various functionalities as necessary are well known in the art (see, e.g., Greene & Wuts, 1991, 2nd ed., John Wiley & Sons, NY), as are various reaction schemes for preparing such protected molecules.

In one embodiment the charges at the N-terminal and C-terminal ends are effectively removed. This can be done by any method available to one of skill in the art, for example, by acetylating the N-terminus and amidating the C-terminus.

Methods for preparing and modifying polypeptides in a variety of ways are well-known in the art (see, e.g., Spatola, 1983, Vega Data 1(3) for a general review); Spatola, 1983, "Peptide Backbone Modifications" In: Chemistry and Biochemistry of Amino Acids Peptides and Proteins (Weinstein, ed.), Marcel Dekker, New York, p. 267 (general review); Morley, 1980, Trends Pharm. Sci. 1:463–468; Hudson et al., 1979, Int. J. Prot. Res. 14:177–185 (—CH$_2$NH—, —CH$_2$CH$_2$—); Spatola et al., 1986, Life Sci. 38:1243–1249 (—CH$_2$—S); Hann, 1982, J. Chem. Soc. Perkin Trans. I. 1:307–314 (—CH═CH—, cis and trans); Almquist et al., 1980, J. Med. Chem. 23:1392–1398 (—COCH$_2$—); Jennings-White et al., Tetrahedron. Lett. 23:2533 (—COCH$_2$—); European Patent Application EP 45665 (1982) CA:97:39405 (—CH(OH)CH$_2$—); Holladay et al., 1983, Tetrahedron Lett. 24:4401–4404 (—C(OH)CH$_2$—); and Hruby, 1982, Life Sci. 31:189–199 (—CH$_2$—S—).

Wound Healing Compositions

Polypeptides of the invention can be used to heal wounds and are particularly beneficial for chronic wound healing. Individual polypeptides, polypeptide variants, polypeptide derivatives and mixtures thereof (e.g. those with different sequences) can be combined in a formulation to promote wound healing and to prevent or treat skin problems. Optimal healing and skin regeneration may require some matrix metalloproteinase activity. Hence, the compositions and formulations of the present invention do not necessarily promote maximal inhibition of matrix metalloproteinases. Instead, the activity of the polypeptide inhibitor formulation is varied as needed to optimize healing and promote healthy skin development. Lesser or greater levels of inhibition can be achieved by varying the type, content and amount of inhibitor polypeptides so that healing and healthy skin development is promoted.

To promote healthy skin development and/or treat wounds, polypeptides of the invention are introduced onto the skin or into wounds in any manner chosen by one of skill in the art. For example, polypeptides can be formulated into a therapeutic composition containing a therapeutically effective amount of one or more polypeptides and a pharmaceutical carrier. Such a composition can be introduced onto skin or into the wound as a cream, spray, foam, gel or in any other form or formulation. In another embodiment, polypeptides of the invention can be formulated into a skin covering or dressing containing a therapeutically effective amount of one or more polypeptides impregnated into, covalently attached or otherwise associated with a covering or dressing material. In one embodiment, the skin covering or dressing permits release of the polypeptide inhibitor. Release of the polypeptide inhibitor can be in an uncontrolled or a controlled manner. Hence, the skin coverings or wound dressings of the invention can provide slow or timed release of the polypeptide inhibitor into a wound. Skin coverings and dressing materials can be any material used in the art including bandage, gauze, sterile wrapping, hydrogel, hydrocolloid and similar materials.

A therapeutically effective amount of a polypeptide of the invention is an amount of polypeptide that inhibits a matrix metalloproteinase to a degree needed to promote healthy skin development and/or wound healing. For example, when present in a therapeutic or pharmaceutical composition, the amount of polypeptides of the invention can be in the range of about 0.001% to about 35% by weight of the composition. The polypeptides can form about 0.5% to about 20% by weight of the composition. Alternately, the polypeptides form about 1.0% to about 10% by weight of the composition. The therapeutically effective amount of polypeptide inhibitor necessarily varies with the route of administration. For example, a therapeutic amount between 30 to 112,000 μg per kg of body weight can be effective for intravenous administration. However, the amount of the polypeptide inhibitor required for healthy skin development or wound treatment will vary not only with the route of administration, but also the nature of the condition being treated and the age and condition of the patient and will be ultimately at the discretion of the attendant physician or clinician.

The dosage and method of administration can vary depending upon the location of the skin or tissue to be treated and/or upon severity of the wound. Useful dosages of the polypeptides and polypeptide conjugates can be determined by correlating their in vitro activity, and in vivo activity in animal models described herein. The compound can conveniently be administered in unit dosage form; for example, containing about 0.001 μg to about 10 mg, conveniently about 0.01 μg to about 5 mg, more conveniently, about 0.10 μg to about 1 mg, and even more conveniently about 1.0 μg to 500 μg of polypeptide per unit dosage form. The desired dose may be presented in a single dose, as divided doses, or as a continuous infusion. The desired dose can also be administered at appropriate intervals, for example, as two, three, four or more sub-doses per day. One of skill in the art can readily prepare and administer an effective formulation from available information using the teachings provided herein.

The polypeptide inhibitors of the invention can be formulated as pharmaceutical compositions and administered to a mammalian host, such as a human patient in a variety of dosage forms adapted to the chosen route of administration, i.e., orally or parenterally, by intravenous, intramuscular, topical or subcutaneous routes.

Thus, the polypeptide inhibitors may be systemically administered, for example, intravenously or intraperitoneally by infusion or injection. Solutions of the polypeptide inhibitor can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion or topical application can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In some cases, one of skill in the art may choose to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the polypeptide or polypeptide conjugate in the required amount in the appropriate solvent with various of the other ingredients enumerated above, as required, followed by filter sterilization. In the case of sterile powders for the preparation of sterile injectable solutions, methods of preparation include vacuum drying and the freeze-drying techniques, which yield a powder of the active ingredient plus any additional desired ingredient present in the previously sterile-filtered solutions.

In some instances, the polypeptide inhibitors can also be administered orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the polypeptide inhibitor may be combined with one or more excipients and used in the form of ingestible tablets, buccal tablets, troches, capsules, elixirs, suspensions, syrups, wafers, and the like. Such compositions and preparations should contain at least 0.1% by weight of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the polypeptide inhibitor may be incorporated into sustained-release preparations and devices.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

In general, the polypeptides of the invention are administered topically for wound treatment and for promoting healthy skin development. The active polypeptides may be administered topically by any means either directly or indirectly to the selected tissue as sprays, foams, powders, creams, jellies, pastes, suppositories or solutions. The term paste used in this document should be taken to include creams and other viscous spreadable compositions such as are often applied directly to the skin or spread onto a bandage or dressing. Polypeptides of the invention can be covalently attached, stably adsorbed or otherwise applied to a skin covering or wound dressing material. To facilitate healing after surgery, the active polypeptides of the invention can be applied directly to target tissues or to prosthetic devices or implantable sustained released devices. The compositions can be administered by aerosol, as a foam or as a mist, with or without other agents, directly onto the skin or wound.

The polypeptides can be administered in a formulation that can include an emulsion of the polypeptide in a wax, oil, an emulsifier, water, and/or a substantially water-insoluble material that forms a gel in the presence of water. The formulation provides the desirable properties of an emulsion, in that it is spreadable and has the creamy consistency of an emulsion, yet that does not break down when subjected to normal sterilization procedures, e.g. steam sterilization, because the gel stabilizes the emulsion. It also exhibits better water retention properties than a conventional gel because water is held both in the emulsion and in the gel.

The formulation can also contain a humectant to reduce the partial vapor pressure of the water in the cream or lotion to reduce the rate at which the cream or lotion dries out. Suitable humectants are miscible with water to a large extent and are generally suitable for application to the skin. Polyols are especially suitable for the purpose and suitable polyols may include monopropylene glycol or glycerin (glycerol). The polyol may be present in proportions of 20–50% (by weight) of the total formulation; alternatively the range is 30–40%. This relatively high proportion of polyol also ensures that if the paste should dry out to any degree, the resulting paste remains soft and flexible because the glycerin may act as a plasticiser for the polymer. When the paste is applied on a bandage, for example, it may therefore still be removed easily from the skin when the paste has lost water without the need to cut the bandage off. The polyol also has the advantage of functioning to prevent the proliferation of bacteria in the paste when it is in contact with the skin or wound, particularly infected wounds.

The formulation can include other ingredients such as antibacterial agents, antifungal agents, anti-inflammatory agents, and the like. Other ingredients may also be found suitable for incorporation into the formulation.

An example of a wax for the emulsion is glyceryl monostearate, or a combination of glyceryl monostearate and PEG100 stearate that is available commercially as CITHROL GMS/AS/NA from Croda Universal Ltd. This combination provides both a wax and an emulsifier (PEG 100 stearate) that is especially compatible with the wax, for forming an emulsion in water. A second emulsifier can be included in the formulation to increase the stability of the emulsion, for example, a PEG20 stearate, such as CITHROL 1OMS that is supplied by Croda Universal Ltd. The total concentration of emulsifier in the cream should normally be in the range of from 3–15%. Where two emulsifiers are used, one may be present in a greater concentration than the other.

The water-insoluble material forms a gel with the water of the formulation. The material is therefore hydrophilic but does not dissolve in water to any great extent. The material can be a polymeric material, for example, a water-absorbing non water-soluble polymer. However, non-polymeric materials that form gels with water and that are stable at elevated temperatures could also be used, e.g. clays such as kaolin or bentonite. Some polymers used in the invention are superabsorbent polymers such as those disclosed in WO-92/16245 and that comprise hydrophilic cellulose derivatives that have been partially cross-linked to form a three dimensional structure. Suitable cross-linked cellulose derivatives include those of the hydroxy lower alkyl celluloses, wherein the alkyl group contains from 1 to 6 carbon atoms, e.g. hydroxyethyl cellulose or hydroxypropylcellulose, or the carboxy-celluloses e.g. carboxymethyl hydroxyethyl cellulose or carboxy methylcellulose. An example of a polymer that may be used in the invention is a partially cross-linked sodium carboxy methylcellulose polymer supplied as AKU-CELL X181 by Akzo Chemicals B.V. This polymer is a superabsorbent polymer in that it may absorb at least ten times its own weight of water. The cross-linked structure of the polymer prevents it from dissolving in water but water is easily absorbed into and held within the three-dimensional structure of the polymer to form a gel. Water is lost less rapidly from such a gel than from a solution and this is advantageous in slowing or preventing the drying out of the cream formulation. The polymer content of the formulation is normally less than 10%, for example, the polymer content can range from about 0.5 to about 5.0% by weight, or from about 1.0% to about 2% by weight.

The formulation may be sterilized and components of the formulation should be selected, by varying the polymer content, to provide the desired flow properties of the finished product. That is, if the product to be sterilized, then the formulation should be chosen to give a product of relatively high viscosity/elasticity before sterilization. If certain components of the formulation are not to be sterilized, the formulation can be sterilized before addition of those components, or each component can be sterilized separately. The formulation can then be made by mixing each of the sterilized ingredients under sterile conditions. When components are separately sterilized and then mixed together, the polymer content can be adjusted to give a product having the desired flow properties of the finished product. The emulsion content determines the handling properties and feel of the formulation, higher emulsion content leading to increased spreadability and creaminess.

The formulation may be packaged into tubes, tubs or other suitable forms of containers for storage or it may be spread onto a substrate and then subsequently packaged. Suitable substrates include dressings, including film dressings, and bandages.

The following examples are intended to illustrate but not limit the invention.

EXAMPLE 1

Procedures

This Example provides the materials and methods employed for various experiments.

Molecular Biology Procedures: Bacterial growth conditions and culturing were performed as described by Miller (1972). Unless otherwise noted all procedures performed in this study were according to Maniatis et al. (1982) or Sambrook et al. (1989) or Sambrook et al. (2001); including, agarose gel electrophoresis, and restriction endonuclease digestions. Vent DNA polymerase used in all PCR reactions was purchased from New England Biolabs and was used with the supplied buffer. DNA sequencing (Sanger et al., 1977) was performed using an Applied Biosystems, Inc. automated sequencer, and was performed by Genosys, Inc. DNA oligonucleotides were synthesized by Genosys, Inc. Protein concentration was determined according to the method of Bradford (1976) using bovine serum albumin (BSA) as a standard or spectrophotometrically using a calculated molar absorption coefficient of 11,300 $M^{-1}$ $cm^{-1}$. Analytical gel filtration experiments were performed according to Siegel and Monty (1966) using a 7×250 mm BioSelect SEC-125 column from BioRad, Inc. All bacterial strains were purchased from the New England Biolabs, Inc. Protein SDS PAGE gels were made, run, and processed as per Laemmli (1970). Chemical reagents and chromatography resins were from Sigma Chemical Co. (St. Louis, Mo.), except where specifically noted.

Molecular modeling. Molecular modeling utilized two visualization programs, Swiss PDB Viewer (Guex and Peitsch, 1997) and Rasmol (Sayle and Milner-White, 1995). Model work was performed on a Compaq PC running Windows 95, as well as a Silicon Graphics, Inc. Octane UNIX workstation. Additionally, the Cerius2 molecular package from Molecular Simulations, Inc. was utilized on the Octane. Three dimensional structure files of selected matrix metalloproteinases (MMPs) were downloaded from the Protein Databank as follows (filename, reference): MMP-1 (1FBL, Li et al., 1995), MMP-2 (1GEN, Libson et al., 1995), MMP-8 (1JAO, 1JAN, Grams, et al., 1995; Reinemer et al., 1994), MMP-9 (1MMQ, Browner et al., 1995), TIMP-2/ MT-1 MMP complex (1BUV, Fernandez-Catalan et al., 1998), TIMP-2 (1BR9, Tuuttila et al., 1998), and TIMP-1/MMP complex (1UEA, Gomis-Ruth et al., 1997; Huang et al., 1996; Becker et al., 1995). These files were used to analyze the three-dimensional structure of the proteins, the chemical nature of amino acids at various positions and the identification of conserved and variant amino acids in the MMP-TIMP contact interface. This information was utilized to design the inhibitors of the invention that would bind many matrix metalloproteinase enzymes.

The first step was to begin with a full-length amino acid sequence that was an average of the four known TIMP sequences. A robust pair wise alignment of the four TIMP amino acid sequences was calculated using the program CLUSTAL (Higgins et al., 1992). A consensus sequence was then constructed based on this alignment. For non-conserved amino acids in the contact region, substitutions were made that preserved the hydrophobic character of the vicinity, but that negated specific sidechain-sidechain interactions. Through this exercise, a consensus binding interface was obtained. The large flexible loop portion of TIMP-2, that is not evident in TIMP-1, was built back into the polypeptide inhibitor with several amino acid sequence changes.

The second step was to remove the C-terminal domain of the consensus inhibitor molecule. Through the analysis of the two TIMP/MMP complex structures, it was determined that only the N-terminal TIMP region made significant contact with the catalytic domain of the MMP. This was confirmed later by docking the final protein model with MMP-9. This manipulation also reduced the overall length of the protein from 225 amino acids to 108 amino acids. In order to stabilize the new C-terminus of the protein, two additional amino acid replacements were made: Leu85 and Val101 were changed to cysteine. These two residues were observed to be within 3 Å of each other. Hence, substitution with cysteine would likely permit formation of a disulfide bond. In this way the last loop region of the protein would be locked in place. In addition a cysteine residue in position 13 was changed to serine. Thus six cysteine residues were available in the final protein inhibitor to participate in disulfide bond formation.

The third step entailed building a homology model of the new protein inhibitor. The final 108 amino acid sequence of the inhibitor was threaded onto the alpha carbon trace of TIMP-2 using the programs ProMod and SwissModel (Peitsch, 1996; Peitsch et al., 1996). This model was then subjected to energy minimization using a GROMOS 96 forcefield, and several rounds of molecular mechanics geometry optimization using the SYBYL forcefield (Clark et al., 1989). The final minimized/optimized model was then analyzed for bad side chain interactions and torsional geometry.

The finalized polypeptide inhibitor derived from such three-dimensional modeling had SEQ ID NO:5 and was designated DST. This acronym is short for Delta (the final protein has the C-terminal TIMP domain deleted) Synthetic (it is based on structural and homology modeling) TIMP (because it is based on TIMP1–2 structures).

Gene design, construction, and cloning: The final SEQ ID NO:5 amino acid sequence was back translated using the standard genetic code. Codon choice was based on *E. coli* codon bias, meaning that the final codon selected for a particular amino acid was the most frequently used codon for that amino acid in *E. coli*. The full-length structural gene was 327 bp. In order to build the gene sequence, ten single-stranded oligonucleotides that spanned the coding region were synthesized by Genosys, Inc. The oligonucleotides were 70 nucleotides in length. Each oligonucleotide was complementary to another oligonucleotide, such that when hybridized with its binding partner, the resulting fragment contained a central duplex region of 50 base pairs and was flanked on each end by a 10 nucleotide single-stranded region. The oligonucleotide sequences employed are shown in Table 4.

TABLE 4

Oligonucleotides for construction of the inhibitor nucleic acid

| | |
|---|---|
| 1: ATGTGCAGCT GCAGCCCGGT GCATCCGCAG CAGGCGTTTA GCAACGCGGA TGTGGTGATT CGCGCGAAAG-3' | (SEQ ID NO:8) |
| 2: CGGTGAGCGA AAAAGAAGTC GATAGCGGCA ACGATATTTA TGGCAACCCG ATTAAACGCA TTCAGTATGA-3' | (SEQ ID NO:9) |
| 3: AATTAAACAG ATTAAAATGT TTAAAGGCCC GGAAAAAGAT ATTGAATTTA TTTATACCGC GCCGAGCAGC-3' | (SEQ ID NO:10) |
| 4: GCGGTGTGCG GCGTGAGCCT GGATGTGGGC GGCAAAAAAG AATATTGCAT TGCGGGCAAA GCGGAAGGCG-3' | (SEQ ID NO:11) |
| 5: ATGGCAAAAT GCATATTACC CTGTGCGATT TTATTTGCCC GTGGTAGAAG CTTATAGAC-3' | (SEQ ID NO:12) |
| 6: TCGCTCACCG CTTTCGCGCG AATCACCACA TCCGCGTTGC TAAACGCCTG CTGCGGATGC ACCGGGCTGC AGCTGCACAT-3' | (SEQ ID NO:13) |
| 7: CTGTTTAATT TCATACTGAA TGCGTTTAAT CGGGTTGCCA TAAATATCGT TGCCGCTATC GACTTCTTTT-3' | (SEQ ID NO:14) |
| 8: CGCACACCGC GCTGCTCGGC GCGGTATAAA TAAATTCAAT ATCTTTTTCC GGGCCTTTAA ACATTTTAAT-3' | (SEQ ID NO:15) |
| 9: ATTTTGCCAT CGCCTTCCGC TTTGCCCGCA ATGCAATATT CTTTTTTGCC GCCCACATCC AGGCTCACGC-3' | (SEQ ID NO:16) |
| 10: GTCTATAAGC TTCTACCACG GGCAAATAAA ATCGCACAGG GTAATATGC-3' | (SEQ ID NO:17) |
| 11: ATGTGCAGCTGCAGCCCGGT-3' | (SEQ ID NO:18) |
| 12: GTCTATAAGC TTCTACCACG-3' | (SEQ ID NO:19) |

The construction of the inhibitor nucleic acid (SEQ ID NO:6) was done in three separate steps.

First, 5 μg of each oligonucleotide and its complementary binding partner (for five separate reactions) were mixed together in 10 mM Tris-HCl (pH 7.2), 10 mM NaCl in a final volume of 10 μL. The specific oligonucleotide used in the hybridization mixtures were (see Table 4): (1 and 6), (2 and 7), (3 and 8), (4 and 9), and (5 and 10). The mixture was heated in a water bath at 95° C. for 10 minutes. The heat was turned off, and the entire water bath was allowed to cool to room temperature over a period of five hours.

Second, aliquots (10 μL) from each of the five "slow cool" reactions were mixed together (final volume 50 μL). The tube was heated at 45° C. for 10 minutes and then was placed into an ice bath. T4 DNA ligase and buffer (New England Biolabs) were added to the tube, and the reaction (final volume 60 μL) was incubated at 16° C. for 20 hours.

Third, the full-length nucleic acid having SEQ ID NO:6 was selected from the mixture of fragments using two PCR primers (Table 4, 11 and 12) that were complimentary to the extreme 5' and 3' ends of the structural gene. This step ensured that only full-length nucleic acids would be amplified. In addition the 3' amplification primer contained a Hind III site to facilitate cloning. The PCR reaction was performed using 1 μL of the ligation mixture described in the foregoing paragraph. The PCR conditions employed were as follows: 95° C., 1 minute; 49° C., 1 minute; 72° C., 30 seconds. Thirty cycles of this program were performed in a Techne Progene PCR device. A ten minute 72° C. extension incubation was performed after the last PCR cycle. The PCR reaction product was verified by DNA agarose gel electrophoresis.

The PCR reaction product was purified via a Promega DNA Wizard PCR clean-up kit. Prior to cloning, the DNA fragment was treated with T4 DNA polymerase in the presence of ATP in order to ensure fully duplex ends. This reaction was performed according to the instructions from New England Biolabs, Inc. The DNA was re-purified using the Promega DNA Wizard PCR clean-up kit. Then the DNA was digested with Hind III and was purified by ethanol precipitation. The final DNA was resuspended in a small volume of 10 mM Tris-HCl (pH 8.0), 1 mM EDTA.

The cloning vector, pMAL-c2 (New England Biolabs), was digested with Xmn I and Hind III, and was purified using the Promega DNA clean-up kit. This digest produced a linear vector that contained a 3' blunt end and a 5' Hind III end that was compatible with the 5' blunt end and the 3' Hind III end of the DNA fragment. This combination ensured directional, in-frame cloning of the SEQ ID NO:6 DNA fragment. The vector and the SEQ ID NO:6 DNA fragment were mixed in approximately 1:10 molar ratio and were ligated together in the presence of T4 DNA ligase at 16° C. for 20 hours (total reaction volume was 20 μL). Competent JM109 bacteria were transformed with 5 μL of the ligation reaction. After growth on LB with 60 μg/mL ampicillin agar plates, single colonies were selected, and plasmid was purified from the colonies by the miniprep procedure using a Promega miniprep DNA isolation kit. Isolated plasmids were evaluated by DNA agarose gel electrophoresis, restriction endonuclease digestion, and finally by DNA sequencing. The plasmid construct that encoded the SEQ ID NO:5 polypeptide was designated pDSTe.

Purification of the protein inhibitor: The expression strategy utilized the T4 RNA polymerase over-expression system from New England Biolabs, Inc. The vector used for protein expression was pMAL, which contains the gene sequence for the maltose binding protein upstream of a multiple cloning site. The SEQ ID NO:6 nucleic acid was inserted into this multiple cloning site. A 1% innoculum of TB-1 cells containing the SEQ ID NO:6 expression vector were grown at 37° C. in Luria broth supplemented with 1% glucose and 60 μg/mL ampicillin. IPTG was added to a final concentration of 0.5 mM when the cells had reached an $A_{595}$ value of 0.8 (at approximately three hours post-inoculation). Cell growth continued for five additional hours before harvesting. Typically, 5 g of cells was obtained per liter.

Cells were pelleted by centrifugation at 10,000×g for ten minutes and resuspended in one volume of 10 mM Tris-HCl, pH 8.0. The cells were respun as above and were frozen for at least 2 hours at −70° C. The frozen pellet was resuspended in two volumes of BPER E. coli protein extraction buffer. The mixture was incubated at 30° C. for 20 minutes with occasional mixing. The resulting extract was clarified by centrifugation at 12,000×g for 20 minutes, and the supernatant was dialyzed against 20 mM Tris-HCl (pH 7.4), 200 mM NaCl, 1 mM EDTA (Buffer I). The dialyzed material was diluted to a final concentration of 2.5 mg/mL with Buffer I, and was designated as Fraction I. All subsequent chromatography steps were performed at room temperature.

Fraction I was applied to a 10 cm×7.6 cc² amylose resin column that had previously been equilibrated with Buffer I. The column was then washed extensively with Buffer I (usually 10 column volumes) to remove unbound material. The bound fusion protein was eluted from the column by the application of Buffer I, 10 mM maltose. A typical elution volume was about 2 column volumes. Fractions were assayed for protein content spectrophotometrically, and protein-containing fractions were pooled. This material was designated as Fraction II. Protein concentration was adjusted to 1 mg/mL via Centricon (Amicon, Inc.).

Fraction II was mixed with Factor Xa protease at a weight/weight stoichiometry of 100:1 (typical reactions contained 50 mg of fusion protein and 0.5 mg of Factor Xa). Cleavage reactions proceeded at room temperature for 24 hours. The extent of cleavage was monitored by SDS PAGE analysis of aliquots removed at various time points during the reaction. The final mixture was dialyzed versus 20 mM Tris-HCl (pH8.0), 25 mM NaCl, 3 mM EDTA and was designated as Fraction III.

Fraction III was applied to a Mono Q ion exchange column (6 cm×7.6 cc²) that had been equilibrated in 10 mM Tris-HCl (pH 8.0), 25 mM NaCl (Buffer II). The column was run as follows: Buffer II, 30 mLs; Buffer II with a linear gradient from 25 mM to 500 mM NaCl, 40 mLs. Maltose binding protein eluted from the column in 125 mM NaCl, the homogeneous protein inhibitor eluted in 250 mM NaCl, and the Factor Xa protease eluted in 400 mM NaCl. Fractions containing the protein inhibitor were pooled. The material was dialyzed against Buffer II, concentrated to 10 mg/mL, and was designated as Fraction IV. The protein was stored in aliquots at −20° C. All subsequent experiments were performed with Fraction IV protein, unless specifically noted. The purified SEQ ID NO:5 protein was designated DST.

Inhibition of MMPs: The assay employed measured the enzymatic hydrolysis of fluoresceinated collagen by MMP-9 or other matrix metalloproteinases as a function of time. Fluoresceinated collagen at a concentration of 5 μM was added to reaction buffer (50 mM Tris-HCl (pH 7.6), 150 mM NaCl, 5 mM $CaCl_2$, 0.1 mM $NaN_3$) and was placed into a Spectrosil quartz fluorimeter cuvette. MMP at a concentration of 0.1 μM was mixed with varying amounts of polypeptide inhibitor (SEQ ID NO:5 or SEQ ID NO:20) and incubated at 25° C. for 10 minutes in order to effect binding. The protein mixture was added to the collagen substrate, and mixed. Fluorescence emission intensity at 520 nm was measured as a function of time using an excitation wavelength of 495 nm in a Shimadzu RF5301 fluorimeter. The fluorescein release assay was used to determine the inhibitory constant ($K_i$) of the protein based matrix metalloproteinase inhibitor ([I]) according to Segel (1993) by using Dixon plots (1/v vs. [I]), where:

$$\text{slope} = K_m / (V_{max} K_i [S]) \qquad (1)$$

where $K_m$ is the Michaelis constant, $V_{max}$ is the reaction maximum velocity, and [S] is the substrate concentration.

Production of polyclonal antibodies: Polyclonal anti-sera was produced by Genosys, Inc. Polyclonal antibodies (pAb) directed against the SEQ ID NO:5 polypeptide were induced by subcutaneous injection of homogeneous SEQ ID NO:5 polypeptide (300 μg) in a 1:1 homogenate with Freund's complete adjuvant into female New Zealand White rabbits. Three subsequent injections of antigen (200 μg) with incomplete adjuvant were performed at weekly intervals. One week after the last injection, the rabbits were bled via an ear cannula. The cleared plasma was collected by centrifugation at 14,000×g and stored at −20° C. until use.

Purification of Polyclonal Antibodies:

The pAbs were purified to homogeneity by affinity chromatography on DEAE Affi-gel Blue. A rabbit polyclonal antibody isolation kit from BioRad Labs, Inc. was employed according to the supplied instructions, with several minor modifications. The protocol is as follows: The cleared rabbit serum (5 mLs) was passed over an Econo-Pac 10DG desalting column. The pAbs were eluted from the column using the supplied running buffer (0.02 M Tris HCl (pH 8.0), 0.028 M NaCl), and were collected as a single fraction. At this stage the protein concentration was determined using the Bradford assay. The entire serum sample (usually 25 mLs) was passed over the column in 5 mL batches. Between batches the column was washed with 40 mL of running buffer (two column volumes). The final desalted samples from the individual column runs were pooled. This pooled sample was applied to the DEAE Affi-gel Blue column as a single load, the column was washed with 5 column volumes of running buffer (50 mLs), and the pAb fraction was eluted from the column by the application of 5 column volumes of elution buffer (0.025 M Tris HCl (pH 8.0), 0.025 M NaCl). The eluted material was collected as 5 mL fractions. The purity of the IgG fraction was estimated by SDS PAGE. Appropriate fractions were pooled, concentrated to 2 mg/mL by pressure filtration, and were stored at −70° C. until needed. The DEAE Affi-gel Blue column was regenerated by washing the column with 2 M NaCl, 1.5 M sodium thiocyanate in running buffer (10 column volumes), followed by re-equilibration in running buffer. The flow rate for all chromatography steps was maintained at 1.0 mL/min.

ELISA analysis: ELISAs were performed using methods described by Kaiser and Pollard, (1993) or by Quirk et al. (1996). One µg of purified SEQ ID NO:5 or SEQ ID NO:20 polypeptide was adsorbed to the surface of a 96-well microtiter plate (Immulon 2, Dynatech Labs). The wells were blocked with phosphate buffered saline (PBS) supplemented with 10% BSA. Polyclonal antibodies in blocking buffer were added at various dilutions and were allowed to react with the bound polypeptide inhibitor at room temperature for one hour. Following three washes in PBS, visualization was achieved via a goat anti-rabbit secondary antibody that is conjugated with horseradish peroxidase (Santa Cruz Biotechnology, Inc.). The secondary antibody was added at a 1:2000 dilution in blocking buffer and was incubated at room temperature for one hour. After three washes in PBS, color development is achieved by adding a solution containing 50 mM sodium citrate, 50 mM citric acid, 1 mg/mL o-phenylenediamine, and 0.006% $H_2O_2$. After suitable color development (typically 5 to 10 minutes of incubation at room temperature) 50 µL of 2 M sulfuric acid was added to stop the reaction and stabilize the product. Absorbance was measured at 490 nm using an automatic ELISA plate reader (Molecular Dynamics, Inc.). Alternatively, fluoresceinated goat anti-rabbit secondary antibody (Molecular Probes, Inc.) was utilized for the ELISA. For these assays, a Dynex, Inc. fluorescent microtiter plate reader was employed with a 485 nm (excitation) and a 510 nm (emission) bandpass filter set.

Intrinsic tryptophan fluorescence: Chemical denaturation Stability measurements of the protein inhibitor were performed by measuring protein unfolding in the presence of urea via intrinsic tryptophan fluorescence (Lakowicz, 1983) in a Shimadzu RF5301 fluorimeter. The excitation and emission wavelengths were 295 nm and 340 nm respectively. Both excitation and emission monochromer slits were set at 1.5 nm. Protein (20 µM) was mixed with increasing amounts of urea (in the concentration range of zero to 6.8 M), and the samples were incubated at room temperature for ten hours to ensure that unfolding equilibrium had been achieved. Relative fluorescence was converted into free energy values according to the relation (Pace et al., 1989):

$$\Delta G = -RT \ln [(y_f - y_i)/(y_i - y_u)] \quad (2)$$

where $y_f$ and $y_u$ are the relative fluorescence values for fully folded and fully unfolded SEQ ID NO:5 polypeptide respectively, $y_i$ is the relative fluorescence of the unfolding intermediates, T is the absolute temperature, and R is the gas constant. Linear regression and extrapolation of the relationship $\Delta G$ versus [urea] was employed to determine the free energy value in the absence of denaturant ($\Delta G_{H2O}$). Similarly, the fraction unfolded protein ($F_u$) was calculated from the fluorescence data according to the relation (Pace et al., 1989):

$$F_u = (y_f - y_i)/(y_f - y_u) \quad (3)$$

Thermal Denaturation.

The intrinsic tryptophan fluorescence of homogeneous SEQ ID NO:5 polypeptide in 25 mM Tris-HCl (pH 8.5), 50 mM NaCl was measured in a Shimadzu RF5301 fluorimeter (excitation wavelength 295 nm, emission wavelength 340 nm). Temperature was controlled via a stirred water-jacketed sealed quartz fluorimeter cuvette connected to a digital water bath that was accurate to +/−0.1° C. Dry nitrogen gas was flushed through the sample compartment continuously to control condensation. Temperature changes were made at a rate of 0.2° C. per minute. The sample was allowed to incubate at temperature for five minutes prior to reading the fluorescence in order to ensure that the system had come to thermal equilibrium. The fluorescence values determined from the thermal experiments were normalized using equation (3) above. The calculated $F_u$ values were converted into the equilibrium constant ($K_D$) using the following equation (4):

$$K_D = (1 - F_u)/F_u \quad (4)$$

By setting $\ln K_D = 0$, the following van't Hoff equation (5) can be utilized to calculate the values of the transition temperature ($T_m$) and the corresponding enthalpy at the transition temperature ($\Delta H_m$) (Arnold and Ulbrich-Hofmann, 1997):

$$d(\ln K_D)/d(1/T) = -\Delta H/R \quad (5)$$

If $\Delta G$ is set to zero in the Gibbs equation, then the entropy at the transition temperature ($\Delta S_m$) can be calculated as follows:

$$\Delta S_m = \Delta H_m/T_m \quad (6)$$

Free energy values for the transition temperature region were calculated from the following equation:

$$\Delta G = -RT \ln K_D \quad (7)$$

These free energy values were substituted into the Gibbs-Helmholtz equation (8) in order to compute the heat capacity.

$$\Delta G = \Delta H_m (1 - T/T_m) - \Delta C_p [(T_m - T) + T \ln(T/T_m)] \quad (8)$$

Finally, the temperature of maximum stability ($T_{max}$) was calculated according to the following equation (9):

$$T_{max} = T_m \exp [-\Delta H_m/\Delta C_p T_m] \quad (9)$$

Surface Plasmon Resonance: The BiaCore, Inc: BiaCore-X surface plasmon resonance (SPR) device was utilized to measure the interaction between SEQ ID NO:5 polypeptide (also called the DST protein) and matrix metalloproteinase-9 (MMP-9). For these experiments a carboxymethyl dextran sensor chip (CM-5, Lofas et al., 1993) was activated with 50 mM N-hydroxysuccinimide, 0.2 M N-ethyl-N'-(dimethylaminopropyl)-carbodiimide at a flow rate of 10 µL per minute for ten minutes. SEQ ID NO:5 polypeptide at a concentration of 75 ng/µL was coupled to the activated surface at a flow rate of 10 µL per minute for ten minutes. The final surface was inactivated by flowing 1 M ethanolamine-HCl at a rate of 10 µL per minute for five minutes over the sensor surface. MMP-9 was flowed over the sensor surface at a rate of 20 µL per minute, and at concentrations that ranged from 1 to 100 nM. Binding isotherms were evaluated by simultaneously fitting the forward ($k_a$) and reverse ($k_d$) rate constants to:

$$d[DST\sim MMP\text{-}9]/dt = (k_a[DST][MMP\text{-}9]) - (k_d [DST\sim MMP\text{-}9]) \quad (10)$$

(Karlsson and Falt, 1997) where [DST], [MMP-9], and [DST~MMP-9] are the concentrations of free SEQ ID NO:5 polypeptide (DST), free MMP-9, and the complex respectively. The equilibrium affinity constant ($K_A$) is then defined as:

$$K_A = k_a/k_d \quad (11)$$

Equation 10 is properly expressed in terms of the SPR signal (Morton et al., 1995) as:

$$dR/dt = k_a C R_{max} - (k_a C + k_d) R \qquad (12)$$

where R is the SPR signal (in response units, RU) at time t, $R_{max}$ is the maximum MMP-9 binding capacity in RU, and C is the SEQ ID NO:5 polypeptide concentration. Kinetic analysis (O'Shannessy et al., 1993) was performed using Origin from Microcal, Inc.

EXAMPLE 2

Polypeptide Inhibitor Properties

Molecular Cloning

Molecular visualization analysis of matrix metalloproteinase (MMP) and MMP~TIMP three dimensional structures provided structural information for design of the SEQ ID NO:5 polypeptide. The final amino acid sequence of the SEQ ID NO:5 protein can bind a variety of matrix metalloproteinase molecules. The SEQ ID NO:6 nucleic acid that encodes the SEQ ID NO:5 polypeptide employs the codon bias of E. Coli in order to maximize expression.

Construction of the 327 nucleotide SEQ ID NO:6 sequence required a series of short oligonucleotides, because it is currently very difficult to construct nucleic acids that are over 100 bases in length. In addition, it is difficult to efficiently hybridize longer nucleic acid molecules. Hence construction was carried out using a series of hybridization steps. When mixed together in equimolar amounts, the individual oligonucleotides (SEQ ID NO:8–19) were efficiently converted into duplex molecules by a "slow cool" hybridization step. Slowly reducing the temperature from 95° C. over a period of hours favored the formation of short duplexes.

The resulting fragments contained a central double stranded region of 50 to 60 base pairs that were flanked by 10 nucleotide single-stranded termini. These "sticky ends" were used to drive the assembly of the full-length nucleic acid, again by hybridization. The full-length nucleic acid was formed by heating an equimolar mixture of the duplex molecules at 45° C. for 10 minutes. This step disrupted any partially formed duplex structures formed by association of the termini, but would not disrupt the fully formed central duplex regions. The heated material was "quick cooled" by placing the reaction tube on ice. This hybridization step favored the hybridization of short regions of DNA (i.e.—the 10 base sticky ends). Closure of the phosphodiester backbone of the 327 bp DNA fragment was performed by use of the enzyme T4 DNA ligase.

The full-length nucleic acid was selected from the resulting mixture of fragments by PCR amplification. This step was far more efficient than purifying the full-length nucleic acid from agarose gels. This step also resulted in a large amount of material for subsequent cloning steps. The ends of the SEQ ID NO:6 nucleic acid were prepared for cloning by making one end blunt using T4 DNA polymerase and using Hind III on the other end to generate a Hind III-compatible end. This resulted in a DNA molecule that could be efficiently and directionally cloned into protein expression vectors.

FIG. 1 shows the result of this cloning. Three out of nine examined colonies contained vector with the correct insert (SEQ ID NO:6). The validity of the insert was confirmed by DNA sequencing; several clones had a sequence corresponding to SEQ ID NO:6.

Physical Properties of the SEQ ID NO:5 Polypeptide

Figure 2:
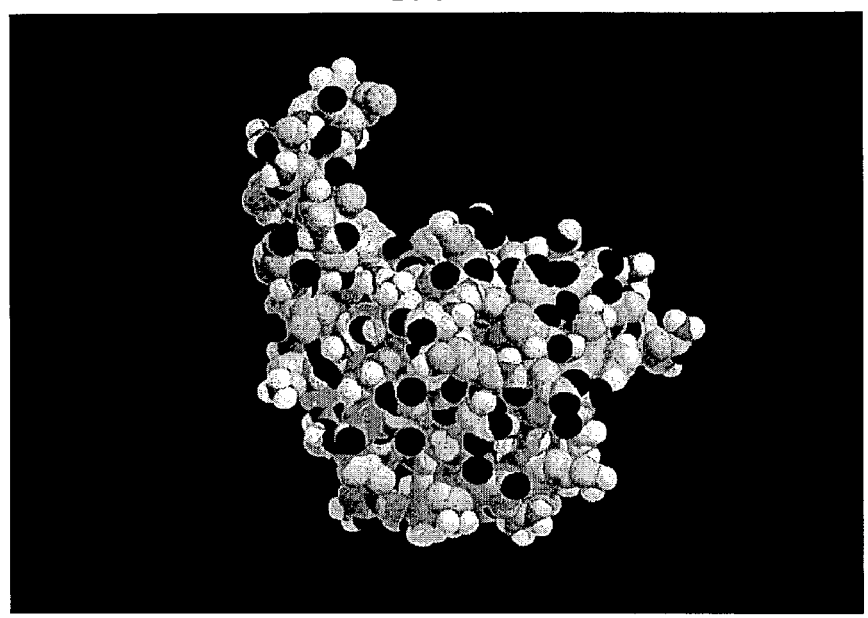
FIG. 2 provides a photocopy of a molecular visualization of a final energy minimized model for the SEQ ID NO:5 polypeptide.
Figure 2:
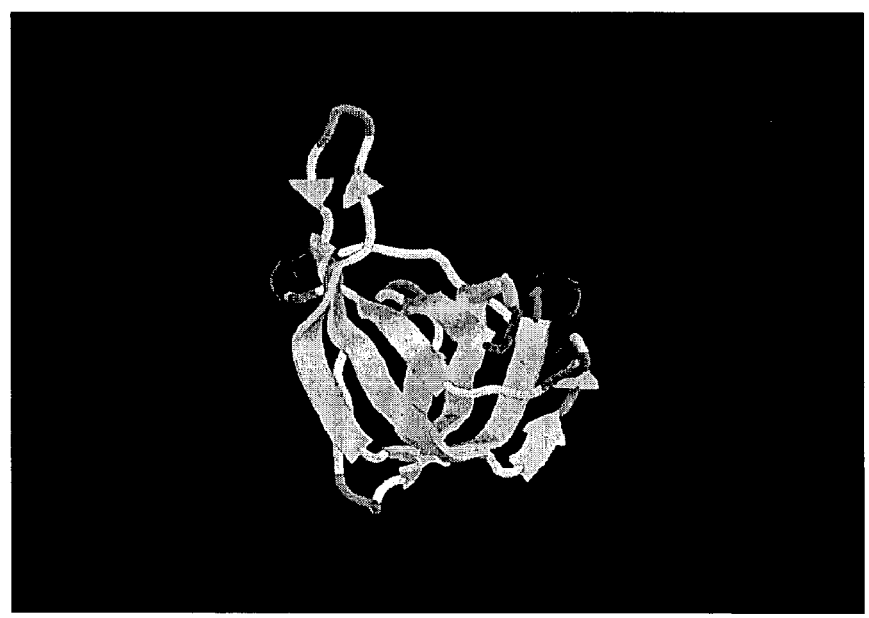

The SEQ ID NO:5 polypeptide protein is 108 amino acids in length and has a total molecular weight of 108 kDa. A three dimensional model of SEQ ID NO:5 polypeptide was prepared by threading the SEQ ID NO:5 sequence onto the three dimensional alpha carbon backbone of TIMP-2 using the program SwissModel. The optimal thread result was converted into a three dimensional structure that included amino acid side chain positions using the program ProMod. This initial model was subjected to a round of simulated annealing in order to minimize side chain clashes. Several rounds of a SYBYL level geometry optimization put all dihedral angles and torsions into proper geometry. A final round of energy minimization using a GROMOS96 parameter set, without a reaction field was employed. These results are shown in Table 5. The final model has an overall energy of −3534 kJ/mol and is shown in FIG. 2. All amino acid residues are within allowable Ramachandran space (data not shown) and there are no steric clashes.

TABLE 5

GROMOS 96 energy minimization results for the homology model (only the major parameters from the forcefield are shown).

| Parameter | Energy (kJ/mol) |
| --- | --- |
| Bonds | 66 |
| Angles | 541 |
| Torsions | 667 |
| Impropers | 103 |
| Nonbonded | −3027 |
| Electrostatic | −1884 |
| Constraints | 0 |
| Total: | −3534 |

Several properties of the SEQ ID NO:5 polypeptide are shown in Table 6.

TABLE 6

Miscellaneous properties of the SEQ ID NO: 5 polypeptide.

| | |
| --- | --- |
| Length (amino acids): | 108 |
| Molecular weight: | 11.8 |
| Isoelectric point: | 6.5 |
| Hydrophobic (%): | 39.8 |
| Hydrophilic (%): | 33.3 |
| Basic (%): | 13.9 |
| Acidic (%): | 13.0 |
| Stokes radius (Å): | 22 |
| Frictional coefficient: | 1.2 |
| Alpha helix (%): | 9 |
| Beta Strand (%): | 62 |
| Loop/coil (%): | 29 |
| Tryptophan (#): | 1 |
| Tyrosine (#): | 4 |

The single designed-in tryptophan greatly aided in intrinsic fluorescence experiments (see below). The protein was designed as a single polypeptide that forms a six-stranded beta barrel (FIG. 2). The top region of the molecule forms a molecularly flat structure that is held together in part by the formation of two disulfide bonds, between residues Cys2–Cys73 and Cys4–Cys102. (FIG. 2). This region forms the basis of the binding domain. This area is flanked by a TIMP-2 like arm formed by a flexible loop region spanning residues Ser31 to Lys41. The loop is stabilized to the main structure by a series of hydrogen bonds. The flexible loop may act as a TIMP recognition domain, and molecular dynamics simulations (data not shown) indicate that it is highly mobile, with deflections that exceed 4 Å. The molecular dimensions of the SEQ ID NO:5 polypeptide are approximately 21×18×25 Å (total molecular volume of 9455 Å³, total solvent accessible surface area of 9867 Å²).

Expression in *E. coli*

Amino acid sequencing of the amino terminal end of purified SEQ ID NO:5 polypeptide revealed that the N-terminal methionine is removed in *E. coli* as a post-translational modification. Such removal of the N-terminal methionine yields a polypeptide with the following sequence (SEQ ID NO:20).

```
  1  CSCSPVHPQ QAFSNADVVI RAKAVSEKEV DSGNDIYGNP

41  IKRIQYEIKQ IKMFKGPEKD IEFIYTAPSS AVCGVSLDVG

81  GKKEYCIAGK AEGDGKMHIT LCDFICPW
```

Purification

The purification of the SEQ ID NO:5 or SEQ ID NO:20 polypeptide from *E. coli* resulted in approximately 5 mg of protein per liter of induced culture. The purification regime outlined in Table 7 took approximately three days to complete. The SEQ ID NO:5/SEQ ID NO:20 polypeptide is overproduced approximately 27-fold in *E. coli*. Although in the course of the purification trial, the SEQ ID NO:5/SEQ ID NO:20 polypeptide was visualized solely by SDS PAGE analysis, it was also useful to define a unit of activity. This calculation helps to assess the SEQ ID NO:5/SEQ ID NO:20 polypeptide yield and helps quantify activity.

Figure 3:
FIG. 3 illustrates the purification of the SEQ ID NO:5 polypeptide as assessed by 12% SDS PAGE analysis of the maltose binding protein (MBP)-SEQ ID NO:5 polypeptide fusion and the purified SEQ ID NO:5 polypeptide. The expression and purification of the protein followed the protocol described in Example 1. Lane 1, approximately 5 µg of the MBP-SEQ ID NO:5 polypeptide fusion (Fraction II); Lane 2, approximately 10 µg of purified (Fraction IV) SEQ ID NO:5 polypeptide. The gel was visualized with coomassie stain.
Figure 3:
Figure 4:
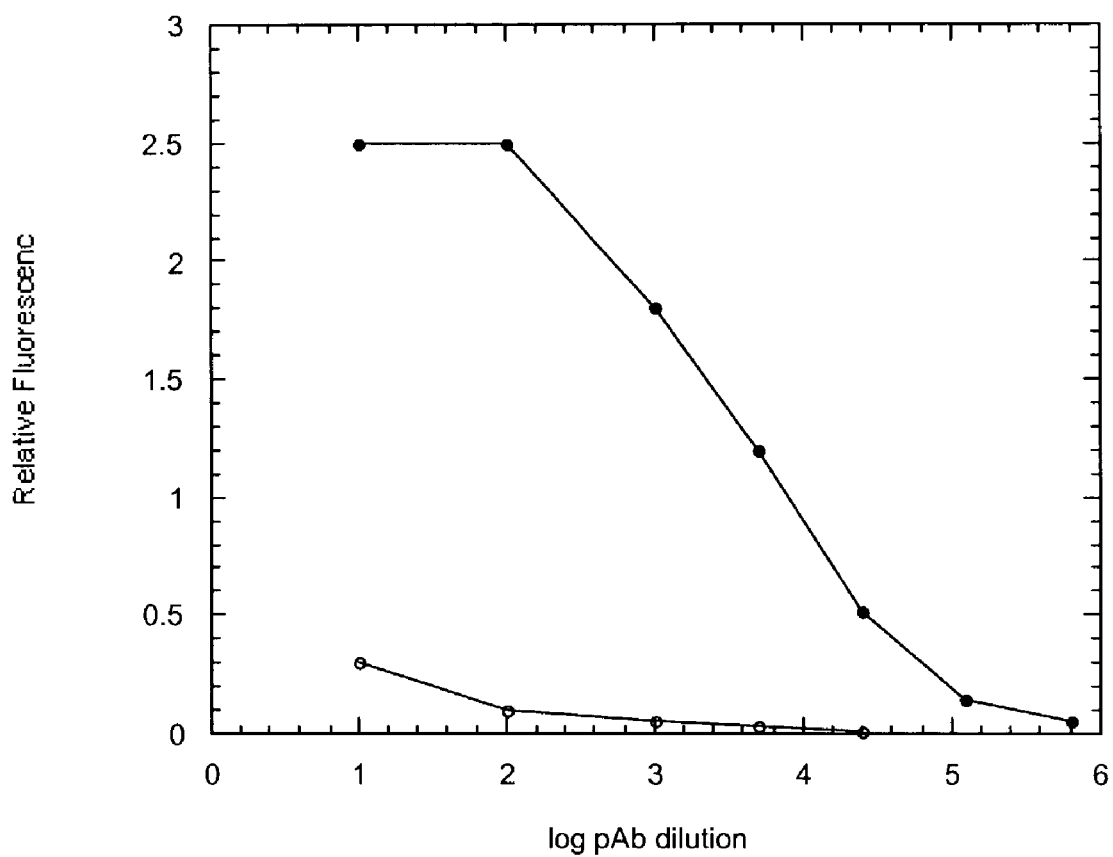
FIG. 4 provides a graph summarizing an ELISA analysis of polyclonal antibodies (pAbs) raised against the SEQ ID NO:5 polypeptide. One µg of Fraction IV the SEQ ID NO:5 polypeptide was adsorbed to the wells of a microtiter tray and reacted with either purified pAbs (filled circles) or pre-immune serum (open circles) at the indicated dilution. Visualization was achieved using a goat anti-rabbit secondary antibody that was labeled with Oregon Green-488. A Dynex fluorescent microtiter plate reader was utilized with a 485 nm (excitation) and a 538 nm (emission) bandpass filter set. The fluorescence versus the log of the antibody (or serum) dilution is plotted in this graph.

The purification scheme is aided by the fact that the SEQ ID NO:5/SEQ ID NO:20 protein is isolated from bacteria as a maltose binding protein (MBP) fusion. Since MBP has a high solubility and affinity for amylose, it is straightforward to express and purify the protein. Preparation of the crude bacterial extract is efficiently achieved by chemical lysis of the bacteria followed by clearing the lysate via centrifugation. The fusion protein was therefore purified to homogeneity in a single step (FIG. 3, lane 1). Treatment of this complex with the protease Factor Xa, resulted in full cleavage of the fusion product in approximately 12 hours. There was no detectable proteolysis of the SEQ ID NO:5/SEQ ID NO:20 protein. The final chromatographic step using MonoQ ion exchange efficiently separated MBP, the SEQ ID NO:5 (SEQ ID NO:20) polypeptide, and Factor Xa. FIG. 3 (lane 2) shows the final preparation of homogeneous SEQ ID NO:5/SEQ ID NO:20 polypeptide after elution from the MonoQ column.

was obtained that readily detects purified SEQ ID NO:5 polypeptide in ELISA reactions (FIG. 4). These antibodies can be used to detect and to track the SEQ ID NO:5 polypeptide when it is introduced into chronic wound environments. The antibody pool routinely detected the SEQ ID NO:5 polypeptide using dilutions of approximately 1:5,000.

Matrix Metalloproteinase Inhibition

Figure 5:
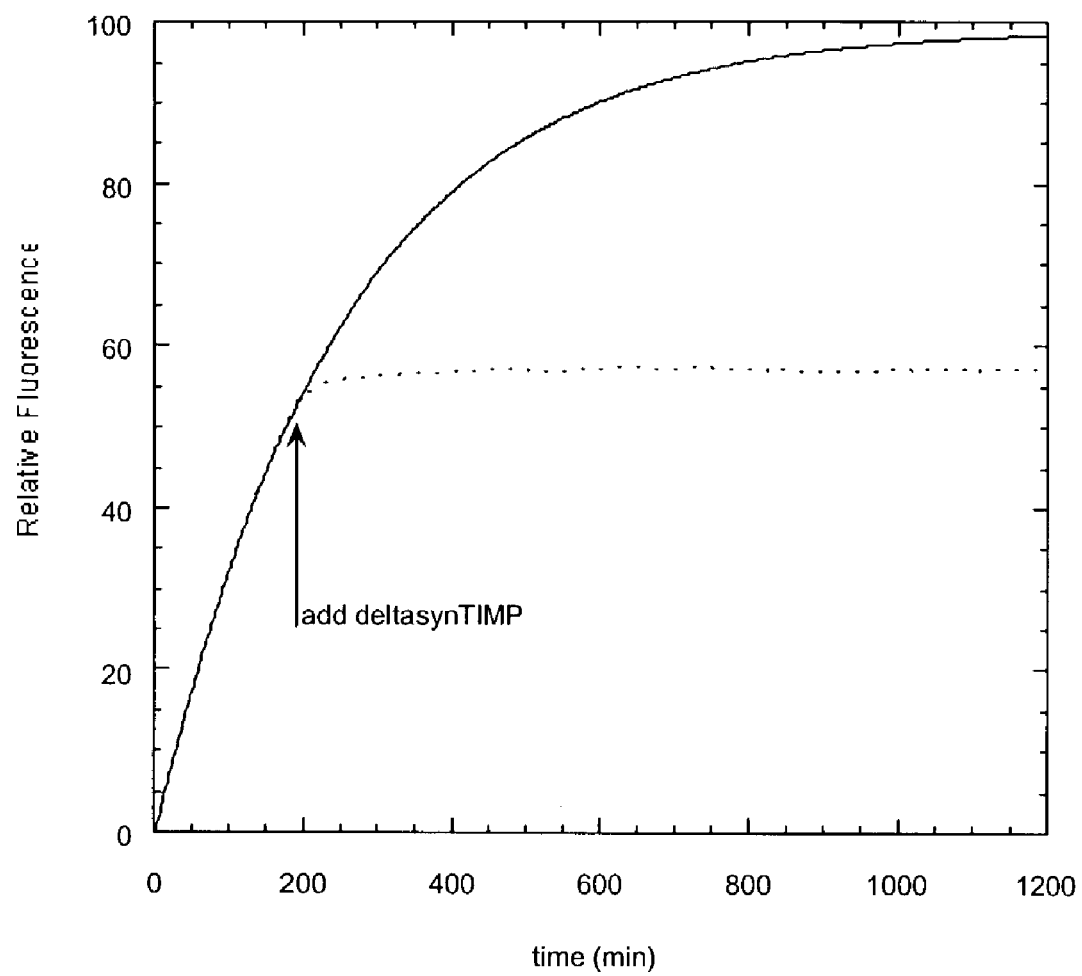
FIG. 5 provides a graph illustrating the enzymatic hydrolysis of fluoresceinated collagen by matrix metalloproteinase-9. The assay measured the release of fluorescein from collagen as a function of time. Substrate was mixed with enzyme at time zero, and collagen destruction was monitored for 1200 seconds (bold line). In a separate reaction an equal amount of the SEQ ID NO:5 polypeptide was added to an ongoing hydrolysis reaction at 200 seconds (the arrow on the graph). The dotted line below indicates that after a short lag period, collagen destruction ceased. Excitation wavelength at 490 nm, emission wavelength at 520 nm.

The SEQ ID NO:5 polypeptide effectively inhibited the hydrolysis of fluorescinated collagen by MMP-9. When the protein was added to an ongoing enzymatic reaction (FIG. 5), 98% of collagen hydrolysis ceased within a 45 second lag period. Titrating MMP-9 with increasing amounts of the SEQ ID NO:5 polypeptide (FIG. 6) resulted in loss of MMP-9 hydrolytic activity in a concentration dependent manner. These data indicated that the inhibition reaction is stoichiometric, an observation that was further confirmed in later experiments (see below).

Figure 6:
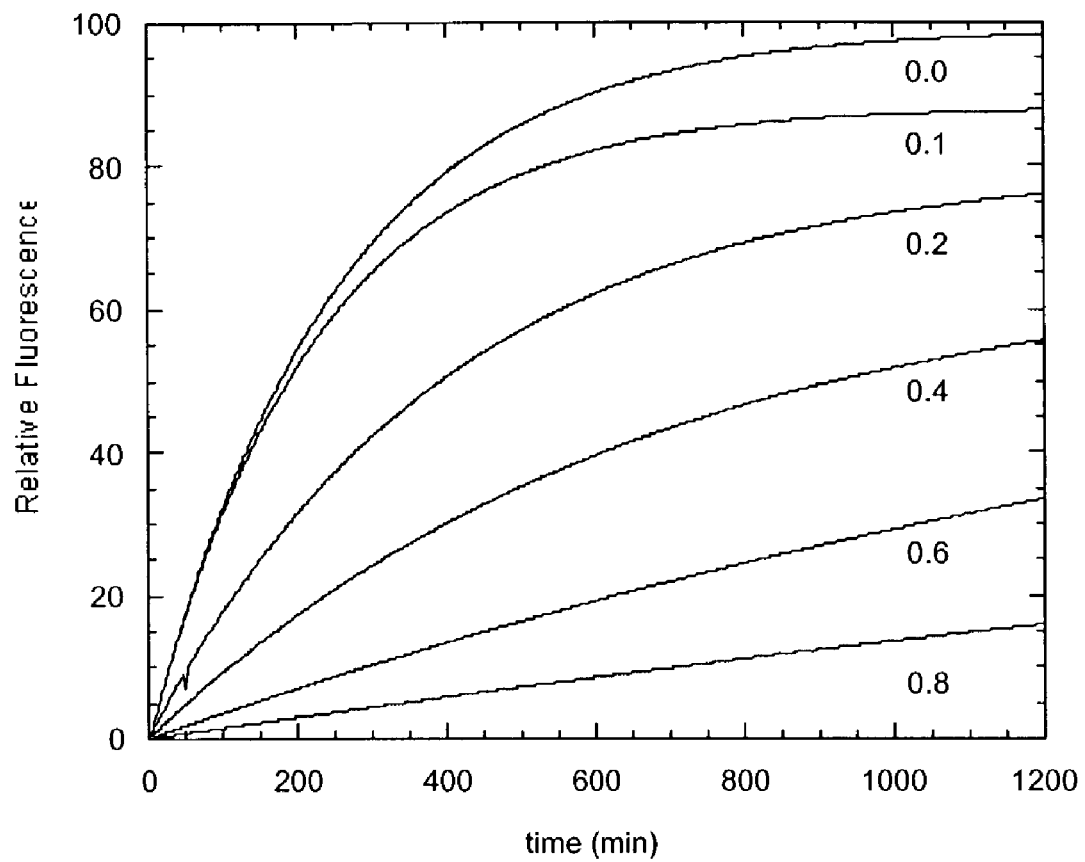
FIG. 6 provides a graph illustrating a titration of matrix metalloproteinase-9 with the SEQ ID NO:5 protein. The fluorescein release assay was used to determine the kinetic parameters of inhibitor function. The indicated stoichiometric amount of the SEQ ID NO:5 polypeptide was added to matrix metalloproteinase-9, and the mixture was incubated at room temperature for 5 minutes. Fluoresceinated collagen and buffer were added to the mixture, and the release of fluorescein was monitored as a function of time. Excitation wavelength at 490 nm, emission wavelength at 520 nm.

Using kinetic data shown in FIG. 6, was possible to obtain inhibitory constants ($K_i$) for a host of MMP enzymes. The instantaneous velocities from the fluorescence vs. time plots were used to construct linear Dixon plots, from which it was possible to solve for $K_i$ directly. This analysis assumes that the SEQ ID NO:5 polypeptide functions through a competitive inhibitor mechanism.

Figure 7:
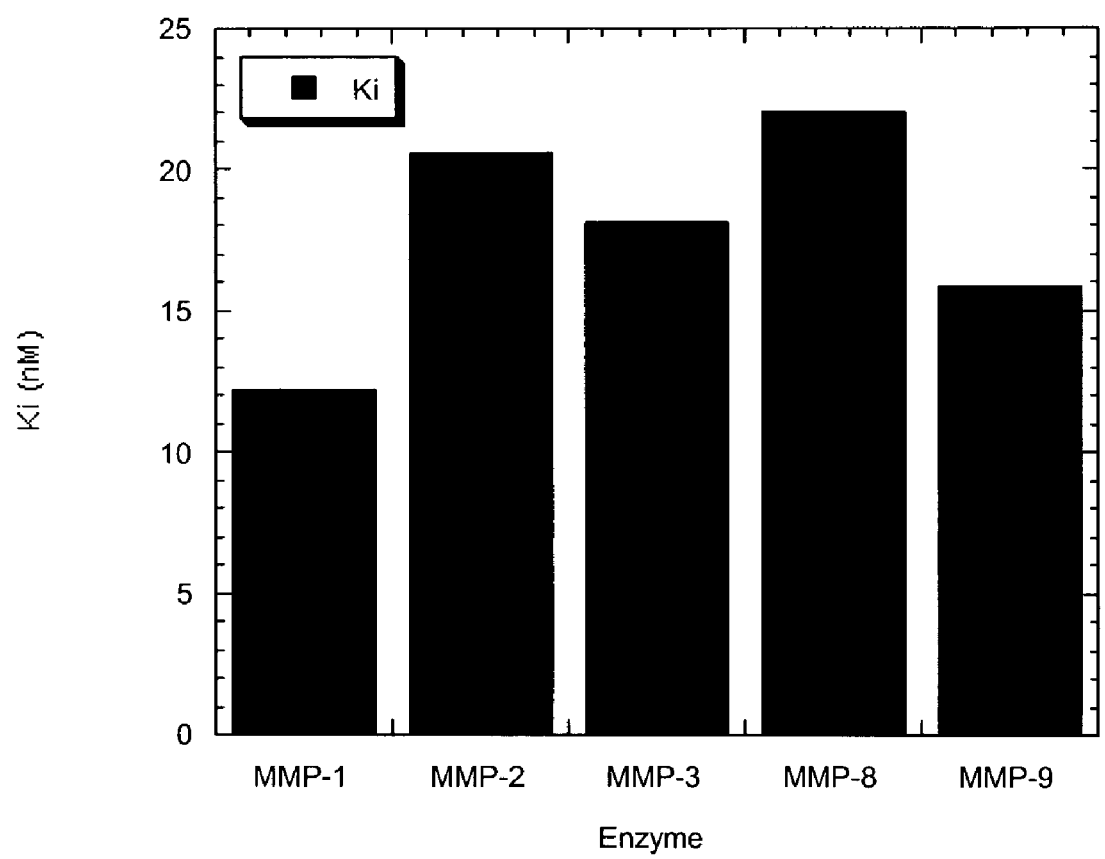
FIG. 7 provides a bar graph illustrating the inhibitory constants for the SEQ ID NO:5 polypeptide determined for several MMPs. Instantaneous velocity values were extracted from the curves in FIG. 6, and were used to calculate $K_i$ values as described in the Procedures section.

FIG. 7 illustrates the SEQ ID NO:5 polypeptide $K_i$ values for five MMP enzymes. All the enzymes were effectively inhibited in the nanomolar range. Surprisingly, the SEQ ID NO:5 polypeptide had a lower $K_i$ value for MMP-1 than it did for MMP-9 (12 vs. 16 nM). However, the low $K_i$ values obtained for all the matrix metalloproteinases tested indicated that the SEQ ID NO:5 polypeptide is capable of preventing the enzymatic activity of all of the major MMP forms that are found in chronic wounds.

Inhibitor Stability

Figure 8:
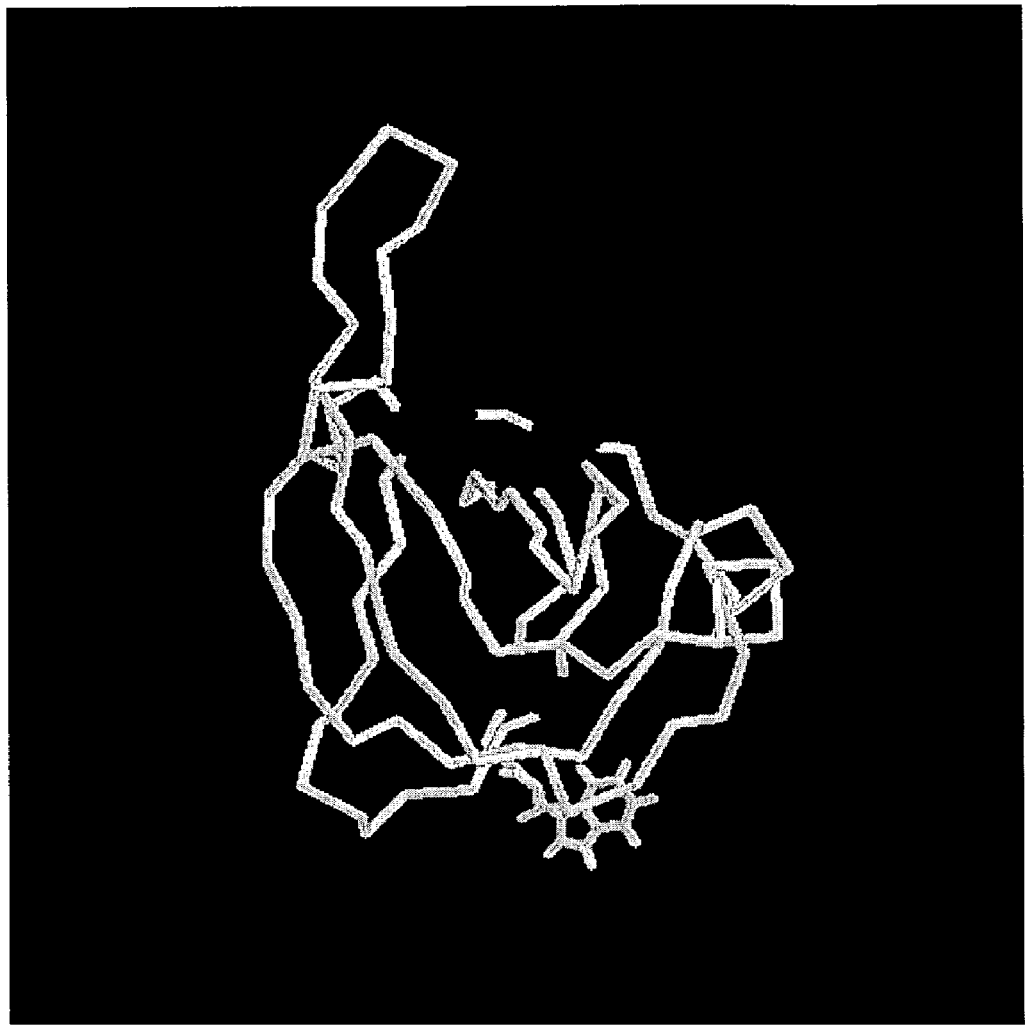
FIG. 8 provides a photocopy of a molecular visualization of the SEQ ID NO:5 polypeptide. An alpha carbon backbone trace (in light gray) highlights the position of the three-disulfide bonds (shown in dark gray). The two upper disulfide bonds help to maintain the geometry of the MMP binding region, while the lower disulfide bond helps to lock the carboxy terminus into a more rigid conformation. Also shown in light gray is the position of the single tryptophan.

FIG. 8 provides a structural model of the polypeptide backbone of the SEQ ID NO:5 polypeptide and of selected amino acid side chains. This Figure illustrates two important features of the SEQ ID NO:5 polypeptide. The first is the position of the three disulfide bonds that contribute to the stability of the molecule (see below). The second is the position of the single tryptophan molecule that is utilized as the basis for all the intrinsic fluorescence experiments.

The SEQ ID NO:5 polypeptide unfolds in a highly cooperative manner. Equilibrium unfolding monitored by intrinsic tryptophan fluorescence provided an overall 60 percent decrease in emission fluorescence intensity and a 10 nm shift in the emission peak maximum to longer wavelengths (data not shown).

TABLE 7

Purification of SEQ ID NO: 5/SEQ ID NO: 20 polypeptide
Starting material was 5 g of *E. coli*, post induction.

| Fraction | Step | Concentration (mg/mL) | Total Protein (mg) | Specific Act.[a] (units/mg) | Purification (n-fold) |
|---|---|---|---|---|---|
| I. | Crude extract | 30 | 125 | 327 | 1 |
| II. | Amylose resin | 1.0 | 25.0 | 4123 | 13 |
| III. | Factor Xa cleavage | 1.1 | 25.0 | 8322 | 25 |
| IV. | Mono Q | 10 | 5.2 | 8747 | 27 |

[a]A unit of the SEQ ID NO: 5 polypeptide is defined as the concentration of protein (in μg/mL) that is required to inhibit MMP-9 by 50% in the standard assay.

Antibody Production

Figure 9:
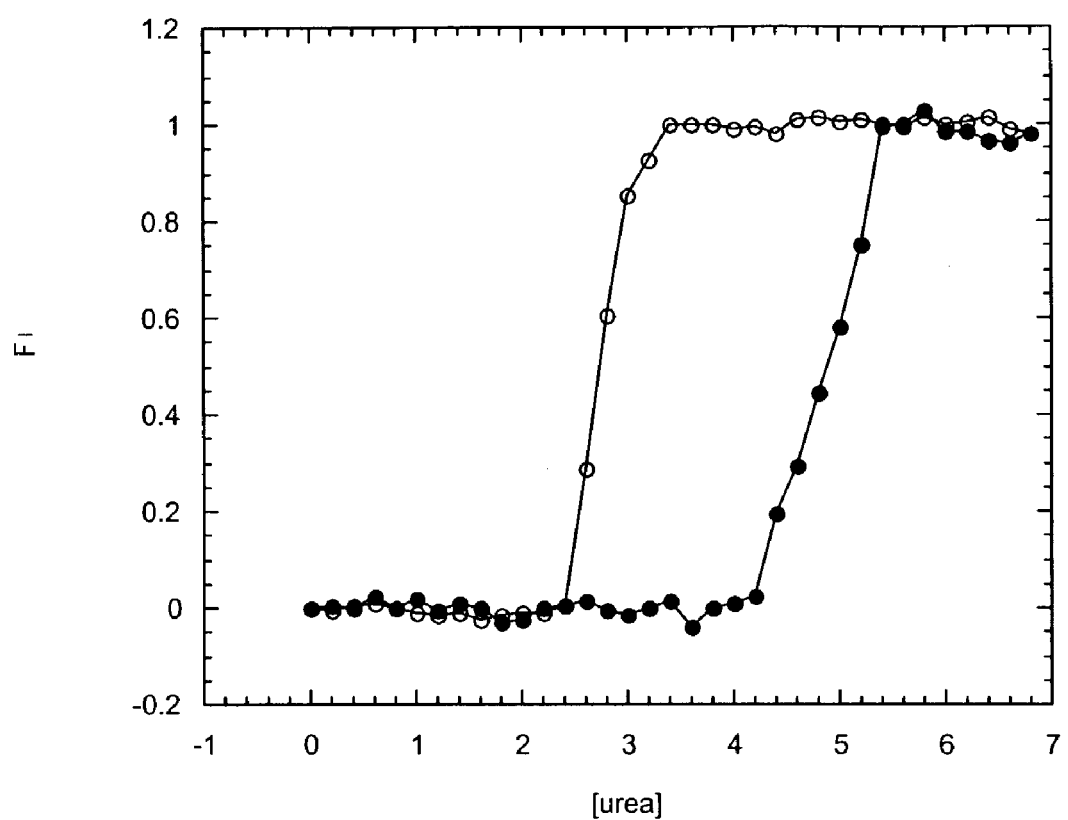
FIG. 9 provides a graph illustrating the chemical denaturation of native (filled circles) or reduced (open circles) SEQ ID NO:5 polypeptide. Plotted is the fraction of the protein population that is unfolded as a function of the urea concentration. The SEQ ID NO:5 polypeptide was reduced by incubating the protein with 1 mM DTT prior to the addition of urea. Fluorescence emission values were converted into fraction unfolded as described in the Procedures section.

Polyclonal Antisera was prepared against the SEQ ID NO:5 polypeptide in rabbits. A pool of purified antibodies Fluorescence intensity emission spectra were converted into the fraction of unfolded protein as described in Example 1. FIG. 9 shows that the midpoint in the unfolding curve for native SEQ ID NO:5 polypeptide occurred at a concentration of 4.95 M urea. The unfolding transition began at 4.4 M urea and was complete at a denaturant concentration of 5.4 M urea. The existence of a single peak in the first derivative plot of this data (not shown) supported the hypothesis that the protein denatures as a highly cooperative two state process.

Conversion of the unfolding curve into a free energy versus the concentration of urea plot (see Example 1) and extrapolation via a linear regression to the free energy in the absence of urea indicated that the polypeptide inhibitor has a native free energy of 7.4 kcal mol$^{-1}$. When the polypeptide inhibitor was reduced with dithiothreitol prior to the denaturation experiments, there was a significant loss of stability. The unfolding transition then began at 2.4 M urea and was completed at a denaturant concentration of 4.4 M urea, with a transition midpoint of 2.75 M urea. The unfolding process was still a highly cooperative, two-state process.

The reduced SEQ ID NO:5 polypeptide has a native free energy of 4.3 kcal mol$^{-1}$. Therefore the three disulfide bonds in the SEQ ID NO:5 polypeptide protein contribute approximately 3.1 kcal mol$^{-1}$ of stabilization energy.

Figure 10:
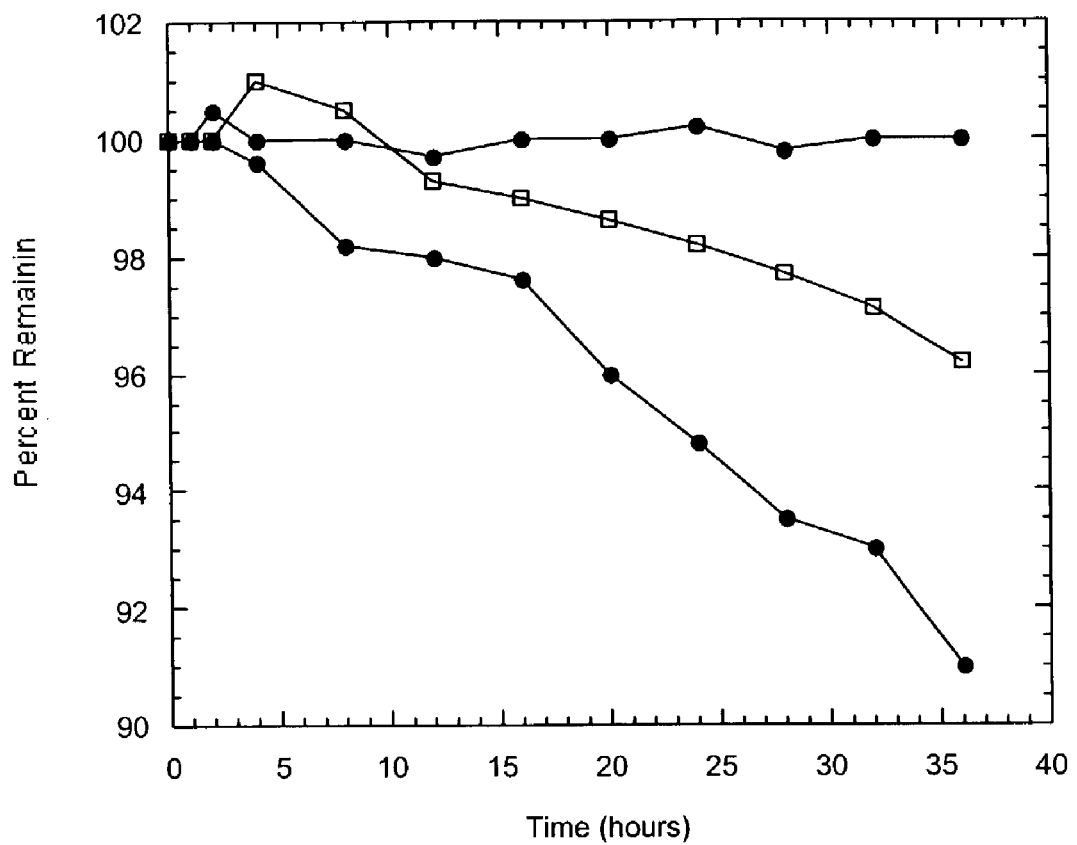
FIG. 10 provides a graph illustrating the stability of the SEQ ID NO:5 polypeptide in human serum. One mg of Fraction IV SEQ ID NO:5 polypeptide was added to 1 mL of human serum (closed circles, lower line), 1 mL of PBS (closed circles, upper line), or 0.2 mg of MMP-9 and 1 mL of human serum. The samples were incubated at room temperature. At the times indicated an aliquot was removed from the mixtures and was frozen at −20° C. until the end of the 36-hour period. The aliquots were then analyzed for the SEQ ID NO:5 polypeptide content by ELISA using purified anti SEQ ID NO:5 polypeptide pAbs. Visualization was achieved using a goat anti-rabbit secondary antibody that was labeled with Oregon Green-488. A Dynex fluorescent microtiter plate reader was utilized with a 485 nm (excitation) and a 538 nm (emission) bandpass filter set. Fluorescence was converted to percent SEQ ID NO:5 polypeptide remaining by arbitrarily setting the zero time point to 100%.

The SEQ ID NO:5 protein was long-lived in human serum. Incubation of the SEQ ID NO:5 polypeptide in human serum was performed to simulate exposure of the polypeptide to the types of fluids present in a chronic wound. Incubating the SEQ ID NO:5 polypeptide with human plasma at room temperature over the course of 36 hours resulted in only a 9 percent loss of SEQ ID NO:5 polypeptide (FIG. 10). If the SEQ ID NO:5 polypeptide is pre-bound to a stoichiometric amount of MMP-9, then only 4 percent of the material was lost over the course of the same 36 hours. A control reaction, where the SEQ ID NO:5 polypeptide was incubated in PBS, resulted in 100 percent of the material remaining after 36 hours of incubation. The stability of the SEQ ID NO:5 polypeptide was further indicated by the chemical denaturation studies. However, the serum stability indicated that the SEQ ID NO:5 polypeptide may be insensitive to protease degradation. Stability and protease resistance is important in a chronic wound environment.

Figure 11:
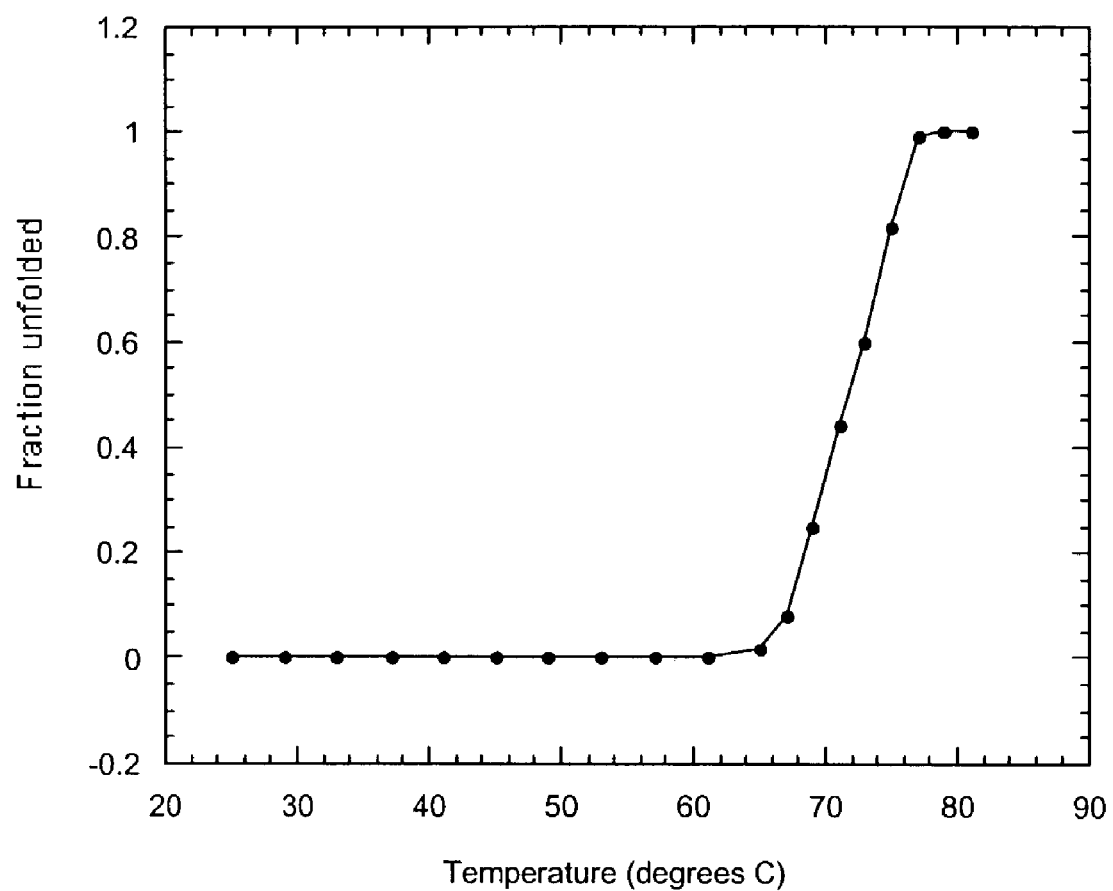
FIG. 11 provides a graph illustrating the thermal transition of 50 µM SEQ ID NO:5 polypeptide as monitored by intrinsic tryptophan fluorescence. Data were collected and analyzed as described in Example 1. The fraction of the protein population that is unfolded as a function of the temperature is plotted.

The thermal unfolding transition of the SEQ ID NO:5 polypeptide was monitored by intrinsic tryptophan fluorescence. The thermal transition curve is presented in FIG. 11. The intrinsic tryptophan fluorescence of the SEQ ID NO:5 polypeptide showed little variation between 25 and 60° C., consistent with a thermostable native conformation at temperatures below the thermal transition point. At temperatures beyond 60° C., the SEQ ID NO:5 polypeptide unfolded in a highly cooperative manner. The thermally induced structural transitions were fully reversible at the heating/cooling rates performed in this study (data not shown). The melting behavior of the SEQ ID NO:5 polypeptide was an enthalpic process rather than as an entropic process. The thermodynamic stability parameters are presented in Table 8.

TABLE 8

Thermodynamic Stability Parameters

| Parameter | Value |
|---|---|
| Chemical: | |
| $\Delta G_{nat}$ (kcal mol$^{-1}$) | 7.42 |
| $\Delta G_{red}$ (kcal mol$^{-1}$) | 4.32 |
| $\Delta \Delta G$ (kcal mol$^{-1}$) | 3.10 |
| $m_{nat}$ (cal mol$^{-1}$M$^{-1}$) | 3084 |
| $m_{red}$ (cal mol$^{-1}$M$^{-1}$) | 3112 |

TABLE 8-continued

Thermodynamic Stability Parameters

| Parameter | Value |
|---|---|
| urea$_{1/2nat}$ (M) | 4.95 |
| urea$_{1/2red}$ (M) | 2.75 |
| Thermal: | |
| $T_m$ (° C.) | 71.5 |
| $\Delta H_m$ (kcal mol$^{-1}$) | 100 |
| $\Delta S_m$ (cal mol$^{-1}$K$^{-1}$) | 250 |
| $\Delta G_{71.5°\,C.}$ (kcal mol$^{-1}$) | 1.32 |
| $\Delta G_{30°\,C.}$ (kcal mol$^{-1}$) | 6.71 |
| $T_{max}$ (° C.) | 37.8 |
| $\Delta C_p$ (kcal mol$^{-1}$K$^{-1}$) | 2.84 |

Figure 12:
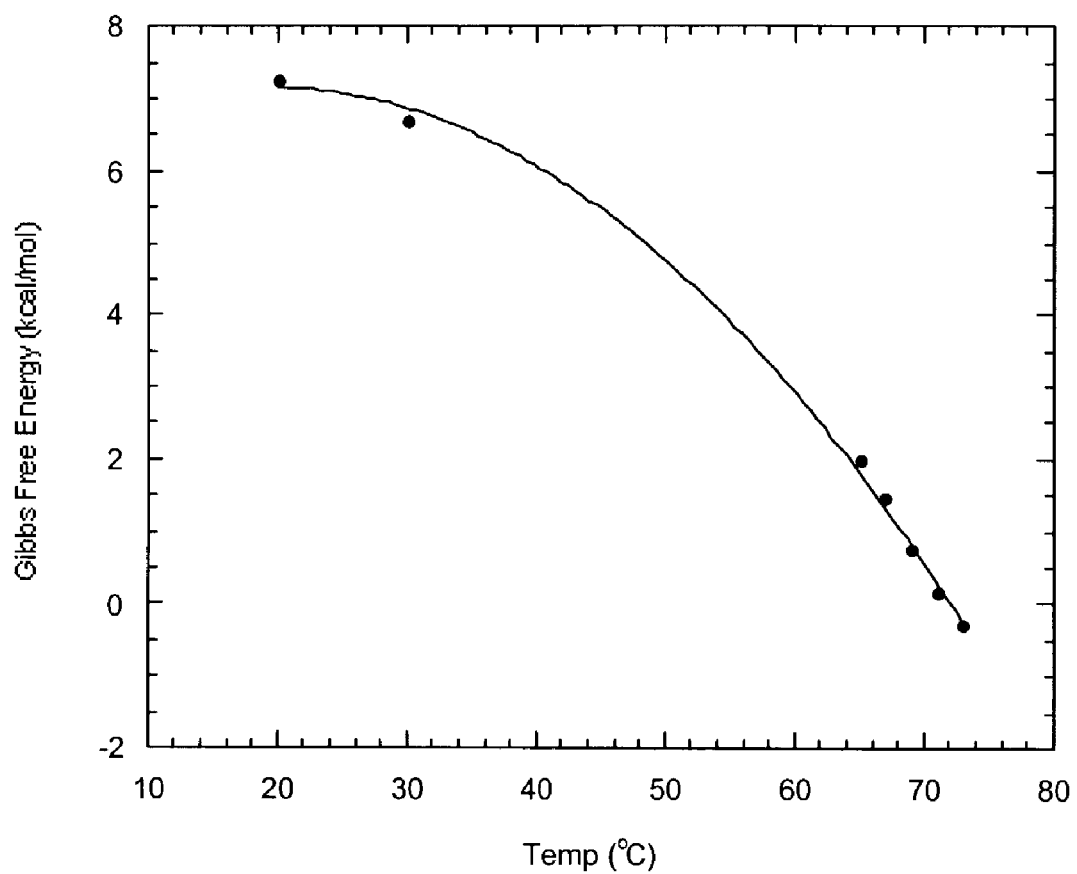
FIG. 12 provides a thermodynamic characterization of the SEQ ID NO:5 polypeptide. The graph illustrates the thermodynamic stability of the SEQ ID NO:5 polypeptide as a function of temperature as determined by intrinsic tryptophan fluorescence. Included on the plot are free energy values determined at 20° C. and 30° C. by denaturation of the protein in urea (see also FIG. 9). Free energy calculations were performed according to the method described in Example 1.

The stability of the SEQ ID NO:5 polypeptide as a function of temperature was determined using the Gibbs-Helmholtz function (eq 7), and is presented as $\Delta G$ versus temperature in FIG. 12. The $\Delta G$ values determined at lower temperatures by chemical denaturation in the presence of urea are included for comparison. These lower temperature chemical denaturation studies were also assayed by intrinsic tryptophan fluorescence (see FIG. 9). Stability differences persisted over the entire temperature range measured in this study.

Figure 13:
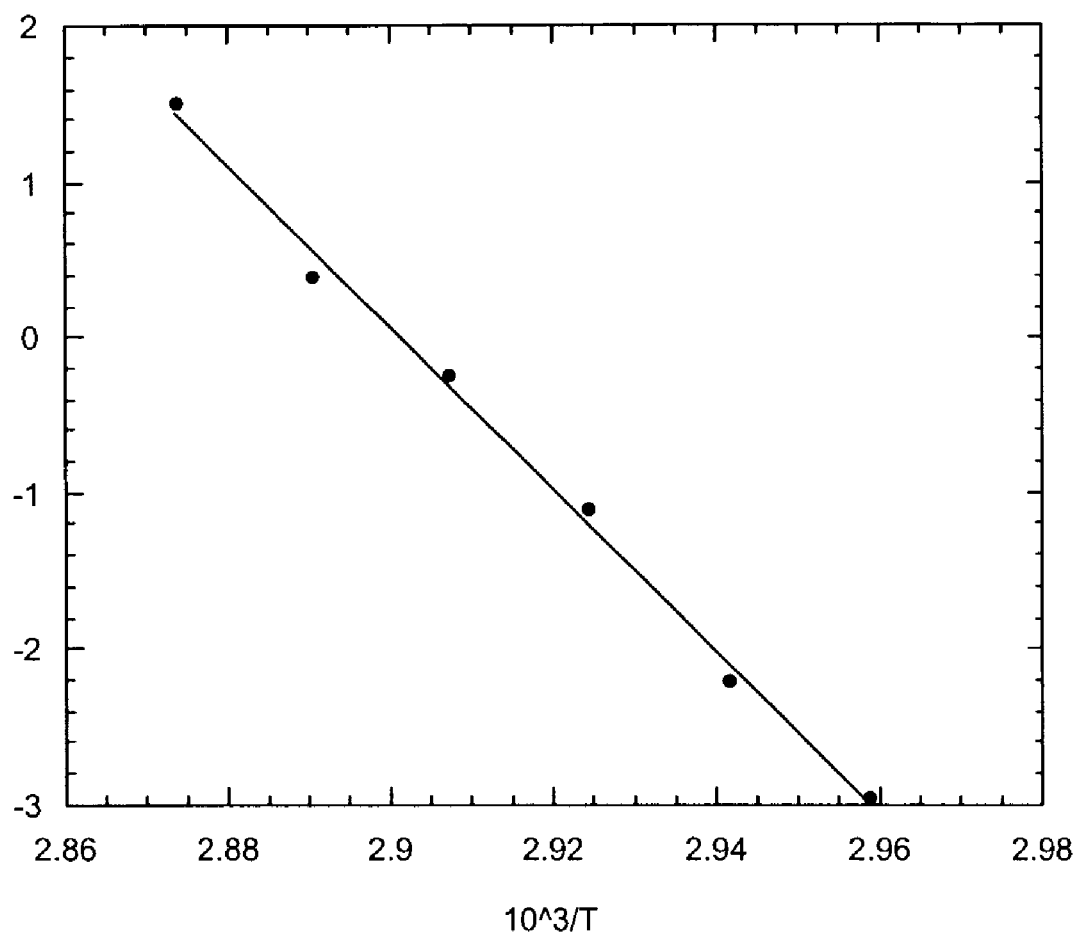
FIG. 13 also provides a thermodynamic characterization of the SEQ ID NO:5 polypeptide. The graph is a van't Hoff plot for thermal unfolding of the SEQ ID NO:5 polypeptide monitored by intrinsic tryptophan fluorescence. The natural logarithm of the equilibrium constant versus 1000/T is plotted, where T is the absolute temperature.

A van't Hoff plot, which illustrates the equilibria constants ($K_D$) determined by intrinsic tryptophan fluorescence, is provided in FIG. 13. The calculated temperature of maximum stability of 37.8° C. was ideal for a polypeptide that is to be introduced into wounds or in other physiological environments.

Protein-Protein Interactions

Figure 14:
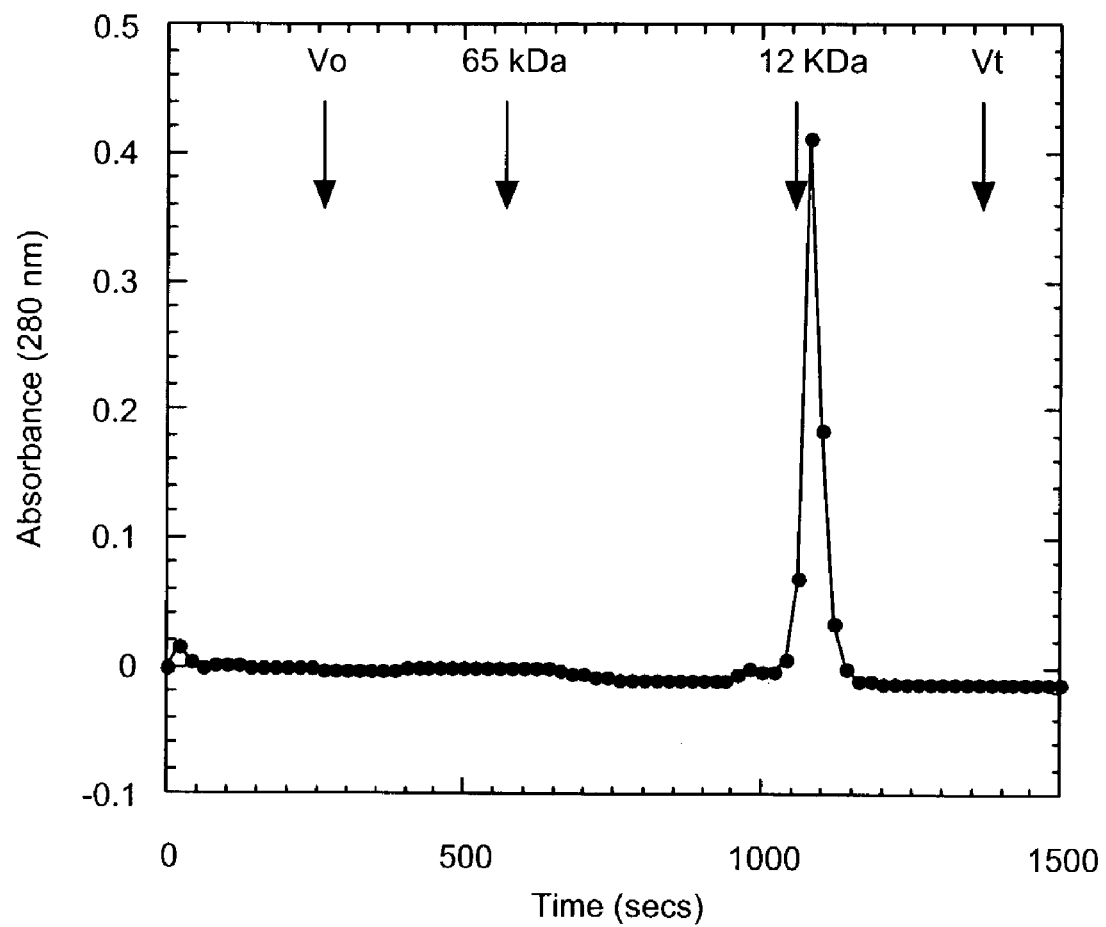
FIG. 14 provides a graph illustrating an analytical gel filtration analysis of the SEQ ID NO:5 polypeptide. 500 µg of purified the SEQ ID NO:5 polypeptide in PBS was injected onto a BioSelect 125 SEC column and chromatographed in PBS at a flow rate of 0.5 mL/min. The absorbance at 280 nm versus elution time is plotted. Superimposed on the graph are the elution points for myoglobin (12 kDa molecular weight), BSA (65 kDa molecular weight), and the positions of the column void volume ($V_o$) and the total volume ($V_t$).

The chromatographic behavior of the SEQ ID NO:5 polypeptide on the BioSelect 125 gel exclusion column was consistent with the expected monomeric protein. Results of an analytical gel filtration experiment are shown in FIG. 14. In this experiment, the SEQ ID NO:5 protein eluted from the column slightly later than a myoglobin standard (12 kDa) The elution profile was consistent with the SEQ ID NO:5 polypeptide being a monomeric protein with a molecular weight of approximately 11.8 kDa.

The calculated Stokes radius was 22 Å. This value is in good agreement with the dimensions of the atomic model. The elution profile suggested that the protein is primarily symmetric in nature because the frictional coefficient was 1.2. However, a frictional coefficient of 1.2 does indicate that the SEQ ID NO:5 polypeptide has a slightly oblate spheroid character, which may indicate that the loop region plays a part in determining the hydrodynamic properties of the protein.

Complex formation between the SEQ ID NO:5 polypeptide and MMP-9 was determined in three separate experiments.

Figure 15:
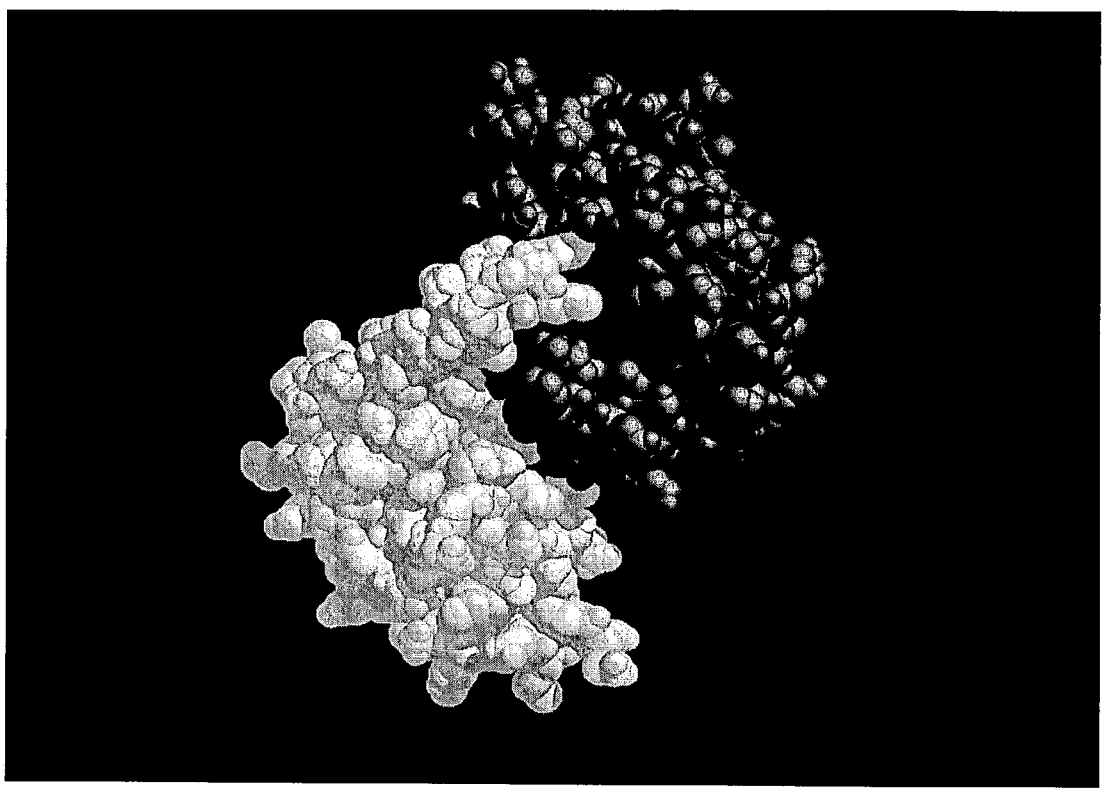
FIG. 15 provides a model of a predicted molecular complex between matrix metalloproteinase-9 (MMP-9) and the SEQ ID NO:5 polypeptide. The three dimensional coordinate files of MMP-9 (dark gray) and the SEQ ID NO:5 polypeptide (light gray) were used as input into the program FTDOCK (Gabb et al., 1997). The resulting model is the most probable complex that forms between the two proteins. FTDOCK evaluates both geometric and electrostatic considerations when calculating docking interactions. Both terms are combined into a robust Fourier correlation function.
Figure 16:
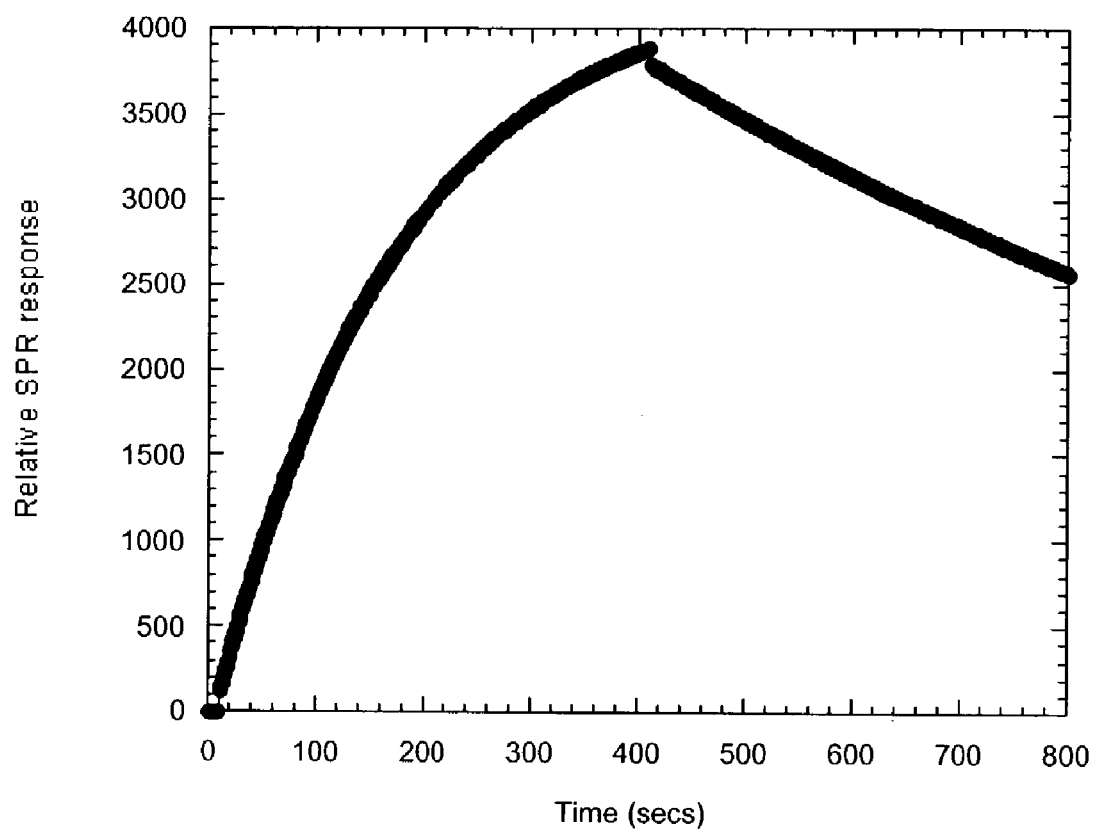
FIG. 16 provides a graph illustrating an SPR analysis of MMP-9~SEQ ID NO:5 polypeptide binding and dissociation. A BiaCore CM-5 chip surface was reacted with MMP-9 through activated carboxyl-amine linkage chemistry. Purified SEQ ID NO:5 polypeptide was flowed over this surface at a rate of 10 µL/min. The binding isotherm shows a high degree of affinity (zero to 400 seconds). At 400 seconds, the flow was replaced with buffer only in order to observe the dissociation phase.
Figure 17:
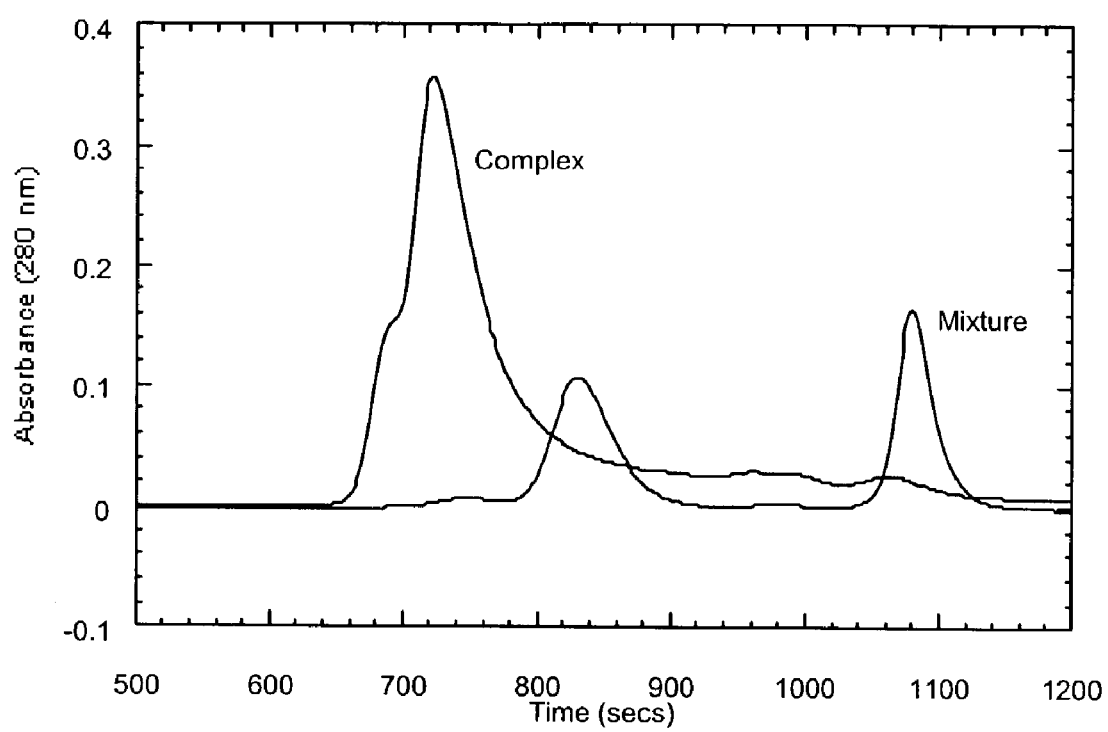
FIG. 17 provides a chromatograph illustrating formation of a SEQ ID NO:5 polypeptide~MMP-9 complex by HPLC analysis. 100 µg of the SEQ ID NO:5 polypeptide was mixed with 700 µg of MMP-9 (approximately 1 mM of each protein) in PBS, and the reaction was incubated at room temperature for 30 minutes in order to effect binding. The material was injected onto a BioSelect 125 SEC column and was chromatographed in PBS at a flow rate of 0.5 mL/min. This trace is marked as "complex" on the figure. In a second reaction, the same amount of the SEQ ID NO:5 polypeptide and MMP-9 were mixed together and were immediately injected onto the SEC column. This trace is marked as "mixture" on the figure.

In the first experiment, the atomic coordinate files for both molecules were used as input into the program FTDOCK (Gabb et al., 1977). The program calculated molecular surfaces for both molecules, then it held one molecule fixed while it performed a rigid body rotation of the second molecule about the first. For each orientation a fit score is calculated that takes both geometric and electrostatic considerations into account. Finally a series of best orientation structures was provided for inspection. The most probable molecular association between these two molecules is shown in FIG. 15. Note that the SEQ ID NO:5 polypeptide makes a significant contact with the matrix metalloproteinase along the planer proposed binding region. Moreover, the flexible loop region of the SEQ ID NO:5 polypeptide also has specific contacts with the matrix metalloproteinase. The structure determined for the complex buried approximately 300 Å$^2$ of the SEQ ID NO:5 polypeptide surface area.

In the second experiment, the molecular association between the SEQ ID NO:5 polypeptide and matrix metalloproteinase-9 (MMP-9) was measured directly using the technique of surface plasmon resonance. For this experiment, MMP-9 was coupled to the surface of a carboxymethylated dextran sensor chip. A solution of SEQ ID NO:5 polypeptide in PBS was permitted to flow freely over the MMP-9-bound surface. FIG. 16 shows the binding isotherm for this interaction. The curve could be fit to an association-disassociation model where the forward ($k_a$) and the reverse ($k_d$) rate constants were fit simultaneously. Such a fit resulted in a $k_a$ value of $2\times10^5$ $M^{-1}s^{-1}$, and a $k_d$ value of $1.3\times10^{-3}$ $s^{-1}$. This resulted in an equilibrium affinity constant ($K_A$) of $1.5\times10^8$ $M^{-1}$.

In the third experiment, analytical gel filtration was utilized to visualize pre-formed SEQ ID NO:5 polypeptide-MMP-9 complexes. Stoichiometric amounts of both proteins (1 mM) were mixed together and were allowed to incubate at room temperature. After 30 minutes, the entire reaction was injected onto a BioSelect 125 gel filtration column. The mixture eluted from this column as a single molecular weight species of 80 kDa apparent molecular weight (FIG. 17). These data indicate that the SEQ ID NO:5 polypeptide binds to MMP-9 in a 1:1 stoichiometry. As a control experiment, the two proteins were mixed together and immediately injected onto the column in order to show the individual protein elution positions. As can be seen in FIG. 17, there is a detectable amount of complex formed under these conditions.

REFERENCES

Agren, M. S. (1999). Matrix metalloproteinases (MMPs) are required for re-epithelialization of cutaneous wounds. Arch. Dermatol. Res. 291, 583–590.

Arnold, U., and Ulbrich-Hofmann, R. (1997). Kinetic and thermodynamic thermal stabilities of ribonuclease A and ribonuclease B. Biochemistry 36, 2166–2172.

Becker, J. W., Marcy, A. I., Rokosz, L. L., Axel, M. G., Burbaum, J. J., Fitzgerald, P. M., Cameron, P. M., Esser, C. K., Hagmann, W. K., Hermes, J. D., and Springer, J. P. (1995). Stromelysin-1: Three dimensional structure of the inhibited catalytic domain and of the C-truncated proenzyme. Protein Sci. 4, 1966–76.

Bodden, M. K., Harber, G. J., Birkedal-Hansen, B., Windsor, L. J., Caterina, N. C. M., Engler, J. A., and Birkedal-Hansen, J. (1994). Functional domains of human TIMP-1 (Tissue inhibitor of metalloproteinases). J. Biol. Chem. 269, 18943–18952.

Bradford, M. M. (1976). A rapid and sensitive method for the quantitation of microgram quantities of protein utilizing the principle of dye binding. Anal. Biochem. 72, 248–254.

Browner, M. F., Smith, W. W., Castelhano, A. L. (1995). Matrilysin-inhibitor complexes: Common themes among 18 metalloproteases. Biochemistry 34, 6602–10.

Butler, G. s., Hutton, M., Wattman, B. A., Williamson, R. A., Knauper, V., Willenbrock, F., and Murphy, G. (1999). The specificity of TIMP-2 for matrix metalloproteinases can be modified by single amino acid mutations. J. Biol. Chem. 274, 20391–20396.

Clark, M., Cramer, R. D., and van Opdensch, N. (1989). J. Computational Chem. 10, 982–986.

Di Colandrea, T., Wang, L., Wille, J., D'Armiento, J., and Chada, K. K. (1998). Epidermal expression of collagenase delays wound healing in transgenic mice. J. Invest. Dermatol. 111, 1029–1033.

Duivenvoorden, W. C. M., Hirte, H. W., and Singh, G. (1997). Use of tetracycline as an inhibitor of matrix metalloproteinase activity secreted by human bone metastasizing cancer cells. Invasion and Metas. 17, 312–322.

Fernandez-Catalan, C., Bode, W., Huber, R., Turk, D., Calvete, J. J., Lichte, A., Tschesche, H., and Maskos, K. (1998). Crystal structure of the complex formed by membrane type-1 matrix metalloproteinase with the tissue inhibitor of metalloproteinases-2, the soluble progelatinase A receptor. EMBO J. 17, 5238–48.

Gabb, H. A., Jackson, R. M., and Sternberg, M. J. (1997). Modelling protein docking using shape complementarity, electrostatics, and biochemical information. J. Mol. Biol. 272, 106–120.

Gomis-Ruth, F. X., Maskos, K., Betz, M., Bergner, A., Huber, R., Suzuki, K., Yoshida, N., Nagase, H., Brew, K., Bourenkov, G. P., Bartunik, H., and Bode, W. (1997). Mechanism of inhibition of the human matrix metalloproteinase stromelysin-1 by TIMP-1. Nature 389, 77–81.

Grams, F., Reinemer, P., Powers, J. C., Kleine, T., Pieper, M., Tschesche, H., Huber, R., Bode, W. (1995). X-ray structures of human neutrophil collagenase complexed with peptide hydroxamate and peptide thiol inhibitors: Implications for substrate binding and rational drug design. Eur. J. Biochem. 228, 830–834.

Guex, N. and Peitsch, M. C. (1997). Swiss Model and the Swiss-PdbViewer: An environment for comparative protein modeling. Electrophoresis 18, 2714–2723.

Higgins, D. G., Bleasby, A. J., and Fuchs, R. (1992). Clustal V: Improved software for multiple sequence alignment. CABIOS 8, 189–191.

Hodges, D. J., Reid, D. G., Rowan, A. D., Clark, I. M., and Cawston, T. E. (1998). Preparation of recombinant tissue inhibitor of metalloproteinase-1 (TIMP-1) in high yield and identification of a hydrophobic surface feature. Eur. J. Biochem. 257, 562–569.

Howard, E. W., Bullen, E. C., and Banda, M. J. (1991). Preferential inhibition of 72 and 92 kDa gelatinase by tisue inhibitor of metalloproteinase-2. J. Biol. Chem. 266, 13070–13075.

Huang, W., Suzuki, K., Nagase, H., Arumugam, S., Van Doren, S. R., and Brew, K. (1996). Folding and characterization of the amino terminal domain of human tissue inhibitor of metalloproteinases-1 (TIMP-1) expressed at high yield in *E. coli*. FEBS Lett. 384, 155–161.

Hutton, M., Butler, G. S., Wattam, B. A., Willenbrock, F., Williamson, R. A., and Murphy, G. (1999). Analysis of the interaction of TIMP-2 and MMPs: Engineering the changes. Annal. NY Academ. Sci. 878, 524–527.

Kaiser, D. A. and Pollard, T. D. (1996). Characterization of actin and poly-L-proline binding sites of Acanthaoemba profilin with monoclonal antibodies and by mutagenesis. J. Mol. Biol. 255, 89–107.

Karlsson, R., and Falt, A. (1997). Experimental design for kinetic analysis of protein-protein interactions with surface plasmon resonance biosensors. J. Immunol. Meths. 200, 121–33.

Laemmli, U. K. (1970). Cleavage of structural proteins during the assembly of the head of bacteriophage T4. Nature (London) 227, 680–685.

Lakowicz, J. R. (1983). *Principles of Fluorescence Spectroscopy*, Chapter 10, Plenum Press, New York, London.

Levy, D. E., Lapierre, F., Liang, W., Ye, W., Lange, C. W., Li, X., Grobelny, D., Casabonne, M., Tyrrell, D., Holme, K., Nadzan, A., and Galardy, R. E. (1998). Matrix metalloproteinase inhibitors: A structure activity study. J. Med. Chem. 41, 199–223.

Libson, A. M., Gittis, A. G., Collier, I. E., Marmer, B. L., Goldberg, G. I., and Lattman, E. E. (1995). Crystal structure of the haemopexin-like C terminal domain of gelatinase A. Nat. Struct. Biol. 2, 938–42.

Liu, Y. E., Wang, M., Greene, J., Su, J., Ullrich, S., Li, H., Sheng, S., Alexander, P., Sang, Q. A., and Shi, Y. E. (1997). Preparation and characterization of recombinant tissue inhibitor of metalloproteinase 4 (TIMP-4). J. Biol. Chem. 272, 20479–20483.

Lofas, S., Johnsson, B., Tegendahl, K., and Ronnberg, I. (1993). Dextran modified gold surfaces for surface plasmon resonance biosensors; immunoreactivity of immobilized antibodies and antibody-surface interaction studies. J. Colloid Interface Sci. 65, 423–431.

Maniatis, T., Fritch, E. F., and Sambrook, J. (1981). Molecular Cloning: A Laboratory Manual, Cold Spring Harbor Laboratory, Cold Spring Harbor, N.Y.

Meng, Q., Malinovski, V., Huang, W., Hu, Y., Chung, L., Nagase, H., Bode, W., Maskos, K., and Brew, K. (1999). Residue 2 of TIMP-1 is a major determinant of affinity and specificity for matrix metalloproteinases but effects of substitutions do not correleate with those of the corresponding P1' residue of substrate. J. Biol. Chem. 274, 10184–10189.

Miller, J. H. (1972). Experiments in Molecular Genetics. Cold Spring Harbor Laboratory, Cold Spring Harbor, N.Y.

Morton, T. A., Myska, D. G., and Chaiken, I. M. (1995). Interpreting complex binding kinetics from optical biosensors: A comparison of analysis by linearization, the integrated rate equation, and numerical integration. Anal. Biochem. 227, 176–185.

Moses, M. A., Marikovsky, M., Harper, J. W., Vogt, P., Eriksson, E., Klagsbrun, M. and Langer, R. (1996). Temporal study of the activity of matrix metalloproteinases and their endogenous inhibitors during wound healing. J. Cell. Biochem. 60, 379–386.

Odake, S., Morita, Y., and Morikawa, T. (1994). Inhibition of matrix metalloproteinases by peptidyl hydroxamic acids. Biochem. Biophys. Res. Comm. 199, 1442–1446.

Olson, M. W., Gervasi, D. C., Mobashery, S., and Fridman, R. (1997). Kinetic analysis of the binding of human matrix metalloproteinase 2 and 9 to tissue inhibitor of metalloproteinase (TIMP)-1 and TIMP-2. J. Biol. Chem. 272, 29975–29983.

O'Shannessy, D. J., Brigham-Burke, M., Soneson, K. K, Hensley, P., and Brooks, I. (1993). Determination of rate and equilibrium binding constants for macromolecular interactions using surface plasmon resonance: use of non linear least squares analysis methods. Anal. Biochem. 212, 457–468.

Overall, C. M., King, A. E., Sam, D. K., Ong, A. D., Lau, T. T. Y., Wallon, U. M., DeClerck, Y. A., and Atherstone, J. (1999). Identification of the tissue inhibitor of metalloproteinase-2 (TIMP-2) binding site on the hemopexin carboxyl domain of human gelatinase A by site directed mutagenesis. J. Biol. Chem. 274, 4421–4429.

Pace, C. N., Shirley, B. A., and Thomson, J. A. (1989). In Protein Structure a practical approach (T. E. Creighton, Ed.), pp. 311–330. IRL Press, Oxford, UK.

Peitsch, M. C. (1996). ProMod and Swiss-Model: Internet-based tools for automated comparative protein modelling. Biochem. Soc. Trans. 24:274–279.

Peitsch M C, Herzyk P, Wells T N C and Hubbard R E (1996) Automated modelling of the transmembrane region of G-protein coupled receptor by Swiss-Model. Receptors and Channels 4:161–164.

Quirk, S., Maciver, S. K., Ampe, C., Doberstein, S. K., Kaiser, D. A., VanDamme, J., Vandekerckhove, J. S., and Pollard, T. D. (1993). Primary structure of and studies on Acanthamoeba actophorin. Biochemistry, 32: 8525–8533.

Reinemer, P., Grams, F., Huber, R., Kleine, T., Schnierer, S., Pieper, M., Tschesche, H., Bode, W. (1994). Structural implications for the role of the N terminus in the superactivation of collagenases: A crystallographic study. FEBBS Lett. 338, 227–33.

Saarialho-Kere, U. K. (1998). Patterns of matrix metalloproteinase and TIMP expression in chronic ulcers. Arch. Dermatol. Res. 290 (suppl), 47–54.

Sambrook, J., Fritch, E F., and Maniatis, T. (1989). Molecular Cloning: A Laboratory Manual, $2^{nd}$ ed., Cold Spring Harbor Laboratory, Cold Spring Harbor, N.Y.

Sanger, F., Nicklen, S., and Coulson, A. R. (1977). DNA sequencing with chain terminating inhibitors. Proc. Nat. Acad. Sci. U.S.A. 74, 5643–5647.

Sayle, R. A. and Milner-White, E. J. (1995). RasMol: Biomolecular graphics for all. Trends in Biochemical Sciences 20, 374–376.

Segel, I H. (1993) Enzyme Kinetics: Behavior and analysis of rapid equilibrium and steady-state enzyme systems. Wiley Classics Library, John Wiley and Sons, Inc. New York.

Siegel, L M., and Monty, K J. (1966). Determination of molecular weights and frictional ratios of proteins in impure systems by the use of gel filtration and density gradient centrifugation. Application to crude preparations of sulfite and hydroxylamine reductases. Biochim. Biophys. Acta 112, 346–362.

Su, J-L., Becherer, D., Edwards, C., Bukhart, W., McMgeehan, G. M., and Champion, B. R. (1995). Monoclonal antibodies against human collagenase and stromelysin. Hybridoma. 14, 383–390.

Taylor, K. B., Windsor, J. L., Caterina, N. C. M., Bodden, M. K., and Engler, J. A. (1996). The mechanism of inhibition of collagenase by TIMP-1. J. Biol. Chem. 271, 23938–23945.

Tuuttila, A., Morgunov, E., Bergmann, U., Lindqvist, Y., Maskos, K., Fernandez-Catalan, C., Bode, W., Tryggvason, K., and Schneider, G. (1998). Three dimensional structure of human tissue inhibitor of metalloproteinases-2 at 2.1 Å resolution. J. Mol. Biol. 284, 1133–1140.

Vaalamo, M., Weckroth, M., Puolakkainen, P., Kere, J., Saarinen, P., Lauharanta, J., and Saarialho-Kere, U. K. (1996). Patterns of matrix metalloproteinase and TIMP-1 expression in chronic and normally healing human cutaneous wounds. Brit. J. Dermatol. 135, 52–59.

Vaalamo, M., Mattila, L., Johansson, N., Kariniemi, A-L., Karjalainen-Lindsberg, M-L., Kahari, V-M., and Saarialho-Kere, U. K. (1997). Distinct populations of stromal cells express collagenase-3 (MMP-13) and collagenase-1 (MMP-1) in chronic ulcers, but not in normally healing wounds. J. Investig. Dermatol. 109, 96–101.

Vallon, R., Muller, R., Moosmayer, D., Gerlach, E., and Angel, P. (1997). The catalytic domain of activated collagenase I (MMP-1) is absolutely required for interaction with its specific inhibitor, tissue inhibitor of metalloproteinase-1 (TIMP-1). Eur. J. Biochem. 244, 81–88.

Weckroth, M., Vaheri, A., Lauharanta, J., Sorsa, T., and Konttinen, Y. T. (1996). Matrix metalloproteinases, gelatinases, and collagenases in chronic leg ulcers. J. Investig. Dermatol. 108, 1119–1124.

Wingfield, P. T., Sax, J. K., Stahl, S. J., Kaufman, J., Palmer, I., Chung, V., Corcoran, M. L., Kleiner, D. E., and Stetler-Stevenson, W. G. (1999). Biophysical and Functional characterization of full-length recombinant human tissue inhibitor of metalloproteinase-2 (TIMP-2) produced in *E. coli*. J. Biol. Chem. 274, 21362–21368.

Wojtowicz-Praga, S. M., Dickson, R. B., and Hawkins, M. J. (1997). Matrix metalloproteinase inhibitors. Investigational New Drugs. 15, 61–75.

All publications and patents are incorporated by reference herein, as though individually incorporated by reference. The invention is not limited to the exact details shown and described, for it should be understood that many variations and modifications may be made while remaining within the spirit and scope of the invention defined by the claims.

---

What is claimed:

1. An isolated polypeptide comprising SEQ ID NO:5 or SEQ ID NO:20.

2. The isolated polypeptide of claim 1, wherein the polypeptide inhibits matrix metalloproteinase activity.

3. The isolated polypeptide of claim 1, wherein the polypeptide is stable in mammalian serum or plasma.

4. The isolated polypeptide of claim 1, wherein substantially all of the polypeptide remains folded in a beta barrel conformation while in 1M urea.

5. A composition that comprises a therapeutically effective amount of polypeptide inhibitor comprising SEQ ID NO:5 or SEQ ID NO:20 and a pharmaceutically acceptable carrier.

6. The composition of claim 5 wherein the polypeptide inhibitor can inhibit proteinase activity of any one of matrix metalloproteinase-1, matrix metalloproteinase-2, matrix metalloproteinase-3, matrix metalloproteinase-4, matrix metalloproteinase-5, matrix metalloproteinase-6, matrix metalloproteinase-7, matrix metalloproteinase-8, and matrix metalloproteinase-9, matrix metalloproteinase-10, matrix metalloproteinase-11, matrix metalloproteinase-12, or matrix metalloproteinase-13.

7. The composition of claim 5, wherein the polypeptide inhibitor can inhibit more than one of matrix metalloproteinase-1, matrix metalloproteinase-2, matrix metalloproteinase-3, matrix metalloproteinase-4, matrix metalloproteinase-5, matrix metalloproteinase-6, matrix metalloproteinase-7, matrix metalloproteinase-8, and matrix metalloproteinase-9, matrix metalloproteinase-10, matrix metalloproteinase-11, matrix metalloproteinase-12, or matrix metalloproteinase-13.

8. The composition of claim 5, wherein the polypeptide inhibitor has a beta barrel conformation.

9. The composition of claim 5, wherein the polypeptide is stable in mammalian serum.

10. The composition of claim 5, wherein substantially all of the polypeptide remains folded in a beta barrel conformation while in 4M urea.

11. The composition of claim 5, wherein the composition comprises a lotion, gel or cream.

12. A wound dressing that comprises a polypeptide comprising SEQ ID NO:5 or SEQ ID NO:20 and a pharmaceutically acceptable carrier.

13. The wound dressing of claim 12, wherein the polypeptide can inhibit proteinase activity of any one of matrix metalloproteinase-1, matrix metalloproteinase-2, matrix metalloproteinase-3, matrix metalloproteinase-4, matrix metalloproteinase-5, matrix metalloproteinase-6, matrix metalloproteinase-7, matrix metalloproteinase-8, and matrix metalloproteinase-9, matrix metalloproteinase-10, matrix metalloproteinase-11, matrix metalloproteinase-5, or matrix metalloproteinase.

14. The wound dressing of claim 12, wherein the polypeptide can inhibit more than one of matrix metalloproteinase-1, matrix metalloproteinase-2, matrix metalloproteinase-3, matrix metalloproteinase-4, matrix metalloproteinase-5, matrix metalloproteinase-6, matrix metalloproteinase-7, matrix metalloproteinase-8, and matrix metalloproteinase-9, matrix metalloproteinase-10, matrix metalloproteinase-11, matrix metalloproteinase-12, or matrix metalloproteinase-13.

15. The wound dressing of claim 12, wherein the polypeptide has a beta barrel conformation.

16. The wound dressing of claim 12, wherein the polypeptide is stable in mammalian serum.

17. The wound dressing of claim 12, wherein substantially all of the polypeptide remains folded in a beta barrel conformation while in 4M urea.

18. The wound dressing of claim 12, wherein the pharmaceutically acceptable carrier is a bandage.

19. A method for treating a wound that comprises administering a therapeutically effective amount of a polypeptide comprising SEQ ID NO:5 or SEQ ID NO:20 to the wound.

20. The method of claim 19, wherein the polypeptide can inhibit proteinase activity of any one of matrix metalloproteinase-1, matrix metalloproteinase-2, matrix metalloproteinase-3, matrix metalloproteinase-4, matrix metalloproteinase-5, matrix metalloproteinase-6, matrix metalloproteinase-7, matrix metalloproteinase-8, and matrix metalloproteinase-9, matrix metalloproteinase-10, matrix metalloproteinase-11, matrix metalloproteinase-12, or matrix metalloproteinase.

21. The method of claim 19, wherein the polypeptide can inhibit more than one of matrix metalloproteinase-1, matrix metalloproteinase-2, matrix metalloproteinase-3, matrix metalloproteinase-4, matrix metalloproteinase-5, matrix metalloproteinase-6, matrix metalloproteinase-7, matrix metalloproteinase-8, and matrix metalloproteinase-9, matrix metalloproteinase-10, matrix metalloproteinase-11, matrix metalloproteinase-12, or matrix metalloproteinase-13.

22. The method of claim 19, wherein the polypeptide has a beta barrel conformation.

23. The method of claim 19, wherein the polypeptide is stable in mammalian serum.

24. The method of claim 19, wherein substantially all of the polypeptide remains folded in a beta barrel conformation while in 4M urea.

* * * * *